US006207374B1

(12) United States Patent
Sampson et al.

(10) Patent No.: US 6,207,374 B1
(45) Date of Patent: Mar. 27, 2001

(54) TUBEROUS SCLEROSIS 2 GENE AND USES THEREOF

(75) Inventors: Julian R. Sampson, Cardiff (GB); Mark David Nellist, Rotterdam (NL); Phillip Brook-Carter, Wonthaggi (AU); Magitha Maheshwar, Mid Glamorgan (GB); Dirkje Jorijnte Johanna Halley, Rotterdam (NL); Lambertus Antonius Jacobus Janssen, Mauer (DE); Arjenne Lique Wilhelma Hesseling, Spijkenisse; Anna Maria Wilhelmina van den Ouweland, Simonshaven, both of (NL); Peter Charles Harris; Christopher James Ward, both of Oxford (GB); Martin Hendrik Breuning, Zaandam; Jeroen Hendrik Roelfsema, Leiden, both of (NL)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/040,738

(22) Filed: Mar. 18, 1998

Related U.S. Application Data

(62) Division of application No. 08/652,426, filed as application No. PCT/GB94/02823 on Dec. 23, 1994.

(30) Foreign Application Priority Data

Dec. 24, 1993 (GB) .................................................. 9326470
Jun. 14, 1994 (GB) .................................................. 9411900

(51) Int. Cl.[7] .............................. C12Q 1/68; C12P 19/34; C07H 21/02

(52) U.S. Cl. .......................... 435/6; 435/91.1; 435/91.2; 536/24.3; 536/24.31; 536/24.33

(58) Field of Search ............................ 435/6, 91.1, 91.2; 536/24.3, 24.31, 24.33

(56) References Cited

FOREIGN PATENT DOCUMENTS

WO16178   8/1993   (WO) .
WO 95/18226  *  7/1995   (WO) .

OTHER PUBLICATIONS

Kandt et al, "Linkage of an important gene locus for tuberous sclerosis to a chromosome 16 marker for polycystic kidney disease", Nature Genetics 2:37–41, Sep. 1992.*
Adams et al., (1993) Nature Genet. 4:373–380.
Al–Gazali et al., (1989) J. Med. Genet. 26:694–703.
Bernstein et al., (1974) Birth Defects: Original Article Series 10:35–43.
Bernstein and Robbins, (1991) Ann. N.Y. Acad. Sci 615:36–49.
Brook–Carter et al., (1994) Nature Genet. 8:328–332.
Chomczynski and Sacchi, (1987) Anal. Biochem. 162:156–159.
Dayhoff et al., (1978) Atlas of Protein Sequence and Structure 5(3):345–352.
Deisseroth and Hendrick, (1979) Proc. Natl. Acad. Sci. USA 76:2185–2189.
Eisenberg et al., (1984) J. Mol. Biol. 179:125–142.
European Polycycstic Kidney Disease Consortium (1994) Cell 77:881–894.
European Chromosome 16 Tuberous Sclerosis Consortium (1993) Cell 75:1305–1315.
Feinberg and Vogelstein, (1984) Anal. Biochem. 137:266–267.
Fryer et al., (1987) Lancet, 659–661.
Fryer et al., (1990) J. Med. Genet. 27:217–223.
Germino et al., (1990) Am. J. Hum. Genet. 46:925–933.
Germino et al., (1992) Genomics 13:144–151.
Germino et al., (1993) Kidney International 43(39):S–20–S–25.
Glass et al., (1986) J. Biol. Chem. 261:2987–2993.
Green and Yates, (1993) Am. J. Hum. Genet. 53(Suppl):Abs 244.
Green and Yates, (1994) Nature Genet. 6:193–196.
Green and Yates, (1994) Hum. Molec. Genet. (In the press).
Haines et al., (1991) Ann. N.Y. Acad. Sci. 615:256–264.
Haines et al., (1991) Am. J. Hum. Genet. 49:764–772.
Harris et al., (1990) Genomics 7:195–206.
Herrmann et al., (1987) Cell 48:813–825.
Himmelbauer et al., (1991) Am. J. Hum. Genet. 48:325–334.
Horowitz et al., (1989) Science 243:937–940.
Janssen et al., (1991) Ann. N.Y. Acad. Sci. 615:306–315.
Kandt et al., (1992) Nature Genet. 2:37–41.
Knudson, A.G., (1971) Proc. Natl. Acad. Sci. USA 68:820–823.
Kozak, M., (1987) Nucl. Acids Res. 15:8125–8148.
Kwiatkowski et al., (1993) Cytogenet. Cell Genet. 64:94–106.
Landschultz et al., (1988) Science 240:1759–1764.
Latif et al., (1993) Science 260:1317–1320.
Legius et al., (1993) Nature Genet. 3:122–126.
Martin et al., (1990) Cell 63:843–849.
Mulley et al., (1993) Cur. Opin. Genet. Develop. 3:425–431.
Nellist et al., (1993) J. Med. Genet. 30:224–227.
Northrup et al., (1992) Am. J. Hum. Genet. 51:709–720.

(List continued on next page.)

Primary Examiner—Jeffrey Fredman
(74) Attorney, Agent, or Firm—Kathleen M. Williams; Elizabeth Sparr; Palmer & Dodge. LLP

(57) ABSTRACT

Tuberous sclerosis (TSC) is an autosomal dominant disorder characterised by widespread development of growths in many tissues and organs. A gene (TSC2) is identified on chromosome 16 which is mutated in TSC and which may behave as a tumour suppressor. Screening of actual or suspected TSC patients for normal or mutated TSC2 can be used for diagnostic purposes. TSC2 protein (tuberin) may be used to treat or prevent unrestrained cell division and/or tumour development in patients with or without TSC.

6 Claims, 27 Drawing Sheets

OTHER PUBLICATIONS

Orita et al., (1989) Proc. Natl. Acad. Sci. USA 86:2766–2770.
Osborne et al., (1991) Ann. N.Y. Acad. Sci. 615:125–127.
Patschinsky et al., (1982) Proc. Natl. Acad. Sci. USA 79:973–977.
Pinna, L.A., (1990) Biochim. Biophys. Acta 1054:267–284.
Povey et al., (1991) Ann. N.Y. Acad. Sci. 615:298–305.
Rack et al., (1993) Am. J. Hum. Genet. 52:987–997.
Riordan et al., (1989) Science 245:1066–1073.
Rouleau et al., (1993) Nature 363:515–521.
Royle et al., (1992) Nucl. Acids Res. 20:1164.
Rubinfeld et al., (1992) Mol. Cell. Biol. 12:4634–4642.
Sambrook et al., (1989) Molecular Cloning:A Laboratory Manual, Second Edition, (Cold Spring Harbor Press) pp. 9.31–9.62.
Sampson et al., (1989) J. Med. Genet. 26:511–516.
Sampson et al., (1989) J. Med. Genet. 26:28–31.
Sampson et al., (1992) J. Med. Genet. 29:861–866.
Stallings et al., (1990) Proc. Natl. Acad. Sci. USA 87:6218–6222.
Thompson et al., (1992) Genomics 13:402–408.
Trofatter et al., (1993) Cell 72:791–800.
Viskochil et al., (1990) Cell 62:187–192.
von Heijne, G., (1985) J. Mol. Biol. 184:99–105.
Wilkie et al., (1990) Am. J. Hum. Genet. 46:1112–1126.
Woodgett et al., (1986) Eur. J. Biochem. 161:177–184.
Xu et al., (1990) Cell 62:599–608.

* cited by examiner

FIG. 3a

```
GGTGCGTCCTGGTCCACCATGGCCAAACCAACAAGCAAAGATTCAGGCTTGAAGGAGAAG  60
                M  A  K  P  T  S  K  D  S  G  L  K  E  K    14

TTTAAGATTCTGTTGGGACTGGGAACACCGAGGCCAAATCCCAGGTCTGCAGAGGGTAAA  120
 F  K  I  L  L  G  L  G  T  P  R  P  N  P  R  S  A  E  G  K   34

CAGACGGAGTTTATCATCACCGCGGAAATACTGAGAGAACTGAGCATGGAATGTGGCCTC  180
 Q  T  E  F  I  I  T  A  E  I  L  R  E  L  S  M  E  C  G  L   54

AACAATCGCATCCGGATGATAGGGCAGATTTGTGAAGTCGCAAAAACCAAGAAATTTGAA  240
 N  N  R  I  R  M  I  G  Q  I  C  E  V  A  K  T  K  K  F  E   74
                                              ▼

GAGCACGCAGTGGAAGCACTCTGGAAGGCGGTCGCGGATCTGTTGCAGCCGGAGCGGACG  300
 E  H  A  V  E  A  L  W  K  A  V  A  D  L  L  Q  P  E  R  T   94
    r                     .___.___.r  .  .  .  .  .  .  .  .

CTGGAGGCCCGGCACGCGGTGCTGGCTCTGCTGAAGGCCATCGTGCAGGGGCAGGGCGAG  360
 L  E  A  R  H  A  V  L  A  L  L  K  A  I  V  Q  G  Q  G  E  114
 .  .  .  .  r .___.___.___._____r

CGTTTGGGGGTCCTCAGAGCCCTCTTCTTTAAGGTCATCAAGGATTACCCTTCCAACGAA  420
 R  L  G  V  L  R  A  L  F  F  K  V  I  K  D  Y  P  S  N  E  134
                                              ►

GACCTTCACGAAAGGCTGGAGGTTTTCAAGGCCCTCACAGACAATGGGAGACACATCACC  480
 D  L  H  E  R  L  E  V  F  K  A  L  T  D  N  G  R  H  I  T  154
                                                       ►

TACTTGGAGGAAGAGCTGGCTGACTTTGTCCTGCAGTGGATGGATGTTGGCTTGTCCTCG  540
 Y  L  E  E  E  L  A  D  F  V  L  Q  W  M  D  V  G  L  S  S  174
                                              ═════════════════

GAATTCCTTCTGGTGCTGGTGAACTTGGTCAAATTCAATAGCTGTTACCTCGACGAGTAC  600
 E  F  L  L  V  L  V  N  L  V  K  F  N  S  C  Y  L  D  E  Y  194
═══════════════════════════════════════════════════

ATCGCAAGGATGGTTCAGATGATCTGTCTGCTGTGCGTCCGGACCGCGTCCTCTGTGGAC  660
 I  A  R  M  V  Q  M  I  C  L  L  C  V  R  T  A  S  S  V  D  214
                                     ►

ATAGAGGTCTCCCTGCAGGTGCTGGACGCCGTGGTCTGCTACAACTGCCTGCCGGCTGAG  720
 I  E  V  S  L  Q  V  L  D  A  V  V  C  Y  N  C  L  P  A  E  234

AGCCTCCCGCTGTTCATCGTTACCCTCTGTCGCACCATCAACGTCAAGGAGCTCTGCGAG  780
 S  L  P  L  F  I  V  T  L  C  R  T  I  N  V  K  E  L  C  E  254

CCTTGCTGGAAGCTGATGCGGAACCTCCTTGGCACCCACCTGGGCCACAGCGCCATCTAC  840
 P  C  W  K  L  M  R  N  L  L  G  T  H  L  G  H  S  A  I  Y  274
```

FIG. 3b

```
AACATGTGCCACCTCATGGAGGACAGAGCCTACATGGAGGACGCGCCCCTGCTGAGAGGA 900
 N  M  C  H  L  M  E  D  R  A  Y  M  E  D  A  P  L  L  R  G  294

GCCGTGTTTTTTGTGGGCATGGCTCTCTGGGGAGCCCACCGGCTCTATTCTCTCAGGAAC 960
 A  V  F  F  V  G  M  A  L  W  G  A  H  R  L  Y  S  L  R  N  314

TCGCCGACATCTGTGTTTCCATCATTTTACCAGGCCATGGCATGTCCGAACGAGGTGGTG 1020
 S  P  T  S  V  F  P  S  F  Y  Q  A  M  A  C  P  N  E  V  V  334

TCCTATGAGATCGTCCTGTCCATCACCAGGCTCATCAAGAAGTATAGGAAGGAGCTCCAG 1080
 S  Y  E  I  V  L  S  I  T  R  L  I  K  K  Y  R  K  E  L  Q  354

GTGGTGGCGTGGGACATTCTGCTGAACATCATCGAACGGCTCCTTCAACAGCTCCAGACC 1140
 V  V  A  W  D  I  L  L  N  I  I  E  R  L  L  Q  Q  L  Q  T  374

TTGGACAGCCCGGAGCTCAGGACCATCGTCCATGACCTGTTGACCACGGTGGAGGAGCTG 1200
 L  D  S  P  E  L  R  T  I  V  H  D  L  L  T  T  V  E  E  L  394

TGTGACCAGAACGAGTTCCACGGGTCTCAGGAGAGATACTTTGAACTGGTGGAGAGATGT 1260
 C  D  Q  N  E  F  H  G  S  Q  E  R  Y  F  E  L  V  E  R  C  414

GCGGACCAGAGGCCTGAGTCCTCCCTCCTGAACCTGATCTCCTATAGAGCGCAGTCCATC 1320
 A  D  Q  R  P  E  S  S  L  L  N  L  I  S  Y  R  A  Q  S  I  434

CACCCGGCCAAGGACGGCTGGATTCAGAACCTGCAGGCGCTGATGGAGAGATTCTTCAGG 1380
 H  P  A  K  D  G  W  I  Q  N  L  Q  A  L  M  E  R  F  F  R  454

AGCGAGTCCCGAGGCGCCGTGCGCATCAAGGTGCTGGACGTGCTGTCCTTTGTGCTGCTC 1440
 S  E  S  R  G  A  V  R  I  K  V  L  D  V  L  S  F  V  L  L  474

ATCAACAGGCAGTTCTATGAGGAGGAGCTGATTAACTCAGTGGTCATCTCGCAGCTCTCC 1500
 I  N  R  Q  F  Y  E  E  E  L  I  N  S  V  V  I  S  Q  L  S  494

CACATCCCCGAGGATAAAGACCACCAGGTCCGAAAGCTGGCCACCCAGTTGCTGGTGGAC 1560
 H  I  P  E  D  K  D  H  Q  V  R  K  L  A  T  Q  L  L  V  D  514

CTGGCAGAGGGCTGCCACACACACCACTTCAACAGCCTGCTGGACATCATCGAGAAGGTG 1620
 L  A  E  G  C  H  T  H  H  F  N  S  L  L  D  I  I  E  K  V  534

ATGGCCCGCTCCCTCTCCCCACCCCCGGAGCTGGAAGAAAGGGATGTGGCCGCATACTCG 1680
 M  A  R  S  L  S  P  P  P  E  L  E  E  R  D  V  A  A  Y  S  554

GCCTCCTTGGAGGATGTGAAGACAGCCGTCCTGGGGCTTCTGGTCATCCTTCAGACCAAG 1740
 A  S  L  E  D  V  K  T  A  V  L  G  L  L  V  I  L  Q  T  K  574
```

FIG. 3c

```
CTGTACACCCTGCCTGCAAGCCACGCCACGCGTGTGTATGAGATGCTGGTCAGCCACATT 1800
 L  Y  T  L  P  A  S  H  A  T  R  V  V  Y  E  M  L  V  S  H  I  594

CAGCTCCACTACAAGCACAGCTACACCCTGCCAATCGCGAGCAGCATCCGGCTGCAGGCC 1860
 Q  L  H  Y  K  H  S  Y  T  L  P  I  A  S  S  I  R  L  Q  A  614
                                            ▼

TTTGACTTCCTGTTTCTGCTGCGGGCCGACTCACTGCACCGCCTGGGCCTGCCCAACAAG 1920
 F  D  F  L  F  L  L  R  A  D  S  L  H  R  L  G  L  P  N  K  634

GATGGAGTCGTGCGGTTCAGCCCCTACTGCGTCTGCGACTACATGGAGCCAGAGAGAGGC 1980
 D  G  V  V  R  F  S  P  Y  C  V  C  D  Y  M  E  P  E  R  G  654

TCTGAGAAGAAGACCAGCGGCCCCCTTTCTCCTCCCACAGGGCCTCCTGGCCCGGCGCCT 2040
 S  E  K  K  T  S  G  P  L  S  P  P  T  G  P  P  G  P  A  P  674
 ▼              ▲

GCAGGCCCCGCCGTGCGGCTGGGGTCCGTGCCCTACTCCCTGCTCTTCCGCGTCCTGCTG 2100
 A  G  P  A  V  R  L  G  S  V  P  Y  S  L  L  F  R  V  L  L  694

CAGTGCTTGAAGCAGGAGTCTGACTGGAAGGTGCTGAAGCTGGTTCTGGGCAGGCTGCCT 2160
 Q  C  L  K  Q  E  S  D  W  K  V  L  K  L  V  L  G  R  L  P  714

GAGTCCCTGCGCTATAAAGTGCTCATCTTTACTTCCCCTTGCAGTGTGGACCAGCTGTGC 2220
 E  S  L  R  Y  K  V  L  I  F  T  S  P  C  S  V  D  Q  L  C  734
       ▼        #

TCTGCTCTCTGCTCCATGCTTTCAGGCCCAAAGACACTGGAGCGGCTCCGAGGCGCCCCA 2280
 S  A  L  C  S  M  L  S  G  P  K  T  L  E  R  L  R  G  A  P  754

GAAGGCTTCTCCAGAACTGACTTGCACCTGGCCGTGGTTCCAGTGCTGACAGCATTAATC 2340
 E  G  F  S  R  T  D  L  H  L  A  V  V  P  V  L  T  A  L  I  774
          ▶

TCTTACCATAACTACCTGGACAAAACCAAACAGCGCGAGATGGTCTACTGCCTGGAGCAG 2400
 S  Y  H  N  Y  L  D  K  T  K  Q  R  E  M  V  Y  C  L  E  Q  794
                                            #

GGCCTCATCCACCGCTGTGCCAGACAGTGCGTCGTGGCCTTGTCCATCTGCAGCGTGGAG 2460
 G  L  I  H  R  C  A  R  Q  C  V  V  A  L  S  I  C  S  V  E  814
 ═══════════════════════════════════════════════════════════

ATGCCTGACATCATCATCAAGGCGCTGCCTGTTCTGGTGGTGAAGCTCACGCACATCTCA 2520
 M  P  D  I  I  I  K  A  L  P  V  L  V  V  K  L  T  H  I  S  834
 ─────────────────────────────────────────────────────────
```

FIG. 3d

```
GCCACAGCCAGCATGGCCGTCCCACTGCTGGAGTTCCTGTCCACTCTGGCCAGGCTGCCG 2580
 A  T  A  S  M  A  V  P  L  L  E  F  L  S  T  L  A  R  L  P  854

CACCTCTACAGGAACTTTGCCGCGGAGCAGTATGCCAGTGTGTTCGCCATCTCCCTGCCG 2640
 H  L  Y  R  N  F  A  A  E  Q  Y  A  S  V  F  A  I  S  L  P  874

TACACCAACCCCTCCAAGTTTAATCAGTACATCGTGTGTCTGGCCCATCACGTCATAGCC 2700
 Y  T  N  P  S  K  F  N  Q  Y  I  V  C  L  A  H  H  V  I  A  894

ATGTGGTTCATCAGGTGCCGCCTGCCCTTCCGGAAGGATTTTGTCCCTTTCATCACTAAG 2760
 M  W  F  I  R  C  R  L  P  F  R  K  D  F  V  P  F  I  T  K  914

GGCCTGCGGTCCAATGTCCTCTTGTCTTTTGATGACACCCCCGAGAAGGACAGCTTCAGG 2820
 G  L  R  S  N  V  L  L  S  F  D  D  T  P  E  K  D  S  F  R  934

GCCCGGAGTACTAGTCTCAACGAGAGACCCAAGAGTCTGAGGATAGCCAGACCCCCCAAA 2880
 A  R  S  T  S  L  N  E  R  P  K  S  L  R  I  A  R  P  P  K  954

CAAGGCTTGAATAACTCTCCACCCGTGAAAGAATTCAAGGAGAGCTCTGCAGCCGAGGCC 2940
 Q  G  L  N  N  S  P  P  V  K  E  F  K  E  S  S  A  A  E  A  974

TTCCGGTGCCGCAGCATCAGTGTGTCTGAACATGTGGTCCGCAGCAGGATACAGACGTCC 3000
 F  R  C  R  S  I  S  V  S  E  H  V  V  R  S  R  I  Q  T  S  994

CTCACCAGTGCCAGCTTGGGGTCTGCAGATGAGAACTCCGTGGCCCAGGCTGACGATAGC 3060
 L  T  S  A  S  L  G  S  A  D  E  N  S  V  A  Q  A  D  D  S  1014

CTGAAAAACCTCCACCTGGAGCTCACGGAAACCTGTCTGGACATGATGGCTCGATACGTC 3120
 L  K  N  L  H  L  E  L  T  E  T  C  L  D  M  M  A  R  Y  V  1034

TTCTCCAACTTCACGGCTGTCCCGAAGAGGTCTCCTGTGGGCGAGTTCCTCCTAGCGGGT 3180
 F  S  N  F  T  A  V  P  K  R  S  P  V  G  E  F  L  L  A  G  1054
    @

GGCAGGACCAAAACCTGGCTGGTTGGGAACAAGCTTGTCACTGTGACGACAAGCGTGGGA 3240
 G  R  T  K  T  W  L  V  G  N  K  L  V  T  V  T  T  S  V  G  1074

ACCGGGACCCGGTCGTTACTAGGCCTGGACTCGGGGGAGCTGCAGTCCGGCCCGGAGTCG 3300
 T  G  T  R  S  L  L  G  L  D  S  G  E  L  Q  S  G  P  E  S  1094

AGCTCCAGCCCCGGGGTGCATGTGAGACAGACCAAGGAGGCGCCGGCCAAGCTGGAGTCC 3360
 S  S  S  P  G  V  H  V  R  Q  T  K  E  A  P  A  K  L  E  S  1114

CAGGCTGGGCAGCAGGTGTCCCGTGGGGCCCGGGATCGGGTCCGTTCCATGTCGGGGGGC 3420
 Q  A  G  Q  Q  V  S  R  G  A  R  D  R  V  R  S  M  S  G  G  1134
```

FIG. 3e

```
CATGGTCTTCGAGTTGGCGCCCTGGACGTGCCGGCCTCCCAGTTCCTGGGCAGTGCCACT 3480
 H  G  L  R  V  G  A  L  D  V  P  A  S  Q  F  L  G  S  A  T  1154

TCTCCAGGACCACGGACTGCACCAGCCGCGAAACCTGAGAAGGCCTCAGCTGGCACCCGG 3540
 S  P  G  P  R  T  A  P  A  A  K  P  E  K  A  S  A  G  T  R  1174

GTTCCTGTGCAGGAGAAGACGAACCTGGCGGCCTATGTGCCCCTGCTGACCCAGGGCTGG 3600
 V  P  V  Q  E  K  T  N  L  A  A  Y  V  P  L  L  T  Q  G  W  1194

GCGGAGATCCTGGTCCGGAGGCCCACAGGGAACACCAGCTGGCTGATGAGCCTGGAGAAC 3660
 A  E  I  L  V  R  R  P  T  G  N  T  S  W  L  M  S  L  E  N  1214
             ▲        @

CCGCTCAGCCCTTTCTCCTCGGACATCAACAACATGCCCCTGCAGGAGCTGTCTAACGCC 3720
 P  L  S  P  F  S  S  D  I  N  N  M  P  L  Q  E  L  S  N  A  1234

CTCATGGCGGCTGAGCGCTTCAAGGAGCACCGGGACACAGCCCTGTACAAGTCACTGTCG 3780
 L  M  A  A  E  R  F  K  E  H  R  D  T  A  L  Y  K  S  L  S  1254
                                                       #

GTGCCGGCAGCCAGCACGGCCAAACCCCCTCCTCTGCCTCGCTCCAACACAGACTCCGCC 3840
 V  P  A  A  S  T  A  K  P  P  P  L  P  R  S  N  T  D  S  A  1274
       ▼                             ►

GTGGTCATGGAGGAGGGAAGTCCGGGCGAGGTTCCTGTGCTGGTGGAGCCCCCAGGGTTG 3900
 V  V  M  E  E  G  S  P  G  E  V  P  V  L  V  E  P  P  G  L  1294
          ►

GAGGACGTTGAGGCAGCGCTAGGCATGGACAGGCGCACGGATGCCTACAGCAGGTCGTCC 3960
 E  D  V  E  A  A  L  G  M  D  R  R  T  D  A  Y  S  R  S  S  1314

TCAGTCTCCAGCCAGGAGGAGAAGTCGCTCCACGCGGAGGAGCTGGTTGGCAGGGGCATC 4020
 S  V  S  S  Q  E  E  K  S  L  H  A  E  E  L  V  G  R  G  I  1334
       ►  ►

CCCATCGAGCGAGTCGTCTCCTCGGAGGGTGGCCGGCCCTCTGTGGACCTCTCCTTCCAG 4080
 P  I  E  R  V  V  S  S  E  G  G  R  P  S  V  D  L  S  F  Q  1354

CCCTCGCAGCCCCTGAGCAAGTCCAGCTCCTCTCCCGAGCTGCAGACTCTGCAGGACATC 4140
 P  S  Q  P  L  S  K  S  S  S  S  P  E  L  Q  T  L  Q  D  I  1374
                   ►                    ►

CTCGGGGACCCTGGGGACAAGGCCGACGTGGGCCGGCTGAGCCCTGAGGTTAAGGCCCGG 4200
 L  G  D  P  G  D  K  A  D  V  G  R  L  S  P  E  V  K  A  R  1394

TCACAGTCAGGGACCCTGGACGGGGAAAGTGCTGCCTGGTCGGCCTCGGGCGAAGACAGT 4260
 S  Q  S  G  T  L  D  G  E  S  A  A  W  S  A  S  G  E  D  S  1414
                                     ►
```

FIG. 3f

```
CGGGGCCAGCCCGAGGGTCCCTTGCCTTCCAGCTCCCCCCGCTCGCCCAGTGGCCTCCGG 4320
  R  G  Q  P  E  G  P  L  P  S  S  S  P  R  S  P  S  G  L  R  1434

CCCCGAGGTTACACCATCTCCGACTCGGCCCCATCACGCAGGGGCAAGAGAGTAGAGAGG 4380
  P  R  G  Y  T  I  S  D  S  A  P  S  R  R  G  K  R  V  E  R  1454

GACGCCTTAAAGAGCAGAGCCACAGCCTCCAATGCAGAGAAAGTGCCAGGCATCAACCCC 4440
  D  A  L  K  S  R  A  T  A  S  N  A  E  K  V  P  G  I  N  P  1474

AGTTTCGTGTTCCTGCAGCTCTACCATTCCCCCTTCTTTGGCGACGAGTCAAACAAGCCA 4500
  S  F  V  F  L  Q  L  Y  H  S  P  F  F  G  D  E  S  N  K  P  1494

ATCCTGCTGCCCAATGAGTCACAGTCCTTTGAGCGGTCGGTGCAGCTCCTCGACCAGATC 4560
  I  L  L  P  N  E  S  Q  S  F  E  R  S  V  Q  L  L  D  Q  I  1514

CCATCATACGACACCCACAAGATCGCCGTCCTGTATGTTGGAGAAGGCCAGAGCAACAGC 4620
  P  S  Y  D  T  H  K  I  A  V  L  Y  V  G  E  G  Q  S  N  S  1534

GAGCTCGCCATCCTGTCCAATGAGCATGGCTCCTACAGGTACACGGAGTTCCTGACGGGC 4680
  E  L  A  I  L  S  N  E  H  G  S  Y  R  Y  T  E  F  L  T  G  1554

CTGGGCCGGCTCATCGAGCTGAAGGACTGCCAGCCGGACAAGGTGTACCTGGGAGGCCTG 4740
  L  G  R  L  I  E  L  K  D  C  Q  P  D  K  V  Y  L  G  G  L  1574

GACGTGTGTGGTGAGGACGGCCAGTTCACCTACTGCTGGCACGATGACATCATGCAAGCC 4800
  D  V  C  G  E  D  G  Q  F  T  Y  C  W  H  D  D  I  M  Q  A  1594

GTCTTCCACATCGCCACCCTGATGCCCACCAAGGACGTGGACAAGCACCGCTGCGACAAG 4860
  V  F  H  I  A  T  L  M  P  T  K  D  V  D  K  H  R  C  D  K  1614

AAGCGCCACCTGGGCAACGACTTTGTGTCCATTGTCTACAATGACTCCGGTGAGGACTTC 4920
  K  R  H  L  G  N  D  F  V  S  I  V  Y  N  D  S  G  E  D  F  1634

AAGCTTGGCACCATCAAGGGCCAGTTCAACTTTGTCCACGTGATCGTCACCCCGCTGGAC 4980
  K  L  G  T  I  K  G  Q  F  N  F  V  H  V  I  V  T  P  L  D  1654

TACGAGTGCAACCTGGTGTCCCTGCAGTGCAGGAAAGACATGGAGGGCCTTGTGGACACC 5040
  Y  E  C  N  L  V  S  L  Q  C  R  K  D  M  E  G  L  V  D  T  1674

AGCGTGGCCAAGATCGTGTCTGACCGCAACCTGCCCTTCGTGGCCCGCCAGATGGCCCTG 5100
  S  V  A  K  I  V  S  D  R  N  L  P  F  V  A  R  Q  M  A  L  1694
```

```
CACGCAAATATGGCCTCACAGGTGCATCATAGCCGCTCCAACCCCACCGATATCTACCCC  5160
 H  A  N  M  A  S  Q  V  H  H  S  R  S  N  P  T  D  I  Y  P   1714

TCCAAGTGGATTGCCCGGCTCCGCCACATCAAGCGGCTCCGCCAGCGGATCTGCGAGGAA  5220
 S  K  W  I  A  R  L  R  H  I  K  R  L  R  Q  R  I  C  E  E   1734

GCCGCCTACTCCAACCCCAGCCTACCTCTGGTGCACCCTCCGTCCCATAGCAAAGCCCCT  5280
 A  A  Y  S  N  P  S  L  P  L  V  H  P  P  S  H  S  K  A  P   1754
       #

GCACAGACTCCAGCCGAGCCCACACCTGGCTATGAGGTGGGCCAGCGGAAGCGCCTCATC  5340
 A  Q  T  P  A  E  P  T  P  G  Y  E  V  G  Q  R  K  R  L  I   1774
    ▸

TCCTCGGTGGAGGACTTCACCGAGTTTGTGTGAGGCCGGGGCCCTCCCTCCTGCACTGGC  5400
 S  S  V  E  D  F  T  E  F  V  *                               1784
 ▸  ▸

CTTGGACGGTATTGCCTGTCAGTGAAATAAATAAAGTCCTGACCCCAGTGCACAGACATA  5460

GAGGCACAGATTGC                                                  5474
```

FIG. 3g

SEQUENCE DESCRIPTION: SEQ ID NO: 1:  FIG. 3h

| | | | | | | | | | | | | | | | | |
|---|---|---|---|---|---|---|---|---|---|---|---|---|---|---|---|---|
| GGTGCGTCCT | GGTCCACC | ATG | GCC | AAA | CCA | ACA | AGC | AAA | GAT | TCA | GGC | TTG | | | | 51 |
| | | Met | Ala | Lys | Pro | Thr | Ser | Lys | Asp | Ser | Gly | Leu | | | | |
| | | 1 | | 5 | | | | | | | 10 | | | | | |
| AAG | GAG | AAG | TTT | AAG | ATT | CTG | TTG | GGA | CTG | GGA | ACA | CCG | AGG | CCA | AAT | 99 |
| Lys | Glu | Lys | Phe | Lys | Ile | Leu | Leu | Gly | Leu | Gly | Thr | Pro | Arg | Pro | Asn | |
| | | 15 | | | | | 20 | | | | | 25 | | | | |
| CCC | AGG | TCT | GCA | GAG | GGT | AAA | CAG | ACG | GAG | TTT | ATC | ATC | ACC | GCG | GAA | 147 |
| Pro | Arg | Ser | Ala | Glu | Gly | Lys | Gln | Thr | Glu | Phe | Ile | Ile | Thr | Ala | Glu | |
| | | 30 | | | | | 35 | | | | | 40 | | | | |
| ATA | CTG | AGA | GAA | CTG | AGC | ATG | GAA | TGT | GGC | CTC | AAC | AAT | CGC | ATC | CGG | 195 |
| Ile | Leu | Arg | Glu | Leu | Ser | Met | Glu | Cys | Gly | Leu | Asn | Asn | Arg | Ile | Arg | |
| | | 45 | | | | 50 | | | | | 55 | | | | | |
| ATG | ATA | GGG | CAG | ATT | TGT | GAA | GTC | GCA | AAA | ACC | AAG | AAA | TTT | GAA | GAG | 243 |
| Met | Ile | Gly | Gln | Ile | Cys | Glu | Val | Ala | Lys | Thr | Lys | Lys | Phe | Glu | Glu | |
| | 60 | | | | 65 | | | | | 70 | | | | | 75 | |
| CAC | GCA | GTG | GAA | GCA | CTC | TGG | AAG | GCG | GTC | GCG | GAT | CTG | TTG | CAG | CCG | 291 |
| His | Ala | Val | Glu | Ala | Leu | Trp | Lys | Ala | Val | Ala | Asp | Leu | Leu | Gln | Pro | |
| | | | | | 80 | | | | | 85 | | | | | 90 | |
| GAG | CGG | ACG | CTG | GAG | GCC | CGG | CAC | GCG | GTG | CTG | GCT | CTG | CTG | AAG | GCC | 339 |
| Glu | Arg | Thr | Leu | Glu | Ala | Arg | His | Ala | Val | Leu | Ala | Leu | Leu | Lys | Ala | |
| | | | 95 | | | | | 100 | | | | | 105 | | | |
| ATC | GTG | CAG | GGG | CAG | GGC | GAG | CGT | TTG | GGG | GTC | CTC | AGA | GCC | CTC | TTC | 387 |
| Ile | Val | Gln | Gly | Gln | Gly | Glu | Arg | Leu | Gly | Val | Leu | Arg | Ala | Leu | Phe | |
| | | 110 | | | | | 115 | | | | | 120 | | | | |
| TTT | AAG | GTC | ATC | AAG | GAT | TAC | CCT | TCC | AAC | GAA | GAC | CTT | CAC | GAA | AGG | 435 |
| Phe | Lys | Val | Ile | Lys | Asp | Tyr | Pro | Ser | Asn | Glu | Asp | Leu | His | Glu | Arg | |
| | | 125 | | | | 130 | | | | | 135 | | | | | |
| CTG | GAG | GTT | TTC | AAG | GCC | CTC | ACA | GAC | AAT | GGG | AGA | CAC | ATC | ACC | TAC | 483 |
| Leu | Glu | Val | Phe | Lys | Ala | Leu | Thr | Asp | Asn | Gly | Arg | His | Ile | Thr | Tyr | |
| 140 | | | | | 145 | | | | | 150 | | | | | 155 | |
| TTG | GAG | GAA | GAG | CTG | GCT | GAC | TTT | GTC | CTG | CAG | TGG | ATG | GAT | GTT | GGC | 531 |
| Leu | Glu | Glu | Glu | Leu | Ala | Asp | Phe | Val | Leu | Gln | Trp | Met | Asp | Val | Gly | |
| | | | | 160 | | | | | 165 | | | | | 170 | | |
| TTG | TCC | TCG | GAA | TTC | CTT | CTG | GTG | CTG | GTG | AAC | TTG | GTC | AAA | TTC | AAT | 579 |
| Leu | Ser | Ser | Glu | Phe | Leu | Leu | Val | Leu | Val | Asn | Leu | Val | Lys | Phe | Asn | |
| | | | 175 | | | | | 180 | | | | | 185 | | | |
| AGC | TGT | TAC | CTC | GAC | GAG | TAC | ATC | GCA | AGG | ATG | GTT | CAG | ATG | ATC | TGT | 627 |
| Ser | Cys | Tyr | Leu | Asp | Glu | Tyr | Ile | Ala | Arg | Met | Val | Gln | Met | Ile | Cys | |
| | | 190 | | | | | 195 | | | | | 200 | | | | |
| CTG | CTG | TGC | GTC | CGG | ACC | GCG | TCC | TCT | GTG | GAC | ATA | GAG | GTC | TCC | CTG | 675 |
| Leu | Leu | Cys | Val | Arg | Thr | Ala | Ser | Ser | Val | Asp | Ile | Glu | Val | Ser | Leu | |
| | | 205 | | | | 210 | | | | | 215 | | | | | |
| CAG | GTG | CTG | GAC | GCC | GTG | GTC | TGC | TAC | AAC | TGC | CTG | CCG | GCT | GAG | AGC | 723 |
| Gln | Val | Leu | Asp | Ala | Val | Val | Cys | Tyr | Asn | Cys | Leu | Pro | Ala | Glu | Ser | |
| 220 | | | | 225 | | | | | 230 | | | | | 235 | | |

FIG. 3i

| | |
|---|---|
| CTC CCG CTG TTC ATC GTT ACC CTC TGT CGC ACC ATC AAC GTC AAG GAG<br>Leu Pro Leu Phe Ile Val Thr Leu Cys Arg Thr Ile Asn Val Lys Glu<br>240                                            245                                  250 | 771 |
| CTC TGC GAG CCT TGC TGG AAG CTG ATG CGG AAC CTC CTT GGC ACC CAC<br>Leu Cys Glu Pro Cys Trp Lys Leu Met Arg Asn Leu Leu Gly Thr His<br>255                                    260                                 265 | 819 |
| CTG GGC CAC AGC GCC ATC TAC AAC ATG TGC CAC CTC ATG GAG GAC AGA<br>Leu Gly His Ser Ala Ile Tyr Asn Met Cys His Leu Met Glu Asp Arg<br>270                                    275                                 280 | 867 |
| GCC TAC ATG GAG GAC GCG CCC CTG CTG AGA GGA GCC GTG TTT TTT GTG<br>Ala Tyr Met Glu Asp Ala Pro Leu Leu Arg Gly Ala Val Phe Phe Val<br>285                                 290                                295 | 915 |
| GGC ATG GCT CTC TGG GGA GCC CAC CGG CTC TAT TCT CTC AGG AAC TCG<br>Gly Met Ala Leu Trp Gly Ala His Arg Leu Tyr Ser Leu Arg Asn Ser<br>300                                 305                               310                          315 | 963 |
| CCG ACA TCT GTG TTT CCA TCA TTT TAC CAG GCC ATG GCA TGT CCG AAC<br>Pro Thr Ser Val Phe Pro Ser Phe Tyr Gln Ala Met Ala Cys Pro Asn<br>320                                  325                               330 | 1011 |
| GAG GTG GTG TCC TAT GAG ATC GTC CTG TCC ATC ACC AGG CTC ATC AAG<br>Glu Val Val Ser Tyr Glu Ile Val Leu Ser Ile Thr Arg Leu Ile Lys<br>335                                 340                               345 | 1059 |
| AAG TAT AGG AAG GAG CTC CAG GTG GTG GCG TGG GAC ATT CTG CTG AAC<br>Lys Tyr Arg Lys Glu Leu Gln Val Val Ala Trp Asp Ile Leu Leu Asn<br>350                                 355                               360 | 1107 |
| ATC ATC GAA CGG CTC CTT CAA CAG CTC CAG ACC TTG GAC AGC CCG GAG<br>Ile Ile Glu Arg Leu Leu Gln Gln Leu Gln Thr Leu Asp Ser Pro Glu<br>365                                 370                               375 | 1155 |
| CTC AGG ACC ATC GTC CAT GAC CTG TTG ACC ACG GTG GAG GAG CTG TGT<br>Leu Arg Thr Ile Val His Asp Leu Leu Thr Thr Val Glu Glu Leu Cys<br>380                                 385                               390                          395 | 1203 |
| GAC CAG AAC GAG TTC CAC GGG TCT CAG GAG AGA TAC TTT GAA CTG GTG<br>Asp Gln Asn Glu Phe His Gly Ser Gln Glu Arg Tyr Phe Glu Leu Val<br>400                                 405                               410 | 1251 |
| GAG AGA TGT GCG GAC CAG AGG CCT GAG TCC TCC CTC CTG AAC CTG ATC<br>Glu Arg Cys Ala Asp Gln Arg Pro Glu Ser Ser Leu Leu Asn Leu Ile<br>415                                 420                               425 | 1299 |
| TCC TAT AGA GCG CAG TCC ATC CAC CCG GCC AAG GAC GGC TGG ATT CAG<br>Ser Tyr Arg Ala Gln Ser Ile His Pro Ala Lys Asp Gly Trp Ile Gln<br>430                                 435                               440 | 1347 |
| AAC CTG CAG GCG CTG ATG GAG AGA TTC TTC AGG AGC GAG TCC CGA GGC<br>Asn Leu Gln Ala Leu Met Glu Arg Phe Phe Arg Ser Glu Ser Arg Gly<br>445                                 450                               455 | 1395 |
| GCC GTG CGC ATC AAG GTG CTG GAC GTG CTG TCC TTT GTG CTG CTC ATC<br>Ala Val Arg Ile Lys Val Leu Asp Val Leu Ser Phe Val Leu Leu Ile<br>460                                 465                               470                          475 | 1443 |
| AAC AGG CAG TTC TAT GAG GAG GAG CTG ATT AAC TCA GTG GTC ATC TCG<br>Asn Arg Gln Phe Tyr Glu Glu Glu Leu Ile Asn Ser Val Val Ile Ser<br>480                                 485                               490 | 1491 |

FIG. 3j

```
CAG CTC TCC CAC ATC CCC GAG GAT AAA GAC CAC CAG GTC CGA AAG CTG        1539
Gln Leu Ser His Ile Pro Glu Asp Lys Asp His Gln Val Arg Lys Leu
            495             500             505

GCC ACC CAG TTG CTG GTG GAC CTG GCA GAG GGC TGC CAC ACA CAC CAC        1587
Ala Thr Gln Leu Leu Val Asp Leu Ala Glu Gly Cys His Thr His His
        510             515             520

TTC AAC AGC CTG CTG GAC ATC ATC GAG AAG GTG ATG GCC CGC TCC CTC        1635
Phe Asn Ser Leu Leu Asp Ile Ile Glu Lys Val Met Ala Arg Ser Leu
525             530             535

TCC CCA CCC CCG GAG CTG GAA GAA AGG GAT GTG GCC GCA TAC TCG GCC        1683
Ser Pro Pro Pro Glu Leu Glu Glu Arg Asp Val Ala Ala Tyr Ser Ala
540             545             550             555

TCC TTG GAG GAT GTG AAG ACA GCC GTC CTG GGG CTT CTG GTC ATC CTT        1731
Ser Leu Glu Asp Val Lys Thr Ala Val Leu Gly Leu Leu Val Ile Leu
            560             565             570

CAG ACC AAG CTG TAC ACC CTG CCT GCA AGC CAC GCC ACG CGT GTG TAT        1779
Gln Thr Lys Leu Tyr Thr Leu Pro Ala Ser His Ala Thr Arg Val Tyr
        575             580             585

GAG ATG CTG GTC AGC CAC ATT CAG CTC CAC TAC AAG CAC AGC TAC ACC        1827
Glu Met Leu Val Ser His Ile Gln Leu His Tyr Lys His Ser Tyr Thr
        590             595             600

CTG CCA ATC GCG AGC AGC ATC CGG CTG CAG GCC TTT GAC TTC CTG TTT        1875
Leu Pro Ile Ala Ser Ser Ile Arg Leu Gln Ala Phe Asp Phe Leu Phe
605             610             615

CTG CTG CGG GCC GAC TCA CTG CAC CGC CTG GGC CTG CCC AAC AAG GAT        1923
Leu Leu Arg Ala Asp Ser Leu His Arg Leu Gly Leu Pro Asn Lys Asp
620             625             630             635

GGA GTC GTG CGG TTC AGC CCC TAC TGC GTC TGC GAC TAC ATG GAG CCA        1971
Gly Val Val Arg Phe Ser Pro Tyr Cys Val Cys Asp Tyr Met Glu Pro
            640             645             650

GAG AGA GGC TCT GAG AAG AAG ACC AGC GGC CCC CTT TCT CCT CCC ACA        2019
Glu Arg Gly Ser Glu Lys Lys Thr Ser Gly Pro Leu Ser Pro Pro Thr
            655             660             665

GGG CCT CCT GGC CCG GCG CCT GCA GGC CCC GCC GTG CGG CTG GGG TCC        2067
Gly Pro Pro Gly Pro Ala Pro Ala Gly Pro Ala Val Arg Leu Gly Ser
        670             675             680

GTG CCC TAC TCC CTG CTC TTC CGC GTC CTG CTG CAG TGC TTG AAG CAG        2115
Val Pro Tyr Ser Leu Leu Phe Arg Val Leu Leu Gln Cys Leu Lys Gln
685             690             695

GAG TCT GAC TGG AAG GTG CTG AAG CTG GTT CTG GGC AGG CTG CCT GAG        2163
Glu Ser Asp Trp Lys Val Leu Lys Leu Val Leu Gly Arg Leu Pro Glu
700             705             710             715

TCC CTG CGC TAT AAA GTG CTC ATC TTT ACT TCC CCT TGC AGT GTG GAC        2211
Ser Leu Arg Tyr Lys Val Leu Ile Phe Thr Ser Pro Cys Ser Val Asp
            720             725             730

CAG CTG TGC TCT GCT CTC TGC TCC ATG CTT TCA GGC CCA AAG ACA CTG        2259
Gln Leu Cys Ser Ala Leu Cys Ser Met Leu Ser Gly Pro Lys Thr Leu
            735             740             745
```

FIG. 3k

| | | | | | | | | | | | | | | | | |
|---|---|---|---|---|---|---|---|---|---|---|---|---|---|---|---|---|
| GAG | CGG | CTC | CGA | GGC | GCC | CCA | GAA | GGC | TTC | TCC | AGA | ACT | GAC | TTG | CAC | 2307 |
| Glu | Arg | Leu | Arg | Gly | Ala | Pro | Glu | Gly | Phe | Ser | Arg | Thr | Asp | Leu | His | |
| | 750 | | | | | 755 | | | | | 760 | | | | | |
| CTG | GCC | GTG | GTT | CCA | GTG | CTG | ACA | GCA | TTA | ATC | TCT | TAC | CAT | AAC | TAC | 2355 |
| Leu | Ala | Val | Val | Pro | Val | Leu | Thr | Ala | Leu | Ile | Ser | Tyr | His | Asn | Tyr | |
| | 765 | | | | | 770 | | | | | 775 | | | | | |
| CTG | GAC | AAA | ACC | AAA | CAG | CGC | GAG | ATG | GTC | TAC | TGC | CTG | GAG | CAG | GGC | 2403 |
| Leu | Asp | Lys | Thr | Lys | Gln | Arg | Glu | Met | Val | Tyr | Cys | Leu | Glu | Gln | Gly | |
| 780 | | | | | 785 | | | | | 790 | | | | | 795 | |
| CTC | ATC | CAC | CGC | TGT | GCC | AGA | CAG | TGC | GTC | GTG | GCC | TTG | TCC | ATC | TGC | 2451 |
| Leu | Ile | His | Arg | Cys | Ala | Arg | Gln | Cys | Val | Val | Ala | Leu | Ser | Ile | Cys | |
| | | | 800 | | | | | 805 | | | | | 810 | | | |
| AGC | GTG | GAG | ATG | CCT | GAC | ATC | ATC | ATC | AAG | GCG | CTG | CCT | GTT | CTG | GTG | 2499 |
| Ser | Val | Glu | Met | Pro | Asp | Ile | Ile | Ile | Lys | Ala | Leu | Pro | Val | Leu | Val | |
| | | | 815 | | | | | 820 | | | | | 825 | | | |
| GTG | AAG | CTC | ACG | CAC | ATC | TCA | GCC | ACA | GCC | AGC | ATG | GCC | GTC | CCA | CTG | 2547 |
| Val | Lys | Leu | Thr | His | Ile | Ser | Ala | Thr | Ala | Ser | Met | Ala | Val | Pro | Leu | |
| | | 830 | | | | | 835 | | | | | 840 | | | | |
| CTG | GAG | TTC | CTG | TCC | ACT | CTG | GCC | AGG | CTG | CCG | CAC | CTC | TAC | AGG | AAC | 2595 |
| Leu | Glu | Phe | Leu | Ser | Thr | Leu | Ala | Arg | Leu | Pro | His | Leu | Tyr | Arg | Asn | |
| | 845 | | | | | 850 | | | | | 855 | | | | | |
| TTT | GCC | GCG | GAG | CAG | TAT | GCC | AGT | GTG | TTC | GCC | ATC | TCC | CTG | CCG | TAC | 2643 |
| Phe | Ala | Ala | Glu | Gln | Tyr | Ala | Ser | Val | Phe | Ala | Ile | Ser | Leu | Pro | Tyr | |
| 860 | | | | | 865 | | | | | 870 | | | | | 875 | |
| ACC | AAC | CCC | TCC | AAG | TTT | AAT | CAG | TAC | ATC | GTG | TGT | CTG | GCC | CAT | CAC | 2691 |
| Thr | Asn | Pro | Ser | Lys | Phe | Asn | Gln | Tyr | Ile | Val | Cys | Leu | Ala | His | His | |
| | | | 880 | | | | | 885 | | | | | 890 | | | |
| GTC | ATA | GCC | ATG | TGG | TTC | ATC | AGG | TGC | CGC | CTG | CCC | TTC | CGG | AAG | GAT | 2739 |
| Val | Ile | Ala | Met | Trp | Phe | Ile | Arg | Cys | Arg | Leu | Pro | Phe | Arg | Lys | Asp | |
| | | | 895 | | | | | 900 | | | | | 905 | | | |
| TTT | GTC | CCT | TTC | ATC | ACT | AAG | GGC | CTG | CGG | TCC | AAT | GTC | CTC | TTG | TCT | 2787 |
| Phe | Val | Pro | Phe | Ile | Thr | Lys | Gly | Leu | Arg | Ser | Asn | Val | Leu | Leu | Ser | |
| | | 910 | | | | | 915 | | | | | 920 | | | | |
| TTT | GAT | GAC | ACC | CCC | GAG | AAG | GAC | AGC | TTC | AGG | GCC | CGG | AGT | ACT | AGT | 2835 |
| Phe | Asp | Asp | Thr | Pro | Glu | Lys | Asp | Ser | Phe | Arg | Ala | Arg | Ser | Thr | Ser | |
| | 925 | | | | | 930 | | | | | 935 | | | | | |
| CTC | AAC | GAG | AGA | CCC | AAG | AGT | CTG | AGG | ATA | GCC | AGA | CCC | CCC | AAA | CAA | 2883 |
| Leu | Asn | Glu | Arg | Pro | Lys | Ser | Leu | Arg | Ile | Ala | Arg | Pro | Pro | Lys | Gln | |
| 940 | | | | | 945 | | | | | 950 | | | | | 955 | |
| GGC | TTG | AAT | AAC | TCT | CCA | CCC | GTG | AAA | GAA | TTC | AAG | GAG | AGC | TCT | GCA | 2931 |
| Gly | Leu | Asn | Asn | Ser | Pro | Pro | Val | Lys | Glu | Phe | Lys | Glu | Ser | Ser | Ala | |
| | | | | 960 | | | | | 965 | | | | | 970 | | |
| GCC | GAG | GCC | TTC | CGG | TGC | CGC | AGC | ATC | AGT | GTG | TCT | GAA | CAT | GTG | GTC | 2979 |
| Ala | Glu | Ala | Phe | Arg | Cys | Arg | Ser | Ile | Ser | Val | Ser | Glu | His | Val | Val | |
| | | | 975 | | | | | 980 | | | | | 985 | | | |
| CGC | AGC | AGG | ATA | CAG | ACG | TCC | CTC | ACC | AGT | GCC | AGC | TTG | GGG | TCT | GCA | 3027 |
| Arg | Ser | Arg | Ile | Gln | Thr | Ser | Leu | Thr | Ser | Ala | Ser | Leu | Gly | Ser | Ala | |
| | | 990 | | | | | 995 | | | | | 1000 | | | | |

FIG. 3I

| | |
|---|---|
| GAT GAG AAC TCC GTG GCC CAG GCT GAC GAT AGC CTG AAA AAC CTC CAC<br>Asp Glu Asn Ser Val Ala Gln Ala Asp Asp Ser Leu Lys Asn Leu His<br>1005               1010              1015 | 3075 |
| CTG GAG CTC ACG GAA ACC TGT CTG GAC ATG ATG GCT CGA TAC GTC TTC<br>Leu Glu Leu Thr Glu Thr Cys Leu Asp Met Met Ala Arg Tyr Val Phe<br>1020          1025           1030          1035 | 3123 |
| TCC AAC TTC ACG GCT GTC CCG AAG AGG TCT CCT GTG GGC GAG TTC CTC<br>Ser Asn Phe Thr Ala Val Pro Lys Arg Ser Pro Val Gly Glu Phe Leu<br>1040              1045          1050 | 3171 |
| CTA GCG GGT GGC AGG ACC AAA ACC TGG CTG GTT GGG AAC AAG CTT GTC<br>Leu Ala Gly Gly Arg Thr Lys Thr Trp Leu Val Gly Asn Lys Leu Val<br>         1055            1060          1065 | 3219 |
| ACT GTG ACG ACA AGC GTG GGA ACC GGG ACC CGG TCG TTA CTA GGC CTG<br>Thr Val Thr Thr Ser Val Gly Thr Gly Thr Arg Ser Leu Leu Gly Leu<br>      1070           1075          1080 | 3267 |
| GAC TCG GGG GAG CTG CAG TCC GGC CCG GAG TCG AGC TCC AGC CCC GGG<br>Asp Ser Gly Glu Leu Gln Ser Gly Pro Glu Ser Ser Ser Ser Pro Gly<br>1085             1090          1095 | 3315 |
| GTG CAT GTG AGA CAG ACC AAG GAG GCG CCG GCC AAG CTG GAG TCC CAG<br>Val His Val Arg Gln Thr Lys Glu Ala Pro Ala Lys Leu Glu Ser Gln<br>1100            1105          1110         1115 | 3363 |
| GCT GGG CAG CAG GTG TCC CGT GGG GCC CGG GAT CGG GTC CGT TCC ATG<br>Ala Gly Gln Gln Val Ser Arg Gly Ala Arg Asp Arg Val Arg Ser Met<br>          1120           1125         1130 | 3411 |
| TCG GGG GGC CAT GGT CTT CGA GTT GGC GCC CTG GAC GTG CCG GCC TCC<br>Ser Gly Gly His Gly Leu Arg Val Gly Ala Leu Asp Val Pro Ala Ser<br>      1135           1140          1145 | 3459 |
| CAG TTC CTG GGC AGT GCC ACT TCT CCA GGA CCA CGG ACT GCA CCA GCC<br>Gln Phe Leu Gly Ser Ala Thr Ser Pro Gly Pro Arg Thr Ala Pro Ala<br>1150               1155          1160 | 3507 |
| GCG AAA CCT GAG AAG GCC TCA GCT GGC ACC CGG GTT CCT GTG CAG GAG<br>Ala Lys Pro Glu Lys Ala Ser Ala Gly Thr Arg Val Pro Val Gln Glu<br>1165             1170          1175 | 3555 |
| AAG ACG AAC CTG GCG GCC TAT GTG CCC CTG CTG ACC CAG GGC TGG GCG<br>Lys Thr Asn Leu Ala Ala Tyr Val Pro Leu Leu Thr Gln Gly Trp Ala<br>1180            1185          1190         1195 | 3603 |
| GAG ATC CTG GTC CGG AGG CCC ACA GGG AAC ACC AGC TGG CTG ATG AGC<br>Glu Ile Leu Val Arg Arg Pro Thr Gly Asn Thr Ser Trp Leu Met Ser<br>          1200           1205         1210 | 3651 |
| CTG GAG AAC CCG CTC AGC CCT TTC TCC TCG GAC ATC AAC AAC ATG CCC<br>Leu Glu Asn Pro Leu Ser Pro Phe Ser Ser Asp Ile Asn Asn Met Pro<br>      1215           1220          1225 | 3699 |
| CTG CAG GAG CTG TCT AAC GCC CTC ATG GCG GCT GAG CGC TTC AAG GAG<br>Leu Gln Glu Leu Ser Asn Ala Leu Met Ala Ala Glu Arg Phe Lys Glu<br>      1230           1235          1240 | 3747 |
| CAC CGG GAC ACA GCC CTG TAC AAG TCA CTG TCG GTG CCG GCA GCC AGC<br>His Arg Asp Thr Ala Leu Tyr Lys Ser Leu Ser Val Pro Ala Ala Ser<br>1245             1250          1255 | 3795 |

FIG. 3m

```
ACG GCC AAA CCC CCT CCT CTG CCT CGC TCC AAC ACA GAC TCC GCC GTG        3843
Thr Ala Lys Pro Pro Pro Leu Pro Arg Ser Asn Thr Asp Ser Ala Val
1260            1265                1270                1275

GTC ATG GAG GAG GGA AGT CCG GGC GAG GTT CCT GTG CTG GTG GAG CCC        3891
Val Met Glu Glu Gly Ser Pro Gly Glu Val Pro Val Leu Val Glu Pro
            1280                1285                1290

CCA GGG TTG GAG GAC GTT GAG GCA GCG CTA GGC ATG GAC AGG CGC ACG        3939
Pro Gly Leu Glu Asp Val Glu Ala Ala Leu Gly Met Asp Arg Arg Thr
        1295                1300                1305

GAT GCC TAC AGC AGG TCG TCC TCA GTC TCC AGC CAG GAG GAG AAG TCG        3987
Asp Ala Tyr Ser Arg Ser Ser Ser Val Ser Ser Gln Glu Glu Lys Ser
    1310                1315                1320

CTC CAC GCG GAG GAG CTG GTT GGC AGG GGC ATC CCC ATC GAG CGA GTC        4035
Leu His Ala Glu Glu Leu Val Gly Arg Gly Ile Pro Ile Glu Arg Val
1325                1330                1335

GTC TCC TCG GAG GGT GGC CGG CCC TCT GTG GAC CTC TCC TTC CAG CCC        4083
Val Ser Ser Glu Gly Gly Arg Pro Ser Val Asp Leu Ser Phe Gln Pro
1340            1345                1350                1355

TCG CAG CCC CTG AGC AAG TCC AGC TCC TCT CCC GAG CTG CAG ACT CTG        4131
Ser Gln Pro Leu Ser Lys Ser Ser Ser Pro Glu Leu Gln Thr Leu
            1360                1365                1370

CAG GAC ATC CTC GGG GAC CCT GGG GAC AAG GCC GAC GTG GGC CGG CTG        4179
Gln Asp Ile Leu Gly Asp Pro Gly Asp Lys Ala Asp Val Gly Arg Leu
        1375                1380                1385

AGC CCT GAG GTT AAG GCC CGG TCA CAG TCA GGG ACC CTG GAC GGG GAA        4227
Ser Pro Glu Val Lys Ala Arg Ser Gln Ser Gly Thr Leu Asp Gly Glu
    1390                1395                1400

AGT GCT GCC TGG TCG GCC TCG GGC GAA GAC AGT CGG GGC CAG CCC GAG        4275
Ser Ala Ala Trp Ser Ala Ser Gly Glu Asp Ser Arg Gly Gln Pro Glu
1405                1410                1415

GGT CCC TTG CCT TCC AGC TCC CCC CGC TCG CCC AGT GGC CTC CGG CCC        4323
Gly Pro Leu Pro Ser Ser Ser Pro Arg Ser Pro Ser Gly Leu Arg Pro
1420            1425                1430                1435

CGA GGT TAC ACC ATC TCC GAC TCG GCC CCA TCA CGC AGG GGC AAG AGA        4371
Arg Gly Tyr Thr Ile Ser Asp Ser Ala Pro Ser Arg Arg Gly Lys Arg
            1440                1445                1450

GTA GAG AGG GAC GCC TTA AAG AGC AGA GCC ACA GCC TCC AAT GCA GAG        4419
Val Glu Arg Asp Ala Leu Lys Ser Arg Ala Thr Ala Ser Asn Ala Glu
        1455                1460                1465

AAA GTG CCA GGC ATC AAC CCC AGT TTC GTG TTC CTG CAG CTC TAC CAT        4467
Lys Val Pro Gly Ile Asn Pro Ser Phe Val Phe Leu Gln Leu Tyr His
    1470                1475                1480

TCC CCC TTC TTT GGC GAC GAG TCA AAC AAG CCA ATC CTG CTG CCC AAT        4515
Ser Pro Phe Phe Gly Asp Glu Ser Asn Lys Pro Ile Leu Leu Pro Asn
1485                1490                1495

GAG TCA CAG TCC TTT GAG CGG TCG GTG CAG CTC CTC GAC CAG ATC CCA        4563
Glu Ser Gln Ser Phe Glu Arg Ser Val Gln Leu Leu Asp Gln Ile Pro
1500            1505                1510                1515
```

FIG. 3n

```
TCA TAC GAC ACC CAC AAG ATC GCC GTC CTG TAT GTT GGA GAA GGC CAG    4611
Ser Tyr Asp Thr His Lys Ile Ala Val Leu Tyr Val Gly Glu Gly Gln
            1520            1525            1530

AGC AAC AGC GAG CTC GCC ATC CTG TCC AAT GAG CAT GGC TCC TAC AGG    4659
Ser Asn Ser Glu Leu Ala Ile Leu Ser Asn Glu His Gly Ser Tyr Arg
            1535            1540            1545

TAC ACG GAG TTC CTG ACG GGC CTG GGC CGG CTC ATC GAG CTG AAG GAC    4707
Tyr Thr Glu Phe Leu Thr Gly Leu Gly Arg Leu Ile Glu Leu Lys Asp
            1550            1555            1560

TGC CAG CCG GAC AAG GTG TAC CTG GGA GGC CTG GAC GTG TGT GGT GAG    4755
Cys Gln Pro Asp Lys Val Tyr Leu Gly Gly Leu Asp Val Cys Gly Glu
            1565            1570            1575

GAC GGC CAG TTC ACC TAC TGC TGG CAC GAT GAC ATC ATG CAA GCC GTC    4803
Asp Gly Gln Phe Thr Tyr Cys Trp His Asp Asp Ile Met Gln Ala Val
1580            1585            1590            1595

TTC CAC ATC GCC ACC CTG ATG CCC ACC AAG GAC GTG GAC AAG CAC CGC    4851
Phe His Ile Ala Thr Leu Met Pro Thr Lys Asp Val Asp Lys His Arg
            1600            1605            1610

TGC GAC AAG AAG CGC CAC CTG GGC AAC GAC TTT GTG TCC ATT GTC TAC    4899
Cys Asp Lys Lys Arg His Leu Gly Asn Asp Phe Val Ser Ile Val Tyr
            1615            1620            1625

AAT GAC TCC GGT GAG GAC TTC AAG CTT GGC ACC ATC AAG GGC CAG TTC    4947
Asn Asp Ser Gly Glu Asp Phe Lys Leu Gly Thr Ile Lys Gly Gln Phe
            1630            1635            1640

AAC TTT GTC CAC GTG ATC GTC ACC CCG CTG GAC TAC GAG TGC AAC CTG    4995
Asn Phe Val His Val Ile Val Thr Pro Leu Asp Tyr Glu Cys Asn Leu
            1645            1650            1655

GTG TCC CTG CAG TGC AGG AAA GAC ATG GAG GGC CTT GTG GAC ACC AGC    5043
Val Ser Leu Gln Cys Arg Lys Asp Met Glu Gly Leu Val Asp Thr Ser
1660            1665            1670            1675

GTG GCC AAG ATC GTG TCT GAC CGC AAC CTG CCC TTC GTG GCC CGC CAG    5091
Val Ala Lys Ile Val Ser Asp Arg Asn Leu Pro Phe Val Ala Arg Gln
            1680            1685            1690

ATG GCC CTG CAC GCA AAT ATG GCC TCA CAG GTG CAT CAT AGC CGC TCC    5139
Met Ala Leu His Ala Asn Met Ala Ser Gln Val His His Ser Arg Ser
            1695            1700            1705

AAC CCC ACC GAT ATC TAC CCC TCC AAG TGG ATT GCC CGG CTC CGC CAC    5187
Asn Pro Thr Asp Ile Tyr Pro Ser Lys Trp Ile Ala Arg Leu Arg His
            1710            1715            1720

ATC AAG CGG CTC CGC CAG CGG ATC TGC GAG GAA GCC GCC TAC TCC AAC    5235
Ile Lys Arg Leu Arg Gln Arg Ile Cys Glu Glu Ala Ala Tyr Ser Asn
            1725            1730            1735

CCC AGC CTA CCT CTG GTG CAC CCT CCG TCC CAT AGC AAA GCC CCT GCA    5283
Pro Ser Leu Pro Leu Val His Pro Pro Ser His Ser Lys Ala Pro Ala
1740            1745            1750            1755

CAG ACT CCA GCC GAG CCC ACA CCT GGC TAT GAG GTG GGC CAG CGG AAG    5331
Gln Thr Pro Ala Glu Pro Thr Pro Gly Tyr Glu Val Gly Gln Arg Lys
            1760            1765            1770
```

FIG. 3o

```
CGC CTC ATC TCC TCG GTG GAG GAC TTC ACC GAG TTT GTG TGAGGCCGGG     5380
Arg Leu Ile Ser Ser Val Glu Asp Phe Thr Glu Phe Val
        1775                    1780

GCCCTCCCTC CTGCACTGGC CTTGGACGGT ATTGCCTGTC AGTGAAATAA ATAAAGTCCT  5440

GACCCCAGTG CACAGACATA GAGGCACAGA TTGC                              5474
```

MOLECULE TYPE: protein
SEQUENCE DESCRIPTION: SEQ ID NO: 2:

```
Met Ala Lys Pro Thr Ser Lys Asp Ser Gly Leu Lys Glu Lys Phe Lys
 1               5                  10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Thr Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270
```

FIG. 3p

Ile Tyr Asn Met Cys His Leu Met Glu Asp Arg Ala Tyr Met Glu Asp
            275                 280                 285

Ala Pro Leu Leu Arg Gly Ala Val Phe Phe Val Gly Met Ala Leu Trp
    290                 295                 300

Gly Ala His Arg Leu Tyr Ser Leu Arg Asn Ser Pro Thr Ser Val Phe
305                 310                 315                 320

Pro Ser Phe Tyr Gln Ala Met Ala Cys Pro Asn Glu Val Val Ser Tyr
            325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
            405                 410                 415

Gln Arg Pro Glu Ser Ser Leu Leu Asn Leu Ile Ser Tyr Arg Ala Gln
                420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
    450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
            485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Pro Glu
    530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
            565                 570                 575

Thr Leu Pro Ala Ser His Ala Thr Arg Val Tyr Glu Met Leu Val Ser
            580                 585                 590

His Ile Gln Leu His Tyr Lys His Ser Tyr Thr Leu Pro Ile Ala Ser
    595                 600                 605

FIG. 3q

Ser Ile Arg Leu Gln Ala Phe Asp Phe Leu Phe Leu Leu Arg Ala Asp
610                       615                620

Ser Leu His Arg Leu Gly Leu Pro Asn Lys Asp Gly Val Val Arg Phe
625              630              635                     640

Ser Pro Tyr Cys Val Cys Asp Tyr Met Glu Pro Glu Arg Gly Ser Glu
            645              650                    655

Lys Lys Thr Ser Gly Pro Leu Ser Pro Pro Thr Gly Pro Pro Gly Pro
            660              665              670

Ala Pro Ala Gly Pro Ala Val Arg Leu Gly Ser Val Pro Tyr Ser Leu
        675              680              685

Leu Phe Arg Val Leu Leu Gln Cys Leu Lys Gln Glu Ser Asp Trp Lys
        690              695              700

Val Leu Lys Leu Val Leu Gly Arg Leu Pro Glu Ser Leu Arg Tyr Lys
705              710              715                     720

Val Leu Ile Phe Thr Ser Pro Cys Ser Val Asp Gln Leu Cys Ser Ala
            725              730              735

Leu Cys Ser Met Leu Ser Gly Pro Lys Thr Leu Glu Arg Leu Arg Gly
            740              745              750

Ala Pro Glu Gly Phe Ser Arg Thr Asp Leu His Leu Ala Val Val Pro
            755              760              765

Val Leu Thr Ala Leu Ile Ser Tyr His Asn Tyr Leu Asp Lys Thr Lys
770              775              780

Gln Arg Glu Met Val Tyr Cys Leu Glu Gln Gly Leu Ile His Arg Cys
785              790              795                     800

Ala Arg Gln Cys Val Val Ala Leu Ser Ile Cys Ser Val Glu Met Pro
            805              810              815

Asp Ile Ile Ile Lys Ala Leu Pro Val Leu Val Val Lys Leu Thr His
            820              825              830

Ile Ser Ala Thr Ala Ser Met Ala Val Pro Leu Leu Glu Phe Leu Ser
        835              840              845

Thr Leu Ala Arg Leu Pro His Leu Tyr Arg Asn Phe Ala Ala Glu Gln
        850              855              860

Tyr Ala Ser Val Phe Ala Ile Ser Leu Pro Tyr Thr Asn Pro Ser Lys
865              870              875                     880

Phe Asn Gln Tyr Ile Val Cys Leu Ala His His Val Ile Ala Met Trp
            885              890              895

Phe Ile Arg Cys Arg Leu Pro Phe Arg Lys Asp Phe Val Pro Phe Ile
            900              905              910

Thr Lys Gly Leu Arg Ser Asn Val Leu Leu Ser Phe Asp Asp Thr Pro
        915              920              925

Glu Lys Asp Ser Phe Arg Ala Arg Ser Thr Ser Leu Asn Glu Arg Pro
930              935              940

FIG. 3r

Lys Ser Leu Arg Ile Ala Arg Pro Pro Lys Gln Gly Leu Asn Asn Ser
945                950                 955                 960

Pro Pro Val Lys Glu Phe Lys Glu Ser Ser Ala Ala Glu Ala Phe Arg
            965                 970                 975

Cys Arg Ser Ile Ser Val Ser Glu His Val Val Arg Ser Arg Ile Gln
            980                 985                 990

Thr Ser Leu Thr Ser Ala Ser Leu Gly Ser Ala Asp Glu Asn Ser Val
            995                1000                1005

Ala Gln Ala Asp Asp Ser Leu Lys Asn Leu His Leu Glu Leu Thr Glu
1010                1015                1020

Thr Cys Leu Asp Met Met Ala Arg Tyr Val Phe Ser Asn Phe Thr Ala
1025                1030                1035                1040

Val Pro Lys Arg Ser Pro Val Gly Glu Phe Leu Leu Ala Gly Gly Arg
            1045                1050                1055

Thr Lys Thr Trp Leu Val Gly Asn Lys Leu Val Thr Val Thr Thr Ser
            1060                1065                1070

Val Gly Thr Gly Thr Arg Ser Leu Leu Gly Leu Asp Ser Gly Glu Leu
            1075                1080                1085

Gln Ser Gly Pro Glu Ser Ser Ser Pro Gly Val His Val Arg Gln
1090                1095                1100

Thr Lys Glu Ala Pro Ala Lys Leu Glu Ser Gln Ala Gly Gln Gln Val
1105                1110                1115                1120

Ser Arg Gly Ala Arg Asp Arg Val Arg Ser Met Ser Gly Gly His Gly
            1125                1130                1135

Leu Arg Val Gly Ala Leu Asp Val Pro Ala Ser Gln Phe Leu Gly Ser
            1140                1145                1150

Ala Thr Ser Pro Gly Pro Arg Thr Ala Pro Ala Ala Lys Pro Glu Lys
            1155                1160                1165

Ala Ser Ala Gly Thr Arg Val Pro Val Gln Glu Lys Thr Asn Leu Ala
1170                1175                1180

Ala Tyr Val Pro Leu Leu Thr Gln Gly Trp Ala Glu Ile Leu Val Arg
1185                1190                1195                1200

Arg Pro Thr Gly Asn Thr Ser Trp Leu Met Ser Leu Glu Asn Pro Leu
            1205                1210                1215

Ser Pro Phe Ser Ser Asp Ile Asn Asn Met Pro Leu Gln Glu Leu Ser
            1220                1225                1230

Asn Ala Leu Met Ala Ala Glu Arg Phe Lys Glu His Arg Asp Thr Ala
            1235                1240                1245

Leu Tyr Lys Ser Leu Ser Val Pro Ala Ala Ser Thr Ala Lys Pro Pro
            1250                1255                1260

Pro Leu Pro Arg Ser Asn Thr Asp Ser Ala Val Val Met Glu Glu Gly
1265                1270                1275                1280

FIG. 3s

Ser Pro Gly Glu Val Pro Val Leu Val Glu Pro Pro Gly Leu Glu Asp
           1285                   1290                1295

Val Glu Ala Ala Leu Gly Met Asp Arg Arg Thr Asp Ala Tyr Ser Arg
        1300               1305                1310

Ser Ser Ser Val Ser Ser Gln Glu Glu Lys Ser Leu His Ala Glu Glu
    1315                1320               1325

Leu Val Gly Arg Gly Ile Pro Ile Glu Arg Val Val Ser Ser Glu Gly
    1330                1335              1340

Gly Arg Pro Ser Val Asp Leu Ser Phe Gln Pro Ser Gln Pro Leu Ser
1345             1350              1355              1360

Lys Ser Ser Ser Ser Pro Glu Leu Gln Thr Leu Gln Asp Ile Leu Gly
         1365              1370             1375

Asp Pro Gly Asp Lys Ala Asp Val Gly Arg Leu Ser Pro Glu Val Lys
        1380               1385               1390

Ala Arg Ser Gln Ser Gly Thr Leu Asp Gly Glu Ser Ala Ala Trp Ser
     1395               1400              1405

Ala Ser Gly Glu Asp Ser Arg Gly Gln Pro Glu Gly Pro Leu Pro Ser
    1410               1415              1420

Ser Ser Pro Arg Ser Pro Ser Gly Leu Arg Pro Arg Gly Tyr Thr Ile
1425             1430              1435              1440

Ser Asp Ser Ala Pro Ser Arg Arg Gly Lys Arg Val Glu Arg Asp Ala
       1445               1450              1455

Leu Lys Ser Arg Ala Thr Ala Ser Asn Ala Glu Lys Val Pro Gly Ile
        1460               1465               1470

Asn Pro Ser Phe Val Phe Leu Gln Leu Tyr His Ser Pro Phe Phe Gly
      1475               1480              1485

Asp Glu Ser Asn Lys Pro Ile Leu Leu Pro Asn Glu Ser Gln Ser Phe
    1490               1495              1500

Glu Arg Ser Val Gln Leu Leu Asp Gln Ile Pro Ser Tyr Asp Thr His
1505             1510              1515              1520

Lys Ile Ala Val Leu Tyr Val Gly Glu Gly Gln Ser Asn Ser Glu Leu
         1525             1530              1535

Ala Ile Leu Ser Asn Glu His Gly Ser Tyr Arg Tyr Thr Glu Phe Leu
        1540               1545              1550

Thr Gly Leu Gly Arg Leu Ile Glu Leu Lys Asp Cys Gln Pro Asp Lys
       1555               1560              1565

Val Tyr Leu Gly Gly Leu Asp Val Cys Gly Glu Asp Gly Gln Phe Thr
    1570               1575              1580

Tyr Cys Trp His Asp Asp Ile Met Gln Ala Val Phe His Ile Ala Thr
1585             1590              1595              1600

Leu Met Pro Thr Lys Asp Val Asp Lys His Arg Cys Asp Lys Lys Arg
         1605             1610              1615

His Leu Gly Asn Asp Phe Val Ser Ile Val Tyr Asn Asp Ser Gly Glu
          1620            1625            1630

Asp Phe Lys Leu Gly Thr Ile Lys Gly Gln Phe Asn Phe Val His Val
          1635            1640            1645

Ile Val Thr Pro Leu Asp Tyr Glu Cys Asn Leu Val Ser Leu Gln Cys
    1650            1655            1660

Arg Lys Asp Met Glu Gly Leu Val Asp Thr Ser Val Ala Lys Ile Val
1665            1670            1675            1680

Ser Asp Arg Asn Leu Pro Phe Val Ala Arg Gln Met Ala Leu His Ala
              1685            1690            1695

Asn Met Ala Ser Gln Val His His Ser Arg Ser Asn Pro Thr Asp Ile
          1700            1705            1710

Tyr Pro Ser Lys Trp Ile Ala Arg Leu Arg His Ile Lys Arg Leu Arg
          1715            1720            1725

Gln Arg Ile Cys Glu Glu Ala Ala Tyr Ser Asn Pro Ser Leu Pro Leu
    1730            1735            1740

Val His Pro Pro Ser His Ser Lys Ala Pro Ala Gln Thr Pro Ala Glu
1745            1750            1755            1760

Pro Thr Pro Gly Tyr Glu Val Gly Gln Arg Lys Arg Leu Ile Ser Ser
              1765            1770            1775

Val Glu Asp Phe Thr Glu Phe Val
              1780

FIG. 3t

```
tuberin        Q A V F H I A T L M P T K D V D K H R C D K K R H L G N D F V S I V Y N D S G
GAP3 (human)  E I M F H V S T K L P Y T E G D A Q Q L Q R K R H I G N D I V A V V F Q D E N
Murine GAP    E I M F H V S T M L P Y T P N N Q Q L L R K R H I G N D I V T I V F Q E P G
```

FIG. 4

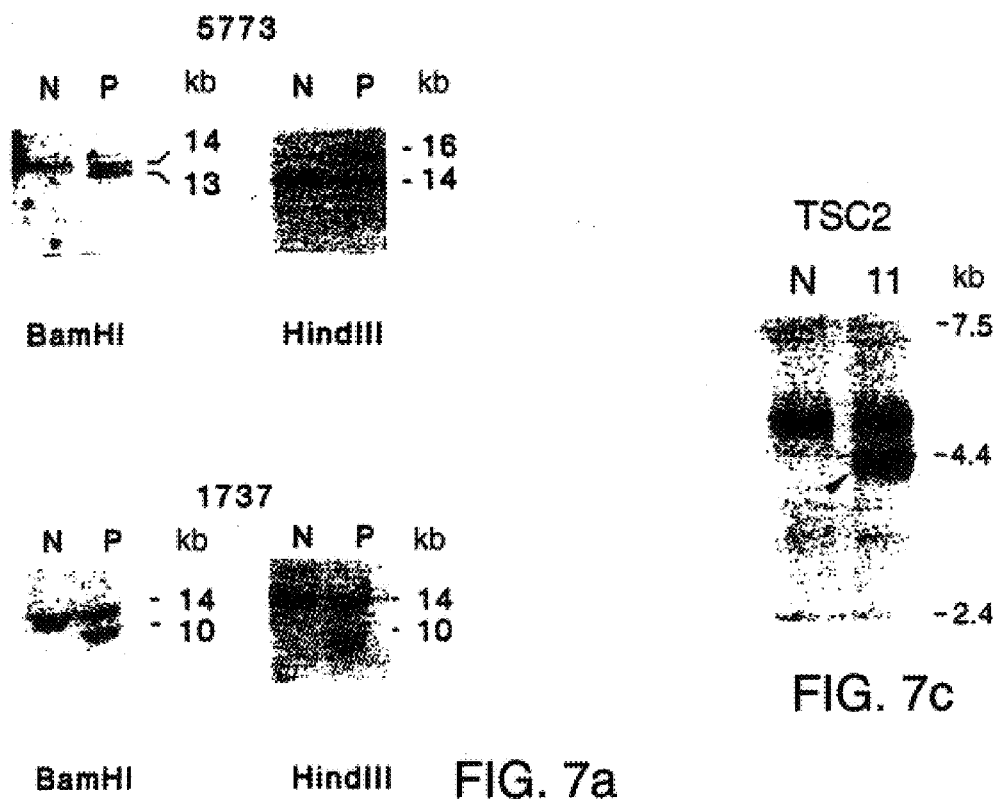
FIG. 7a
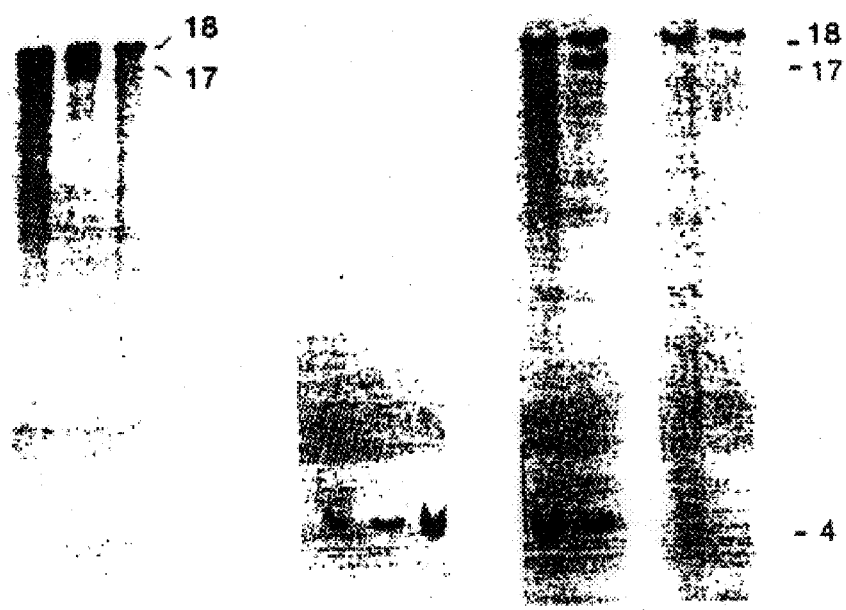
FIG. 7c
FIG. 7b

SEQUENCE LISTING (1) GENERAL INFORMATION:

(iii) NUMBER OF SEQUENCES:4

(2) INFORMATION FOR SEQ ID NO: 1:

(i) SEQUENCE CHARACTERISTICS:
      (A) LENGTH: 5474 base pairs
      (B) TYPE: nucleic acid
      (C) STRANDEDNESS: unknown
      (D) TOPOLOGY: unknown (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION:19..5370

(ix) FEATURE:
      (A) NAME/KEY: misc_feature
      (B) LOCATION:4795..4909

```
            (D) OTHER INFORMATION:/function= "GAP3 related domain"

(ix) FEATURE:
            (A) NAME/KEY: misc_feature
            (B) LOCATION:526..576
            (D) OTHER INFORMATION:/function= "Possible membrane
                spanning region"

(ix) FEATURE:
            (A) NAME/KEY: misc_feature
            (B) LOCATION:1393..1446
            (D) OTHER INFORMATION:/function= "Possible membrane
                spanning region"

(ix) FEATURE:
            (A) NAME/KEY: misc_feature
            (B) LOCATION:1681..1731
            (D) OTHER INFORMATION:/function= "Possible membrane
                spanning region"

(ix) FEATURE:
            (A) NAME/KEY: misc_feature
            (B) LOCATION:2428..2481
            (D) OTHER INFORMATION:/function= "Possible membrane
                spanning region"

(ix) FEATURE:
            (A) NAME/KEY: misc_feature
            (B) LOCATION:259..324
            (D) OTHER INFORMATION:/function= "Potential leucine
                zipper"

(ix) FEATURE:
            (A) NAME/KEY: repeat_region
            (B) LOCATION:313..339
            (D) OTHER INFORMATION:/rpt_family= "HAVE/LALW/LKA"
                /rpt_unit= 244 .. 270

(ix) FEATURE:
            (A) NAME/KEY: misc_feature
            (B) LOCATION:3127
            (D) OTHER INFORMATION:/function= "Possible N-linked
                glycosylation site"

(ix) FEATURE:
            (A) NAME/KEY: misc_feature
            (B) LOCATION:3631
            (D) OTHER INFORMATION:/function= "Possible N-linked
                glycosylation site"

(ix) FEATURE:
            (A) NAME/KEY: misc_feature
            (B) LOCATION:4513
            (D) OTHER INFORMATION:/function= "Possible N-linked
                glycosylation site"

(ix) FEATURE:
            (A) NAME/KEY: misc_feature
            (B) LOCATION:4900
            (D) OTHER INFORMATION:/function= "Possible N-linked
                glycosylation site"

(ix) FEATURE:
            (A) NAME/KEY: misc_feature
            (B) LOCATION:2386
            (D) OTHER INFORMATION:/function= "Possible tyrosine (Y)
                kinase phosphorylation site"

(ix) FEATURE:
            (A) NAME/KEY: misc_feature
            (B) LOCATION:5227
            (D) OTHER INFORMATION:/function= "Possible tyrosine (Y)
                kinase phosphorylation site"

(ix) FEATURE:
            (A) NAME/KEY: misc_feature
            (B) LOCATION:5425..5430
            (D) OTHER INFORMATION:/function= "Potential
                polyadenylation signal"
```

-continued (ix) FEATURE:
    (A) NAME/KEY: misc_feature
    (B) LOCATION:5429..5434
    (D) OTHER INFORMATION:/function= "Potential
        polyadenylation signal"

(ix) FEATURE:
    (A) NAME/KEY: misc_feature
    (B) LOCATION:5460
    (D) OTHER INFORMATION:/function= "Potential
        polyadenylation cleavage site"

(ix) FEATURE:
    (A) NAME/KEY: misc_feature
    (B) LOCATION:5474
    (D) OTHER INFORMATION:/product= "Potential
        polyadenylation cleavage site at position 5475"

(xi) SEQUENCE DESCRIPTION: SEQ ID NO: 1:

```
GGTGCGTCCT GGTCCACC ATG GCC AAA CCA ACA AGC AAA GAT TCA GGC TTG        51
                    Met Ala Lys Pro Thr Ser Lys Asp Ser Gly Leu
                     1               5                      10

AAG GAG AAG TTT AAG ATT CTG TTG GGA CTG GGA ACA CCG AGG CCA AAT        99
Lys Glu Lys Phe Lys Ile Leu Leu Gly Leu Gly Thr Pro Arg Pro Asn
            15                  20                  25

CCC AGG TCT GCA GAG GGT AAA CAG ACG GAG TTT ATC ATC ACC GCG GAA       147
Pro Arg Ser Ala Glu Gly Lys Gln Thr Glu Phe Ile Ile Thr Ala Glu
        30                  35                  40

ATA CTG AGA GAA CTG AGC ATG GAA TGT GGC CTC AAC AAT CGC ATC CGG       195
Ile Leu Arg Glu Leu Ser Met Glu Cys Gly Leu Asn Asn Arg Ile Arg
    45                  50                  55

ATG ATA GGG CAG ATT TGT GAA GTC GCA AAA ACC AAG AAA TTT GAA GAG       243
Met Ile Gly Gln Ile Cys Glu Val Ala Lys Thr Lys Lys Phe Glu Glu
 60                  65                  70                  75

CAC GCA GTG GAA GCA CTC TGG AAG GCG GTC GCG GAT CTG TTG CAG CCG       291
His Ala Val Glu Ala Leu Trp Lys Ala Val Ala Asp Leu Leu Gln Pro
                    80                  85                  90

GAG CGG ACG CTG GAG GCC CGG CAC GCG GTG CTG GCT CTG CTG AAG GCC       339
Glu Arg Thr Leu Glu Ala Arg His Ala Val Leu Ala Leu Leu Lys Ala
            95                 100                 105

ATC GTG CAG GGG CAG GGC GAG CGT TTG GGG GTC CTC AGA GCC CTC TTC       387
Ile Val Gln Gly Gln Gly Glu Arg Leu Gly Val Leu Arg Ala Leu Phe
       110                 115                 120

TTT AAG GTC ATC AAG GAT TAC CCT TCC AAC GAA GAC CTT CAC GAA AGG       435
Phe Lys Val Ile Lys Asp Tyr Pro Ser Asn Glu Asp Leu His Glu Arg
   125                 130                 135

CTG GAG GTT TTC AAG GCC CTC ACA GAC AAT GGG AGA CAC ATC ACC TAC       483
Leu Glu Val Phe Lys Ala Leu Thr Asp Asn Gly Arg His Ile Thr Tyr
140                 145                 150                 155

TTG GAG GAA GAG CTG GCT GAC TTT GTC CTG CAG TGG ATG GAT GTT GGC       531
Leu Glu Glu Glu Leu Ala Asp Phe Val Leu Gln Trp Met Asp Val Gly
                160                 165                 170

TTG TCC TCG GAA TTC CTT CTG GTG CTG GTG AAC TTG GTC AAA TTC AAT       579
Leu Ser Ser Glu Phe Leu Leu Val Leu Val Asn Leu Val Lys Phe Asn
            175                 180                 185

AGC TGT TAC CTC GAC GAG TAC ATC GCA AGG ATG GTT CAG ATG ATC TGT       627
Ser Cys Tyr Leu Asp Glu Tyr Ile Ala Arg Met Val Gln Met Ile Cys
        190                 195                 200

CTG CTG TGC GTC CGG ACC GCG TCC TCT GTG GAC ATA GAG GTC TCC CTG       675
Leu Leu Cys Val Arg Thr Ala Ser Ser Val Asp Ile Glu Val Ser Leu
    205                 210                 215

CAG GTG CTG GAC GCC GTG GTC TGC TAC AAC TGC CTG CCG GCT GAG AGC       723
Gln Val Leu Asp Ala Val Val Cys Tyr Asn Cys Leu Pro Ala Glu Ser
```

```
                220                 225                 230                 235
CTC CCG CTG TTC ATC GTT ACC CTC TGT CGC ACC ATC AAC GTC AAG GAG        771
Leu Pro Leu Phe Ile Val Thr Leu Cys Arg Thr Ile Asn Val Lys Glu
                    240                 245                 250

CTC TGC GAG CCT TGC TGG AAG CTG ATG CGG AAC CTC CTT GGC ACC CAC        819
Leu Cys Glu Pro Cys Trp Lys Leu Met Arg Asn Leu Leu Gly Thr His
                255                 260                 265

CTG GGC CAC AGC GCC ATC TAC AAC ATG TGC CAC CTC ATG GAG GAC AGA        867
Leu Gly His Ser Ala Ile Tyr Asn Met Cys His Leu Met Glu Asp Arg
            270                 275                 280

GCC TAC ATG GAG GAC GCG CCC CTG CTG AGA GGA GCC GTG TTT TTT GTG        915
Ala Tyr Met Glu Asp Ala Pro Leu Leu Arg Gly Ala Val Phe Phe Val
        285                 290                 295

GGC ATG GCT CTC TGG GGA GCC CAC CGG CTC TAT TCT CTC AGG AAC TCG        963
Gly Met Ala Leu Trp Gly Ala His Arg Leu Tyr Ser Leu Arg Asn Ser
300                 305                 310                 315

CCG ACA TCT GTG TTT CCA TCA TTT TAC CAG GCC ATG GCA TGT CCG AAC       1011
Pro Thr Ser Val Phe Pro Ser Phe Tyr Gln Ala Met Ala Cys Pro Asn
                320                 325                 330

GAG GTG GTG TCC TAT GAG ATC GTC CTG TCC ATC ACC AGG CTC ATC AAG       1059
Glu Val Val Ser Tyr Glu Ile Val Leu Ser Ile Thr Arg Leu Ile Lys
                335                 340                 345

AAG TAT AGG AAG GAG CTC CAG GTG GTG GCG TGG GAC ATT CTG CTG AAC       1107
Lys Tyr Arg Lys Glu Leu Gln Val Val Ala Trp Asp Ile Leu Leu Asn
            350                 355                 360

ATC ATC GAA CGG CTC CTT CAA CAG CTC CAG ACC TTG GAC AGC CCG GAG       1155
Ile Ile Glu Arg Leu Leu Gln Gln Leu Gln Thr Leu Asp Ser Pro Glu
        365                 370                 375

CTC AGG ACC ATC GTC CAT GAC CTG TTG ACC ACG GTG GAG GAG CTG TGT       1203
Leu Arg Thr Ile Val His Asp Leu Leu Thr Thr Val Glu Glu Leu Cys
380                 385                 390                 395

GAC CAG AAC GAG TTC CAC GGG TCT CAG GAG AGA TAC TTT GAA CTG GTG       1251
Asp Gln Asn Glu Phe His Gly Ser Gln Glu Arg Tyr Phe Glu Leu Val
                400                 405                 410

GAG AGA TGT GCG GAC CAG AGG CCT GAG TCC TCC CTC CTG AAC CTG ATC       1299
Glu Arg Cys Ala Asp Gln Arg Pro Glu Ser Ser Leu Leu Asn Leu Ile
                415                 420                 425

TCC TAT AGA GCG CAG TCC ATC CAC CCG GCC AAG GAC GGC TGG ATT CAG       1347
Ser Tyr Arg Ala Gln Ser Ile His Pro Ala Lys Asp Gly Trp Ile Gln
            430                 435                 440

AAC CTG CAG GCG CTG ATG GAG AGA TTC TTC AGG AGC GAG TCC CGA GGC       1395
Asn Leu Gln Ala Leu Met Glu Arg Phe Phe Arg Ser Glu Ser Arg Gly
        445                 450                 455

GCC GTG CGC ATC AAG GTG CTG GAC GTG CTG TCC TTT GTG CTG CTC ATC       1443
Ala Val Arg Ile Lys Val Leu Asp Val Leu Ser Phe Val Leu Leu Ile
460                 465                 470                 475

AAC AGG CAG TTC TAT GAG GAG GAG CTG ATT AAC TCA GTG GTC ATC TCG       1491
Asn Arg Gln Phe Tyr Glu Glu Glu Leu Ile Asn Ser Val Val Ile Ser
                480                 485                 490

CAG CTC TCC CAC ATC CCC GAG GAT AAA GAC CAC CAG GTC CGA AAG CTG       1539
Gln Leu Ser His Ile Pro Glu Asp Lys Asp His Gln Val Arg Lys Leu
                495                 500                 505

GCC ACC CAG TTG CTG GTG GAC CTG GCA GAG GGC TGC CAC ACA CAC CAC       1587
Ala Thr Gln Leu Leu Val Asp Leu Ala Glu Gly Cys His Thr His His
            510                 515                 520

TTC AAC AGC CTG CTG GAC ATC ATC GAG AAG GTG ATG GCC CGC TCC CTC       1635
Phe Asn Ser Leu Leu Asp Ile Ile Glu Lys Val Met Ala Arg Ser Leu
        525                 530                 535

TCC CCA CCC CCG GAG CTG GAA GAA AGG GAT GTG GCC GCA TAC TCG GCC       1683
```

```
Ser Pro Pro Pro Glu Leu Glu Arg Asp Val Ala Ala Tyr Ser Ala
540                 545                 550                 555

TCC TTG GAG GAT GTG AAG ACA GCC GTC CTG GGG CTT CTG GTC ATC CTT    1731
Ser Leu Glu Asp Val Lys Thr Ala Val Leu Gly Leu Leu Val Ile Leu
                560                 565                 570

CAG ACC AAG CTG TAC ACC CTG CCT GCA AGC CAC GCC ACG CGT GTG TAT    1779
Gln Thr Lys Leu Tyr Thr Leu Pro Ala Ser His Ala Thr Arg Val Tyr
            575                 580                 585

GAG ATG CTG GTC AGC CAC ATT CAG CTC CAC TAC AAG CAC AGC TAC ACC    1827
Glu Met Leu Val Ser His Ile Gln Leu His Tyr Lys His Ser Tyr Thr
            590                 595                 600

CTG CCA ATC GCG AGC AGC ATC CGG CTG CAG GCC TTT GAC TTC CTG TTT    1875
Leu Pro Ile Ala Ser Ser Ile Arg Leu Gln Ala Phe Asp Phe Leu Phe
            605                 610                 615

CTG CTG CGG GCC GAC TCA CTG CAC CGC CTG GGC CTG CCC AAC AAG GAT    1923
Leu Leu Arg Ala Asp Ser Leu His Arg Leu Gly Leu Pro Asn Lys Asp
620                 625                 630                 635

GGA GTC GTG CGG TTC AGC CCC TAC TGC GTC TGC GAC TAC ATG GAG CCA    1971
Gly Val Val Arg Phe Ser Pro Tyr Cys Val Cys Asp Tyr Met Glu Pro
                640                 645                 650

GAG AGA GGC TCT GAG AAG AAG ACC AGC GGC CCC CTT TCT CCT CCC ACA    2019
Glu Arg Gly Ser Glu Lys Lys Thr Ser Gly Pro Leu Ser Pro Pro Thr
            655                 660                 665

GGG CCT CCT GGC CCG GCG CCT GCA GGC CCC GCC GTG CGG CTG GGG TCC    2067
Gly Pro Pro Gly Pro Ala Pro Ala Gly Pro Ala Val Arg Leu Gly Ser
            670                 675                 680

GTG CCC TAC TCC CTG CTC TTC CGC GTC CTG CTG CAG TGC TTG AAG CAG    2115
Val Pro Tyr Ser Leu Leu Phe Arg Val Leu Leu Gln Cys Leu Lys Gln
            685                 690                 695

GAG TCT GAC TGG AAG GTG CTG AAG CTG GTT CTG GGC AGG CTG CCT GAG    2163
Glu Ser Asp Trp Lys Val Leu Lys Leu Val Leu Gly Arg Leu Pro Glu
700                 705                 710                 715

TCC CTG CGC TAT AAA GTG CTC ATC TTT ACT TCC CCT TGC AGT GTG GAC    2211
Ser Leu Arg Tyr Lys Val Leu Ile Phe Thr Ser Pro Cys Ser Val Asp
            720                 725                 730

CAG CTG TGC TCT GCT CTC TGC TCC ATG CTT TCA GGC CCA AAG ACA CTG    2259
Gln Leu Cys Ser Ala Leu Cys Ser Met Leu Ser Gly Pro Lys Thr Leu
            735                 740                 745

GAG CGG CTC CGA GGC GCC CCA GAA GGC TTC TCC AGA ACT GAC TTG CAC    2307
Glu Arg Leu Arg Gly Ala Pro Glu Gly Phe Ser Arg Thr Asp Leu His
            750                 755                 760

CTG GCC GTG GTT CCA GTG CTG ACA GCA TTA ATC TCT TAC CAT AAC TAC    2355
Leu Ala Val Val Pro Val Leu Thr Ala Leu Ile Ser Tyr His Asn Tyr
765                 770                 775

CTG GAC AAA ACC AAA CAG CGC GAG ATG GTC TAC TGC CTG GAG CAG GGC    2403
Leu Asp Lys Thr Lys Gln Arg Glu Met Val Tyr Cys Leu Glu Gln Gly
780                 785                 790                 795

CTC ATC CAC CGC TGT GCC AGA CAG TGC GTC GTG GCC TTG TCC ATC TGC    2451
Leu Ile His Arg Cys Ala Arg Gln Cys Val Val Ala Leu Ser Ile Cys
                800                 805                 810

AGC GTG GAG ATG CCT GAC ATC ATC ATC AAG GCG CTG CCT GTT CTG GTG    2499
Ser Val Glu Met Pro Asp Ile Ile Ile Lys Ala Leu Pro Val Leu Val
            815                 820                 825

GTG AAG CTC ACG CAC ATC TCA GCC ACA GCC AGC ATG GCC GTC CCA CTG    2547
Val Lys Leu Thr His Ile Ser Ala Thr Ala Ser Met Ala Val Pro Leu
            830                 835                 840

CTG GAG TTC CTG TCC ACT CTG GCC AGG CTG CCG CAC CTC TAC AGG AAC    2595
Leu Glu Phe Leu Ser Thr Leu Ala Arg Leu Pro His Leu Tyr Arg Asn
845                 850                 855
```

```
TTT GCC GCG GAG CAG TAT GCC AGT GTG TTC GCC ATC TCC CTG CCG TAC    2643
Phe Ala Ala Glu Gln Tyr Ala Ser Val Phe Ala Ile Ser Leu Pro Tyr
860                 865                 870                 875

ACC AAC CCC TCC AAG TTT AAT CAG TAC ATC GTG TGT CTG GCC CAT CAC    2691
Thr Asn Pro Ser Lys Phe Asn Gln Tyr Ile Val Cys Leu Ala His His
                880                 885                 890

GTC ATA GCC ATG TGG TTC ATC AGG TGC CGC CTG CCC TTC CGG AAG GAT    2739
Val Ile Ala Met Trp Phe Ile Arg Cys Arg Leu Pro Phe Arg Lys Asp
            895                 900                 905

TTT GTC CCT TTC ATC ACT AAG GGC CTG CGG TCC AAT GTC CTC TTG TCT    2787
Phe Val Pro Phe Ile Thr Lys Gly Leu Arg Ser Asn Val Leu Leu Ser
        910                 915                 920

TTT GAT GAC ACC CCC GAG AAG GAC AGC TTC AGG GCC CGG AGT ACT AGT    2835
Phe Asp Asp Thr Pro Glu Lys Asp Ser Phe Arg Ala Arg Ser Thr Ser
    925                 930                 935

CTC AAC GAG AGA CCC AAG AGT CTG AGG ATA GCC AGA CCC CCC AAA CAA    2883
Leu Asn Glu Arg Pro Lys Ser Leu Arg Ile Ala Arg Pro Pro Lys Gln
940                 945                 950                 955

GGC TTG AAT AAC TCT CCA CCC GTG AAA GAA TTC AAG GAG AGC TCT GCA    2931
Gly Leu Asn Asn Ser Pro Pro Val Lys Glu Phe Lys Glu Ser Ser Ala
                960                 965                 970

GCC GAG GCC TTC CGG TGC CGC AGC ATC AGT GTG TCT GAA CAT GTG GTC    2979
Ala Glu Ala Phe Arg Cys Arg Ser Ile Ser Val Ser Glu His Val Val
            975                 980                 985

CGC AGC AGG ATA CAG ACG TCC CTC ACC AGT GCC AGC TTG GGG TCT GCA    3027
Arg Ser Arg Ile Gln Thr Ser Leu Thr Ser Ala Ser Leu Gly Ser Ala
        990                 995                 1000

GAT GAG AAC TCC GTG GCC CAG GCT GAC GAT AGC CTG AAA AAC CTC CAC    3075
Asp Glu Asn Ser Val Ala Gln Ala Asp Asp Ser Leu Lys Asn Leu His
    1005                1010                1015

CTG GAG CTC ACG GAA ACC TGT CTG GAC ATG ATG GCT CGA TAC GTC TTC    3123
Leu Glu Leu Thr Glu Thr Cys Leu Asp Met Met Ala Arg Tyr Val Phe
1020                1025                1030                1035

TCC AAC TTC ACG GCT GTC CCG AAG AGG TCT CCT GTG GGC GAG TTC CTC    3171
Ser Asn Phe Thr Ala Val Pro Lys Arg Ser Pro Val Gly Glu Phe Leu
                1040                1045                1050

CTA GCG GGT GGC AGG ACC AAA ACC TGG CTG GTT GGG AAC AAG CTT GTC    3219
Leu Ala Gly Gly Arg Thr Lys Thr Trp Leu Val Gly Asn Lys Leu Val
            1055                1060                1065

ACT GTG ACG ACA AGC GTG GGA ACC GGG ACC CGG TCG TTA CTA GGC CTG    3267
Thr Val Thr Thr Ser Val Gly Thr Gly Thr Arg Ser Leu Leu Gly Leu
        1070                1075                1080

GAC TCG GGG GAG CTG CAG TCC GGC CCG GAG TCG AGC TCC AGC CCC GGG    3315
Asp Ser Gly Glu Leu Gln Ser Gly Pro Glu Ser Ser Ser Ser Pro Gly
    1085                1090                1095

GTG CAT GTG AGA CAG ACC AAG GAG GCG CCG GCC AAG CTG GAG TCC CAG    3363
Val His Val Arg Gln Thr Lys Glu Ala Pro Ala Lys Leu Glu Ser Gln
1100                1105                1110                1115

GCT GGG CAG CAG GTG TCC CGT GGG GCC CGG GAT CGG GTC CGT TCC ATG    3411
Ala Gly Gln Gln Val Ser Arg Gly Ala Arg Asp Arg Val Arg Ser Met
                1120                1125                1130

TCG GGG GGC CAT GGT CTT CGA GTT GGC GCC CTG GAC GTG CCG GCC TCC    3459
Ser Gly Gly His Gly Leu Arg Val Gly Ala Leu Asp Val Pro Ala Ser
            1135                1140                1145

CAG TTC CTG GGC AGT GCC ACT TCT CCA GGA CCA CGG ACT GCA CCA GCC    3507
Gln Phe Leu Gly Ser Ala Thr Ser Pro Gly Pro Arg Thr Ala Pro Ala
        1150                1155                1160

GCG AAA CCT GAG AAG GCC TCA GCT GGC ACC CGG GTT CCT GTG CAG GAG    3555
Ala Lys Pro Glu Lys Ala Ser Ala Gly Thr Arg Val Pro Val Gln Glu
    1165                1170                1175
```

-continued

| | |
|---|---|
| AAG ACG AAC CTG GCG GCC TAT GTG CCC CTG CTG ACC CAG GGC TGG GCG<br>Lys Thr Asn Leu Ala Ala Tyr Val Pro Leu Leu Thr Gln Gly Trp Ala<br>1180                        1185                        1190                        1195 | 3603 |
| GAG ATC CTG GTC CGG AGG CCC ACA GGG AAC ACC AGC TGG CTG ATG AGC<br>Glu Ile Leu Val Arg Arg Pro Thr Gly Asn Thr Ser Trp Leu Met Ser<br>                      1200                        1205                        1210 | 3651 |
| CTG GAG AAC CCG CTC AGC CCT TTC TCC TCG GAC ATC AAC AAC ATG CCC<br>Leu Glu Asn Pro Leu Ser Pro Phe Ser Ser Asp Ile Asn Asn Met Pro<br>                    1215                        1220                        1225 | 3699 |
| CTG CAG GAG CTG TCT AAC GCC CTC ATG GCG GCT GAG CGC TTC AAG GAG<br>Leu Gln Glu Leu Ser Asn Ala Leu Met Ala Ala Glu Arg Phe Lys Glu<br>1230                        1235                        1240 | 3747 |
| CAC CGG GAC ACA GCC CTG TAC AAG TCA CTG TCG GTG CCG GCA GCC AGC<br>His Arg Asp Thr Ala Leu Tyr Lys Ser Leu Ser Val Pro Ala Ala Ser<br>                    1245                        1250                        1255 | 3795 |
| ACG GCC AAA CCC CCT CCT CTG CCT CGC TCC AAC ACA GAC TCC GCC GTG<br>Thr Ala Lys Pro Pro Pro Leu Pro Arg Ser Asn Thr Asp Ser Ala Val<br>1260                        1265                        1270                        1275 | 3843 |
| GTC ATG GAG GAG GGA AGT CCG GGC GAG GTT CCT GTG CTG GTG GAG CCC<br>Val Met Glu Glu Gly Ser Pro Gly Glu Val Pro Val Leu Val Glu Pro<br>                    1280                        1285                        1290 | 3891 |
| CCA GGG TTG GAG GAC GTT GAG GCA GCG CTA GGC ATG GAC AGG CGC ACG<br>Pro Gly Leu Glu Asp Val Glu Ala Ala Leu Gly Met Asp Arg Arg Thr<br>        1295                        1300                        1305 | 3939 |
| GAT GCC TAC AGC AGG TCG TCC TCA GTC TCC AGC CAG GAG GAG AAG TCG<br>Asp Ala Tyr Ser Arg Ser Ser Ser Val Ser Ser Gln Glu Glu Lys Ser<br>                    1310                        1315                        1320 | 3987 |
| CTC CAC GCG GAG GAG CTG GTT GGC AGG GGC ATC CCC ATC GAG CGA GTC<br>Leu His Ala Glu Glu Leu Val Gly Arg Gly Ile Pro Ile Glu Arg Val<br>1325                        1330                        1335 | 4035 |
| GTC TCC TCG GAG GGT GGC CGG CCC TCT GTG GAC CTC TCC TTC CAG CCC<br>Val Ser Ser Glu Gly Gly Arg Pro Ser Val Asp Leu Ser Phe Gln Pro<br>1340                        1345                        1350                        1355 | 4083 |
| TCG CAG CCC CTG AGC AAG TCC AGC TCC TCT CCC GAG CTG CAG ACT CTG<br>Ser Gln Pro Leu Ser Lys Ser Ser Ser Pro Glu Leu Gln Thr Leu<br>                    1360                        1365                        1370 | 4131 |
| CAG GAC ATC CTC GGG GAC CCT GGG GAC AAG GCC GAC GTG GGC CGG CTG<br>Gln Asp Ile Leu Gly Asp Pro Gly Asp Lys Ala Asp Val Gly Arg Leu<br>                    1375                        1380                        1385 | 4179 |
| AGC CCT GAG GTT AAG GCC CGG TCA CAG TCA GGG ACC CTG GAC GGG GAA<br>Ser Pro Glu Val Lys Ala Arg Ser Gln Ser Gly Thr Leu Asp Gly Glu<br>                    1390                        1395                        1400 | 4227 |
| AGT GCT GCC TGG TCG GCC TCG GGC GAA GAC AGT CGG GGC CAG CCC GAG<br>Ser Ala Ala Trp Ser Ala Ser Gly Glu Asp Ser Arg Gly Gln Pro Glu<br>1405                        1410                        1415 | 4275 |
| GGT CCC TTG CCT TCC AGC TCC CCC CGC TCG CCC AGT GGC CTC CGG CCC<br>Gly Pro Leu Pro Ser Ser Ser Pro Arg Ser Pro Ser Gly Leu Arg Pro<br>1420                        1425                        1430                        1435 | 4323 |
| CGA GGT TAC ACC ATC TCC GAC TCG GCC CCA TCA CGC AGG GGC AAG AGA<br>Arg Gly Tyr Thr Ile Ser Asp Ser Ala Pro Ser Arg Arg Gly Lys Arg<br>                    1440                        1445                        1450 | 4371 |
| GTA GAG AGG GAC GCC TTA AAG AGC AGA GCC ACA GCC TCC AAT GCA GAG<br>Val Glu Arg Asp Ala Leu Lys Ser Arg Ala Thr Ala Ser Asn Ala Glu<br>                    1455                        1460                        1465 | 4419 |
| AAA GTG CCA GGC ATC AAC CCC AGT TTC GTG TTC CTG CAG CTC TAC CAT<br>Lys Val Pro Gly Ile Asn Pro Ser Phe Val Phe Leu Gln Leu Tyr His<br>                    1470                        1475                        1480 | 4467 |
| TCC CCC TTC TTT GGC GAC GAG TCA AAC AAG CCA ATC CTG CTG CCC AAT<br>Ser Pro Phe Phe Gly Asp Glu Ser Asn Lys Pro Ile Leu Leu Pro Asn | 4515 |

```
                1485                1490                 1495
GAG TCA CAG TCC TTT GAG CGG TCG GTG CAG CTC CTC GAC CAG ATC CCA     4563
Glu Ser Gln Ser Phe Glu Arg Ser Val Gln Leu Leu Asp Gln Ile Pro
1500                1505                 1510                1515

TCA TAC GAC ACC CAC AAG ATC GCC GTC CTG TAT GTT GGA GAA GGC CAG     4611
Ser Tyr Asp Thr His Lys Ile Ala Val Leu Tyr Val Gly Glu Gly Gln
            1520                1525                 1530

AGC AAC AGC GAG CTC GCC ATC CTG TCC AAT GAG CAT GGC TCC TAC AGG     4659
Ser Asn Ser Glu Leu Ala Ile Leu Ser Asn Glu His Gly Ser Tyr Arg
        1535                1540                1545

TAC ACG GAG TTC CTG ACG GGC CTG GGC CGG CTC ATC GAG CTG AAG GAC     4707
Tyr Thr Glu Phe Leu Thr Gly Leu Gly Arg Leu Ile Glu Leu Lys Asp
            1550                1555                 1560

TGC CAG CCG GAC AAG GTG TAC CTG GGA GGC CTG GAC GTG TGT GGT GAG     4755
Cys Gln Pro Asp Lys Val Tyr Leu Gly Gly Leu Asp Val Cys Gly Glu
        1565                1570                 1575

GAC GGC CAG TTC ACC TAC TGC TGG CAC GAT GAC ATC ATG CAA GCC GTC     4803
Asp Gly Gln Phe Thr Tyr Cys Trp His Asp Asp Ile Met Gln Ala Val
1580                1585                 1590                1595

TTC CAC ATC GCC ACC CTG ATG CCC ACC AAG GAC GTG GAC AAG CAC CGC     4851
Phe His Ile Ala Thr Leu Met Pro Thr Lys Asp Val Asp Lys His Arg
            1600                1605                 1610

TGC GAC AAG AAG CGC CAC CTG GGC AAC GAC TTT GTG TCC ATT GTC TAC     4899
Cys Asp Lys Lys Arg His Leu Gly Asn Asp Phe Val Ser Ile Val Tyr
        1615                1620                1625

AAT GAC TCC GGT GAG GAC TTC AAG CTT GGC ACC ATC AAG GGC CAG TTC     4947
Asn Asp Ser Gly Glu Asp Phe Lys Leu Gly Thr Ile Lys Gly Gln Phe
            1630                1635                 1640

AAC TTT GTC CAC GTG ATC GTC ACC CCG CTG GAC TAC GAG TGC AAC CTG     4995
Asn Phe Val His Val Ile Val Thr Pro Leu Asp Tyr Glu Cys Asn Leu
        1645                1650                 1655

GTG TCC CTG CAG TGC AGG AAA GAC ATG GAG GGC CTT GTG GAC ACC AGC     5043
Val Ser Leu Gln Cys Arg Lys Asp Met Glu Gly Leu Val Asp Thr Ser
1660                1665                 1670                1675

GTG GCC AAG ATC GTG TCT GAC CGC AAC CTG CCC TTC GTG GCC CGC CAG     5091
Val Ala Lys Ile Val Ser Asp Arg Asn Leu Pro Phe Val Ala Arg Gln
            1680                1685                 1690

ATG GCC CTG CAC GCA AAT ATG GCC TCA CAG GTG CAT CAT AGC CGC TCC     5139
Met Ala Leu His Ala Asn Met Ala Ser Gln Val His His Ser Arg Ser
        1695                1700                1705

AAC CCC ACC GAT ATC TAC CCC TCC AAG TGG ATT GCC CGG CTC CGC CAC     5187
Asn Pro Thr Asp Ile Tyr Pro Ser Lys Trp Ile Ala Arg Leu Arg His
            1710                1715                 1720

ATC AAG CGG CTC CGC CAG CGG ATC TGC GAG GAA GCC GCC TAC TCC AAC     5235
Ile Lys Arg Leu Arg Gln Arg Ile Cys Glu Glu Ala Ala Tyr Ser Asn
        1725                1730                1735

CCC AGC CTA CCT CTG GTG CAC CCT CCG TCC CAT AGC AAA GCC CCT GCA     5283
Pro Ser Leu Pro Leu Val His Pro Pro Ser His Ser Lys Ala Pro Ala
1740                1745                 1750                1755

CAG ACT CCA GCC GAG CCC ACA CCT GGC TAT GAG GTG GGC CAG CGG AAG     5331
Gln Thr Pro Ala Glu Pro Thr Pro Gly Tyr Glu Val Gly Gln Arg Lys
            1760                1765                 1770

CGC CTC ATC TCC TCG GTG GAG GAC TTC ACC GAG TTT GTG TGAGGCCGGG     5380
Arg Leu Ile Ser Ser Val Glu Asp Phe Thr Glu Phe Val
                1775                1780

GCCCTCCCTC CTGCACTGGC CTTGGACGGT ATTGCCTGTC AGTGAAATAA ATAAAGTCCT     5440

GACCCCAGTG CACAGACATA GAGGCACAGA TTGC                                 5474
```

(2) INFORMATION FOR SEQ ID NO: 2:

(i) SEQUENCE CHARACTERISTICS:
        (A) LENGTH: 1784 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Lys Pro Thr Ser Lys Asp Ser Gly Leu Lys Glu Lys Phe Lys
  1               5                  10                  15

Ile Leu Leu Gly Leu Gly Thr Pro Arg Pro Asn Pro Arg Ser Ala Glu
             20                  25                  30

Gly Lys Gln Thr Glu Phe Ile Ile Thr Ala Glu Ile Leu Arg Glu Leu
             35                  40                  45

Ser Met Glu Cys Gly Leu Asn Asn Arg Ile Arg Met Ile Gly Gln Ile
         50                  55                  60

Cys Glu Val Ala Lys Thr Lys Lys Phe Glu Glu His Ala Val Glu Ala
 65                  70                  75                  80

Leu Trp Lys Ala Val Ala Asp Leu Leu Gln Pro Glu Arg Thr Leu Glu
                 85                  90                  95

Ala Arg His Ala Val Leu Ala Leu Leu Lys Ala Ile Val Gln Gly Gln
             100                 105                 110

Gly Glu Arg Leu Gly Val Leu Arg Ala Leu Phe Phe Lys Val Ile Lys
             115                 120                 125

Asp Tyr Pro Ser Asn Glu Asp Leu His Glu Arg Leu Glu Val Phe Lys
130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                 165                 170                 175

Leu Leu Val Leu Val Asn Leu Val Lys Phe Asn Ser Cys Tyr Leu Asp
             180                 185                 190

Glu Tyr Ile Ala Arg Met Val Gln Met Ile Cys Leu Leu Cys Val Arg
             195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                 245                 250                 255

Trp Lys Leu Met Arg Asn Leu Leu Gly Thr His Leu Gly His Ser Ala
             260                 265                 270

Ile Tyr Asn Met Cys His Leu Met Glu Asp Arg Ala Tyr Met Glu Asp
             275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Phe
305                 310                 315                 320

Pro Ser Phe Tyr Gln Ala Met Ala Cys Pro Asn Glu Val Val Ser Tyr
                 325                 330                 335

Glu Ile Val Leu Ser Ile Thr Arg Leu Ile Lys Lys Tyr Arg Lys Glu
             340                 345                 350

Leu Gln Val Val Ala Trp Asp Ile Leu Leu Asn Ile Ile Glu Arg Leu
             355                 360                 365
```

```
Leu Gln Gln Leu Gln Thr Leu Asp Ser Pro Glu Leu Arg Thr Ile Val
    370                 375                 380
His Asp Leu Leu Thr Thr Val Glu Glu Leu Cys Asp Gln Asn Glu Phe
385                 390                 395                 400
His Gly Ser Gln Glu Arg Tyr Phe Glu Leu Val Glu Arg Cys Ala Asp
                405                 410                 415
Gln Arg Pro Glu Ser Ser Leu Leu Asn Leu Ile Ser Tyr Arg Ala Gln
            420                 425                 430
Ser Ile His Pro Ala Lys Asp Gly Trp Ile Gln Asn Leu Gln Ala Leu
        435                 440                 445
Met Glu Arg Phe Phe Arg Ser Glu Ser Arg Gly Ala Val Arg Ile Lys
    450                 455                 460
Val Leu Asp Val Leu Ser Phe Val Leu Leu Ile Asn Arg Gln Phe Tyr
465                 470                 475                 480
Glu Glu Glu Leu Ile Asn Ser Val Val Ile Ser Gln Leu Ser His Ile
                485                 490                 495
Pro Glu Asp Lys Asp His Gln Val Arg Lys Leu Ala Thr Gln Leu Leu
            500                 505                 510
Val Asp Leu Ala Glu Gly Cys His Thr His His Phe Asn Ser Leu Leu
        515                 520                 525
Asp Ile Ile Glu Lys Val Met Ala Arg Ser Leu Ser Pro Pro Pro Glu
    530                 535                 540
Leu Glu Glu Arg Asp Val Ala Ala Tyr Ser Ala Ser Leu Glu Asp Val
545                 550                 555                 560
Lys Thr Ala Val Leu Gly Leu Leu Val Ile Leu Gln Thr Lys Leu Tyr
                565                 570                 575
Thr Leu Pro Ala Ser His Ala Thr Arg Val Tyr Glu Met Leu Val Ser
            580                 585                 590
His Ile Gln Leu His Tyr Lys His Ser Tyr Thr Leu Pro Ile Ala Ser
        595                 600                 605
Ser Ile Arg Leu Gln Ala Phe Asp Phe Leu Phe Leu Leu Arg Ala Asp
    610                 615                 620
Ser Leu His Arg Leu Gly Leu Pro Asn Lys Asp Gly Val Val Arg Phe
625                 630                 635                 640
Ser Pro Tyr Cys Val Cys Asp Tyr Met Glu Pro Glu Arg Gly Ser Glu
                645                 650                 655
Lys Lys Thr Ser Gly Pro Leu Ser Pro Pro Thr Gly Pro Pro Gly Pro
            660                 665                 670
Ala Pro Ala Gly Pro Ala Val Arg Leu Gly Ser Val Pro Tyr Ser Leu
        675                 680                 685
Leu Phe Arg Val Leu Leu Gln Cys Leu Lys Gln Glu Ser Asp Trp Lys
    690                 695                 700
Val Leu Lys Leu Val Leu Gly Arg Leu Pro Glu Ser Leu Arg Tyr Lys
705                 710                 715                 720
Val Leu Ile Phe Thr Ser Pro Cys Ser Val Asp Gln Leu Cys Ser Ala
                725                 730                 735
Leu Cys Ser Met Leu Ser Gly Pro Lys Thr Leu Glu Arg Leu Arg Gly
            740                 745                 750
Ala Pro Glu Gly Phe Ser Arg Thr Asp Leu His Leu Ala Val Val Pro
        755                 760                 765
Val Leu Thr Ala Leu Ile Ser Tyr His Asn Tyr Leu Asp Lys Thr Lys
770                 775                 780
```

-continued

```
Gln Arg Glu Met Val Tyr Cys Leu Glu Gln Gly Leu Ile His Arg Cys
785                 790                 795                 800

Ala Arg Gln Cys Val Val Ala Leu Ser Ile Cys Ser Val Glu Met Pro
            805                 810                 815

Asp Ile Ile Ile Lys Ala Leu Pro Val Leu Val Lys Leu Thr His
                820                 825                 830

Ile Ser Ala Thr Ala Ser Met Ala Val Pro Leu Leu Glu Phe Leu Ser
            835                 840                 845

Thr Leu Ala Arg Leu Pro His Leu Tyr Arg Asn Phe Ala Ala Glu Gln
        850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
        915                 920                 925

Glu Lys Asp Ser Phe Arg Ala Arg Ser Thr Ser Leu Asn Glu Arg Pro
    930                 935                 940

Lys Ser Leu Arg Ile Ala Arg Pro Lys Gln Gly Leu Asn Asn Ser
945                 950                 955                 960

Pro Pro Val Lys Glu Phe Lys Glu Ser Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu Gly Ser Ala Asp Glu Asn Ser Val
        995                 1000                1005

Ala Gln Ala Asp Asp Ser Leu Lys Asn Leu His Leu Glu Leu Thr Glu
    1010                1015                1020

Thr Cys Leu Asp Met Met Ala Arg Tyr Val Phe Ser Asn Phe Thr Ala
1025                1030                1035                1040

Val Pro Lys Arg Ser Pro Val Gly Glu Phe Leu Leu Ala Gly Gly Arg
                1045                1050                1055

Thr Lys Thr Trp Leu Val Gly Asn Lys Leu Val Thr Val Thr Thr Ser
            1060                1065                1070

Val Gly Thr Gly Thr Arg Ser Leu Leu Gly Leu Asp Ser Gly Glu Leu
        1075                1080                1085

Gln Ser Gly Pro Glu Ser Ser Ser Pro Gly Val His Val Arg Gln
    1090                1095                1100

Thr Lys Glu Ala Pro Ala Lys Leu Glu Ser Gln Ala Gly Gln Gln Val
1105                1110                1115                1120

Ser Arg Gly Ala Arg Asp Arg Val Arg Ser Met Ser Gly Gly His Gly
                1125                1130                1135

Leu Arg Val Gly Ala Leu Asp Val Pro Ala Ser Gln Phe Leu Gly Ser
            1140                1145                1150

Ala Thr Ser Pro Gly Pro Arg Thr Ala Pro Ala Lys Pro Glu Lys
        1155                1160                1165

Ala Ser Ala Gly Thr Arg Val Pro Val Gln Glu Lys Thr Asn Leu Ala
    1170                1175                1180

Ala Tyr Val Pro Leu Leu Thr Gln Gly Trp Ala Glu Ile Leu Val Arg
1185                1190                1195                1200

Arg Pro Thr Gly Asn Thr Ser Trp Leu Met Ser Leu Glu Asn Pro Leu
```

-continued

```
              1205                1210                1215

Ser Pro Phe Ser Ser Asp Ile Asn Asn Met Pro Leu Gln Glu Leu Ser
            1220                1225                1230

Asn Ala Leu Met Ala Ala Glu Arg Phe Lys Glu His Arg Asp Thr Ala
            1235                1240                1245

Leu Tyr Lys Ser Leu Ser Val Pro Ala Ala Ser Thr Ala Lys Pro Pro
            1250                1255                1260

Pro Leu Pro Arg Ser Asn Thr Asp Ser Ala Val Val Met Glu Glu Gly
1265                1270                1275                1280

Ser Pro Gly Glu Val Pro Val Leu Val Glu Pro Pro Gly Leu Glu Asp
            1285                1290                1295

Val Glu Ala Ala Leu Gly Met Asp Arg Arg Thr Asp Ala Tyr Ser Arg
            1300                1305                1310

Ser Ser Ser Val Ser Ser Gln Glu Glu Lys Ser Leu His Ala Glu Glu
            1315                1320                1325

Leu Val Gly Arg Gly Ile Pro Ile Glu Arg Val Val Ser Ser Glu Gly
            1330                1335                1340

Gly Arg Pro Ser Val Asp Leu Ser Phe Gln Pro Ser Gln Pro Leu Ser
1345                1350                1355                1360

Lys Ser Ser Ser Pro Glu Leu Gln Thr Leu Gln Asp Ile Leu Gly
            1365                1370                1375

Asp Pro Gly Asp Lys Ala Asp Val Gly Arg Leu Ser Pro Glu Val Lys
            1380                1385                1390

Ala Arg Ser Gln Ser Gly Thr Leu Asp Gly Glu Ser Ala Ala Trp Ser
            1395                1400                1405

Ala Ser Gly Glu Asp Ser Arg Gly Gln Pro Glu Gly Pro Leu Pro Ser
            1410                1415                1420

Ser Ser Pro Arg Ser Pro Ser Gly Leu Arg Pro Arg Gly Tyr Thr Ile
1425                1430                1435                1440

Ser Asp Ser Ala Pro Ser Arg Arg Gly Lys Arg Val Glu Arg Asp Ala
            1445                1450                1455

Leu Lys Ser Arg Ala Thr Ala Ser Asn Ala Glu Lys Val Pro Gly Ile
            1460                1465                1470

Asn Pro Ser Phe Val Phe Leu Gln Leu Tyr His Ser Pro Phe Phe Gly
            1475                1480                1485

Asp Glu Ser Asn Lys Pro Ile Leu Leu Pro Asn Glu Ser Gln Ser Phe
            1490                1495                1500

Glu Arg Ser Val Gln Leu Leu Asp Gln Ile Pro Ser Tyr Asp Thr His
1505                1510                1515                1520

Lys Ile Ala Val Leu Tyr Val Gly Glu Gly Gln Ser Asn Ser Glu Leu
            1525                1530                1535

Ala Ile Leu Ser Asn Glu His Gly Ser Tyr Arg Tyr Thr Glu Phe Leu
            1540                1545                1550

Thr Gly Leu Gly Arg Leu Ile Glu Leu Lys Asp Cys Gln Pro Asp Lys
            1555                1560                1565

Val Tyr Leu Gly Gly Leu Asp Val Cys Gly Glu Asp Gly Gln Phe Thr
            1570                1575                1580

Tyr Cys Trp His Asp Asp Ile Met Gln Ala Val Phe His Ile Ala Thr
1585                1590                1595                1600

Leu Met Pro Thr Lys Asp Val Asp Lys His Arg Cys Asp Lys Lys Arg
            1605                1610                1615

His Leu Gly Asn Asp Phe Val Ser Ile Val Tyr Asn Asp Ser Gly Glu
            1620                1625                1630
```

```
Asp Phe Lys Leu Gly Thr Ile Lys Gly Gln Phe Asn Phe Val His Val
    1635                1640                1645

Ile Val Thr Pro Leu Asp Tyr Glu Cys Asn Leu Val Ser Leu Gln Cys
    1650                1655                1660

Arg Lys Asp Met Glu Gly Leu Val Asp Thr Ser Val Ala Lys Ile Val
1665                1670                1675                1680

Ser Asp Arg Asn Leu Pro Phe Val Ala Arg Gln Met Ala Leu His Ala
            1685                1690                1695

Asn Met Ala Ser Gln Val His His Ser Arg Ser Asn Pro Thr Asp Ile
        1700                1705                1710

Tyr Pro Ser Lys Trp Ile Ala Arg Leu Arg His Ile Lys Arg Leu Arg
        1715                1720                1725

Gln Arg Ile Cys Glu Glu Ala Ala Tyr Ser Asn Pro Ser Leu Pro Leu
    1730                1735                1740

Val His Pro Pro Ser His Ser Lys Ala Pro Ala Gln Thr Pro Ala Glu
1745                1750                1755                1760

Pro Thr Pro Gly Tyr Glu Val Gly Gln Arg Lys Arg Leu Ile Ser Ser
            1765                1770                1775

Val Glu Asp Phe Thr Glu Phe Val
            1780

(2) INFORMATION FOR SEQ ID NO: 3:

(i) SEQUENCE CHARACTERISTICS:
        (A) LENGTH: 39 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO: 3:

Glu Ile Met Phe His Val Ser Thr Lys Leu Pro Tyr Thr Glu Gly Asp
                5                   10                  15

Ala Gln Gln Leu Gln Arg Lys Arg His Ile Gly Asn Asp Ile Val Ala
            20                  25                  30

Val Val Phe Gln Asp Glu Asn
        35

(2) INFORMATION FOR SEQ ID NO: 4:

(i) SEQUENCE CHARACTERISTICS:
        (A) LENGTH: 39 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO: 4:

Glu Ile Met Phe His Val Ser Thr Met Leu Pro Tyr Thr Pro Asn Asn
                5                   10                  15

Gln Gln Gln Leu Leu Arg Lys Arg His Ile Gly Asn Asp Ile Val Thr
            20                  25                  30

Ile Val Phe Gln Glu Pro Gly
        35
```

TUBEROUS SCLEROSIS 2 GENE AND USES THEREOF

This application is a divisional application of U.S. Ser. No. 08/652,426, filed on Oct. 1, 1996, which is a 371 to PCT application PCT/GB94/02823, filed on Dec. 23, 1994 and also claims priority to UK Patent Application 9326470.3, filed on Dec. 24, 1993 and UK Patent Application 9411900.5 filed on Jun. 14, 1994.

The present invention relates to the tuberous sclerosis 2 (TSC2) gene, mutations thereof in patients having TSC2-associated disorders, the protein encoded by the TSC2 gene, and their uses in diagnosis and therapy.

BACKGROUND TO THE INVENTION

All references mentioned hereinbelow are listed at the end of this description and are herein incorporated by reference in their entirety.

Tuberous sclerosis (TSC) is an autosomal dominant disorder, classified as a phakomatosis (van der Hoeve, 1933) and characterised by the widespread development of growths, usually described as hamartomata, in many tissues and organs. The unpredictable distribution of these lesions, particularly within the brain, eyes, skin, kidneys, heart, lungs and skeleton results in a wide variety of signs, symptoms and complications (Gomez, 1988). Although most frequently diagnosed as a result of neurological or dermatological manifestations, renal disease was found to be the leading cause of mortality (11/40 deaths) in the largest series of TSC deaths reported so far. Renal complications including haemorrhage, hypertension and end stage renal disease (ESRD) are associated with the development of cysts and hamartomatous growths (angiomyolipomata) in the kidneys. Angiomyolipomata probably arise due to coexistent inactivating constitutional and somatic mutations, consistent with the TSC genes functioning as tumour or growth suppressor genes (Green et al (1994) and Green et al (in press)). Therefore the frequency of diagnosed cases is likely to under-represent true prevalence which may be as high as 1 in 5,800 (Osborne et al., 1991). The pathogenesis of TSC is poorly understood and efforts to establish the primary underlying defect have focused on positional cloning of the causative gene(s).

Linkage studies have established locus heterogeneity (Sampson et al., 1989a & 1992, Haines et al., 1991a&b, Janssen et al., 1991, Povey et al.,1991, Northrup et al., 1992) with disease determining genes on chromosomes 9 (Fryer et al., 1987) and 16 (Kandt et al., 1992) leading to apparently indistinguishable phenotypes. In most, if not all, affected multigeneration families the disease can be accounted for by the gene at one or other of these loci (Kwiatkowski et al., 1993). The Genome Database Nomenclature Committee recently agreed that the loci on chromosomes 9 and 16 should be termed TSC1 and TSC2 respectively. Analysis of meiotic recombination events in TSC families has refined the positions of TSC1 and TSC2 to small regions in the telomeric chromosomal bands 9q34.3 and 16p13.3. The candidate region at 16p13.3 extends between the markers MS205.2 (D16S309) and 16AC2.5 (D16S291) (Kwiatkowski et al., 1993), representing an estimated 1.5 megabases of DNA.

Loss of heterozygosity for alleles at 16p has been observed in hamartomata from TSC patients (Green and Yates, 1993; Smith et al., 1993), indicating that a second somatic mutation may be required to produce the TSC phenotype at a cellular level. This observation is consistent with the chromosome 16 TSC gene acting as a tumour suppressor, a feature shared by genes causing the other phakomatoses, neurofibromatosis type 1 (NF1) (Legius et al., 1993) and type 2 (NF2) (Trofatter et al., 1993), and von Hippel-Lindau disease (VHL) (Latif et al., 1993). If a two-hit mechanism, as proposed by Knudson (1971), does apply to TSC, then inactivating constitutional mutations would be anticipated. TSC has not been noted in individuals with the chromosome 16 α-thalassaemia/mental retardation syndrome (ATR-16) and terminal deletions of 16p which extend into the distal part of the candidate region (Wilkie et al., 1990). The inventors of the present invention therefore investigated the proximal part of the candidate region for deletions.

Some 60% of TSC cases appear to represent new mutations (Sampson et al., 1989b) and the inventors reasoned that a proportion of these might be large deletions. Such deletions, detectable by pulsed field gel electrophoresis (PFGE), would greatly facilitate identification of the gene, as has been demonstrated in NF1, NF2 and VHL (Viskochil et al., 1990; Trofatter et al., 1993; Latif et al., 1993). The inventors have now identified 5 TSC associated constitutional interstitial deletions of between 30 and 75 kb in the proximal part of the candidate region. These have been mapped to a 120 kb segment from which the inventors have identified a number of genes, one of which was disrupted by all the deletions. Mutation analysis and expression studies provide strong evidence that this gene, which we term TSC2, is the chromosome 16 tuberous sclerosis determining gene.

SUMMARY OF THE INVENTION

Accordingly, in one aspect this invention provides an isolated, purified or recombinant nucleic acid sequence comprising:

(a) a TSC2 gene or its complementary strand, (b) a sequence substantially homologous to, or capable of hybridising to, a substantial portion of a molecule defined in (a) above, (e) a fragment of a molecule defined in (a) or (b) above.

In particular, there is provided a DNA molecule having a sequence corresponding to all or a portion of the nucleotide sequence of FIG. 3 [SEQ ID NO:1], or a complementary sequence, or a sequence which hybridises to any of the above sequences.

In another aspect this invention provides a purified DNA molecule characterised as follows:

(i) it is present in the telomeric chromosomal band 16p 13.3, (ii) it is mutated in TSC patients, (iii) it lies between markers GGG1 and 16AC2.

The sequence is preferably contained in cosmids ZDS-5 and LADS-4. The DNA may be genomic but it is preferred for it to be a cDNA.

The TSC2 gene described herein is a gene found on human chromosone 16, and the results of familial studies described herein form the basis for concluding that this TSC2 gene encodes a protein called TSC2 protein or tuberin which has a role in the prevention or suppression of TSC. The TSC2 gene therefore includes the DNA sequences shown in FIG. 3 [SEQ ID NO:1], and all functional equivalents. The gene furthermore includes regulatory regions which control the expression of the TSC2 coding sequence, including promotor, enhancer and terminator regions. Other DNA sequences such as introns spliced from the end-product TSC2 RNA transcript are also encompassed. Although work has been carried out in relation to the human gene, the corresponding genetic and functional sequences present in lower animals are also encompassed.

The present invention therefore further provides a TSC2 gene or its complementary strand having the sequence according to FIG. 3 [SEQ ID NO:1]. In particular, it provides a TSC2 gene or its complementary strand having the sequence of FIG. 3 [SEQ ID NO:1], which gene or strand is mutated in some TSC patients (more specifically, TSC2 patients).

The invention further provides a nucleic acid sequence comprising a mutant TSC2 gene, especially one selected from a sequence comprising a sequence according to FIG. 3 [SEQ ID NO:1] when:

(a) [WS-13] about 32 kb are deleted flanked by CW13 and CW9;

(b) [WS-9] about 46 kb are deleted with breakpoints in SM9 and CW12;

(c) [WS-211] about 75 kb are deleted with breakpoints between CW9 and CW15 distally, and between CW23 and CW21 proximally;

(d) [WS-97] about 75 kb are deleted between BFS2 and SM9 distally, and within CW20 proximally;

(e) [WS-53] about 35 kb are deleted between, distally, CW23 next to JH1 and, proximally, such that 0.6 kb of TSC2 is deleted, the deletion lying proximally between SH6 and JH13;

(f) [WS212] about 75 kb are deleted between SM9-CW9 distally and the TSC2 3'UTR proximally as shown in FIG. 8;

(g) [WS-215] about 160 kb are deleted between CW20 and CW10-CW36 as shown in FIG. 8;

(h) [WS-227] about 50 kb are deleted between CW20 and JH11 as shown in FIG. 8;

(i) [WS-219] about 27 kb are deleted between JH1 and JH6 as shown in FIG. 8; and (j) [WS-250] about 160 kb are deleted in CW20 as shown in FIG. 8.

This invention also extends to a purified RNA molecule having a sequence corresponding to all or a portion of the nucleotide sequence of FIG. 3 [SEQ ID NO:1], or a complementary sequence, or a sequence which hybridises to any of the above sequences.

In another aspect, the invention provides a nucleic acid probe having a sequence as set out above; in particular, this invention extends to a purified nucleic acid probe which hybridises to at least a portion of the DNA or RNA molecule of any of the preceding claims. Preferably, the probe includes a label such as a radiolabel, for example a $^{32}P$ label.

In another aspect, this invention provides a purified DNA or RNA coding for a protein comprising the amino acid sequence of FIG. 3 [SEQ ID NO:2], or a protein polypeptide having homologous properties with said protein, or having at least one functional domain or active site in common with said protein.

The DNA molecule defined above may be incorporated in a recombinant cloning vector for expressing a protein having the amino acid sequence of FIG. 3 [SEQ ID NO:2], or a protein or polypeptide having at least one functional domain or active site in common with said protein.

In another aspect, the invention provides a polypeptide encoded by a sequence as set out above, or having the amino acid sequence according to the amino acid sequence of FIG. 3 [SEQ ID NO:2], or a protein or polypeptide having homologous properties with said protein, or having at least one functional domain or active site in common with said protein. In particular, there is provided an isolated, purified or recombinant polypeptide comprising a TSC2 protein or a mutant or variant thereof or encoded by a sequence set out above or a variant thereof having substantially the same activity as the TSC2 protein.

This invention also provides an in vitro method of determining whether an individual is likely to be affected with tuberous sclerosis, comprising the steps of assaying a sample from the individual to determine the presence and/or amount of TSC2 protein or polypeptide having the amino acid sequence of FIG. 3 [SEQ ID NO:2].

Additionally or alternatively, a sample may be assayed to determine the presence and/or amount of mRNA coding for the protein or polypeptide having the amino acid sequence of FIG. 3 [SEQ ID NO:2], or to determine the fragment lengths of fragments of nucleotide sequences coding for the protein or polypeptide of FIG. 3 [SEQ ID NO:2], or to detect inactivating mutations in DNA coding for a protein having the amino acid sequence of FIG. 3 [SEQ ID NO:2] or a protein having homologous properties.

A method according to the present invention may comprise detecting a TSC2-associated disorder in a patient suspected of having or having predisposition to, said disorder, the method comprising detecting the presence of and/or evaluating the characteristics of TSC2 DNA, TSC2 mRNA and/or TSC2 protein in a sample taken from the patient. Such method may comprise detecting and/or evaluating whether the TSC2 DNA is deleted, missing, mutated, aberrant or not expressing normal TSC2 protein. One way of carrying out such a method comprises:

A. taking a biological, tissue or biopsy sample from the patient;

B. detecting the presence of and/or evaluating the characteristics of TSC2 DNA, TSC2 mRNA and/or TSC2 protein in the sample to obtain a first set of results;

C. comparing the first set of results with a second set of results obtained using the same or similar methodology for an individual not suspected of having said disorders; and if the first and second sets of results differ in that the TSC2 DNA is deleted, missing, aberrant, mutated or not expressing TSC2 protein then that indicates the presence, predisposition or tendency of the patient to develop said disorders.

A specific method according to the invention comprises extracting a sample of TSC2 DNA or DNA from the TSC2 locus purporting to be TSC2 DNA from a patient, cultivating the sample in vitro and analysing the resulting protein, and comparing the resulting protein with normal TSC2 protein according to the well-established Protein Truncation Test.

Less sensitive tests include analysis of RNA using RT PCR (reverse transcriptase polymerase chain reaction) and examination of genomic DNA.

On the other hand, if step C of the method is replaced by:

C. comparing the first set of results with a second set of results obtained using the same or similar methodology in an individual known to have the or at least one of said disorder(s); and if the first and second sets of results are substantially identical, this indicates that the TSC2 DNA in the patient is deleted, mutated or not expressing normal TSC2 protein.

The invention further provides a method of characterising a mutation in a subject suspected of having a mutation in the TSC2 gene, which method comprises:

A. amplifying each of the exons in the TSC2 gene of the subject;

B. denaturing the complementary strands of the amplified exons;

C. diluting the denatured separate, complementary strands to allow each single-stranded DNA molecule to assume a secondary structural conformation;

D. subjecting the DNA molecule to electrophoresis under non-denaturing conditions;

E. comparing the electrophoresis pattern of the single-stranded molecule with the electrophoresis pattern of a single-stranded molecule containing the same amplified exon from a control individual which has either a normal or TSC2 heterozygous genotype; and F. sequencing any amplification product which has an electrophoretic pattern different from the pattern obtained from the DNA of the control individual.

The invention also extends to a diagnostic kit for carrying out a method as set out above, comprising nucleic acid primers for amplifying a fragment of the DNA or RNA sequences defined above.

Another embodiment of kit may combine one or more substances for digesting a sample to provide EcoRI fragments and a DNA probe as previously defined.

Still further, a kit may include a nucleic acid probe capable of hybridising to the DNA or RNA molecule previously defined.

The protein (tuberin) described herein may be used to treat patients affected by or likely to be affected by TSC2-associated disorder such as tuberous sclerosis (TSC). Thus the protein or a polypeptide or hybrid protein having a homologous function to the protein may be administered to a patient to alleviate or avoid the effects of a TSC2-associated disorder.

As described hereinbelow, it is believed that TSC2 and the tuberin protein are involved in preventing the development of cancers in patients with or without TSC. Accordingly, the present invention further provides a method for suppressing tumour development or preventing unrestrained cell division or treating a TSC2-associated tumour which method comprises providing a functional TSC2 gene to the desired cells of the patient such as to allow expression of tuberin therein or by providing tuberin or a tuberin functional mimic (e.g. a hybrid protein having a homologous function) therein, in an amount sufficient to have the desired effect such as a cell growth regulating or tumour suppressing effect.

The invention extends to any inventive combination of the features described above or in the following description.

BRIEF DESCRIPTION OF THE DRAWINGS

FIG. 4 shows the homology between the predicted protein sequence of tuberin (amino acids 1593–1631) [SEQ ID NO:2] and amino-terminal domains of Human GAP3 [SEQ ID NO:3] and Murine GAP [SEQ ID NO:4]

FIGS. 7a–c are the results of analysis of the five small deletions affecting TSC2 represented in the restriction map of FIG. 5.

FIG. 1 is a map of the terminal region of chromosome 16p and shows the TSC2 candidate region determined by linkage analysis between MS205.2 (D16S309) and 16AC2.5 (D16S291). The size of the terminal deletion found in ATR-16 patient BO is shown (top) (Summarised from Harris et al., 1990; Harris et al., 1991; Germino et al., 1992; Rack et al., 1993; Wilkie et al., 1990; Germino et al., 1993 and Kwiatkowski et al., 1993). Expanded below is a detailed map of the proximal TSC2 candidate region showing the ClaI (C) sites, the breakpoints of the two somatic cell hybrids N-OH1 and P-MWH2A and the positions of existing and selected new DNA probes. The positions of cosmids within the contig are shown below the map: 1, JCI; 2, JCII; 3, CC1; 4, CC1–2; 5, CBFS1; 6, CW9D; 7, LADS4; 8, CW12I; 9, JH1K; 10, ZDS5; 11, SMII.

In FIG. 2, a detailed map of the TSC area of chromosome 16, genomic sites for the enzymes BssHII, B; MluI, M; NotI, N; NruI, R; SacII, S and a partial map of EcoRI (E) sites are shown. The open boxes indicate the size and location of genomic probes (see Experimental Procedures for details). The solid boxes show the sizes of transcripts and their orientations on the chromosome are marked with arrows. The genomic extent of each gene is indicated with brackets. The full proximal extent of 3A3 is unknown. cDNA clones comprising the TSC2 gene are shown enlarged below. The size and location of TSC-associated deletions are shown above the map with dashed lines indicating regions of uncertainty. The WS-13 deletion is 32 kb and flanked by CW13 and CW9. A 7 kb EcoRI breakpoint fragment is seen with these two probes (FIG. 3c). WS-9 is a 46 kb deletion with the breakpoints in SM9 and CW12. An 8 kb EcoRI breakpoint fragment is seen with these probes. The WS-211 deletion is ¯75 kb and the breakpoints lie between CW9 and CW15 distally, and between CW23 and CW21. The distal breakpoint of WS-97 is between BFS2 and SM9 and proximally within CW20, with a region of approximately 75 kb deleted. The WS-53 deletion is ¯35 kb and the distal breakpoint lies within CW23, proximal to JH1. The proximal 0.6 kb of TSC2 is deleted. The exact location of the proximal breakpoint of WS-53 is unknown.

In FIG. 3, the predicted protein [SEQ ID NO:2] is shown below the DNA sequence, assuming that translation begins at the first in-frame methionine of the long open reading frame. The cross-hatched grey bar denotes the GAP3 related domain (amino acids 1593–1631). The double underlining marks the possible membrane spanning regions. The dotted line indicates a potential leucine zipper starting at amino acids 81. r__r indicates the repeated motif H A V E/L A L W/L K A at amino acid 76–84 and 99–107. Possible N-linked glycosylation sites (@) are marked at amino acids 1037, 1205, 1499, and 1628. Serine (S) and threonine (T) residues that are potentially phosphorylated by cAMP-and cGMP- dependent protein kinases (upward arrowheads) (Glass et al., 1986), protein kinase C (right arrowheads) (Woodgett et al.,1986), or casein kinase 2 (downward arrowheads) (Pinna, 1990), and possible tyrosine (Y) kinase phosphorylation sites (#) (Patschinsky et al., 1982) are indicated. Two potential polyadenylation signals at bases 5425 and 5429 (underlined) and polyadenylation cleavage sites are indicated (^). Cleavage occurs immediately before or after the marked base.

In FIG. 4, identical amino acids are boxed. Asterisks indicate identical, or interchangeable amino acids, which are shared between tuberin and at least one of the GAP proteins. Interchangeable amino acids were identified using the criteria of Dayhoff et al (1978). The GenBank Accession number for the Homo Sapiens tuberin mRNA sequence is X75621.

In FIG. 5, Genomic probes (CW26, CW12, CW18) and cDNA probes (EO.5, E1.6, EO.7, E2.5) are represented by solid bars, and the position of 5 small deletions (hatched bars) affecting the gene. Exonic EcoRI sites and the 5' and 3' ends of the gene are linked to the genomic map by the diagonal lines.

FIG. 6 panels A–C shows:

(a) PFGE of MluI-digested DNA from TSC patients and controls probed with the clones CW21 (WS-9. WS-13. WS-97) and JH1 (WS-53), which detect an ⁻120 kb fragment in normal individuals (N) and additional smaller fragments in the patients. CW21 is deleted in patient WS-53 and so does not recognise the aberrant ⁻90 kb fragment. The WS-97 deletion removes ⁻75 kb including the distal MluI site, producing an ⁻74 kb junction fragment (see FIG. 2).

(b) PFGE of NruI-digested DNA of a normal control (N) and WS-211 (211) hybridized with probes flanking the breakpoint at the distal end (CW9 and CW15) and at the proximal end (CW23 and CW21) of the deletion. As well as the normal ⁻150 kb fragment, the same ⁻80 kb breakpoint fragment (shown by an arrow) is seen, with the two markers outside of the deletion (CW9 and CW21). CW15 is completely deleted (no breakpoint fragment), while CW23 is mostly deleted, although a faint ⁻80 kb fragment can be seen in the WS-211 track.

Figure 2:
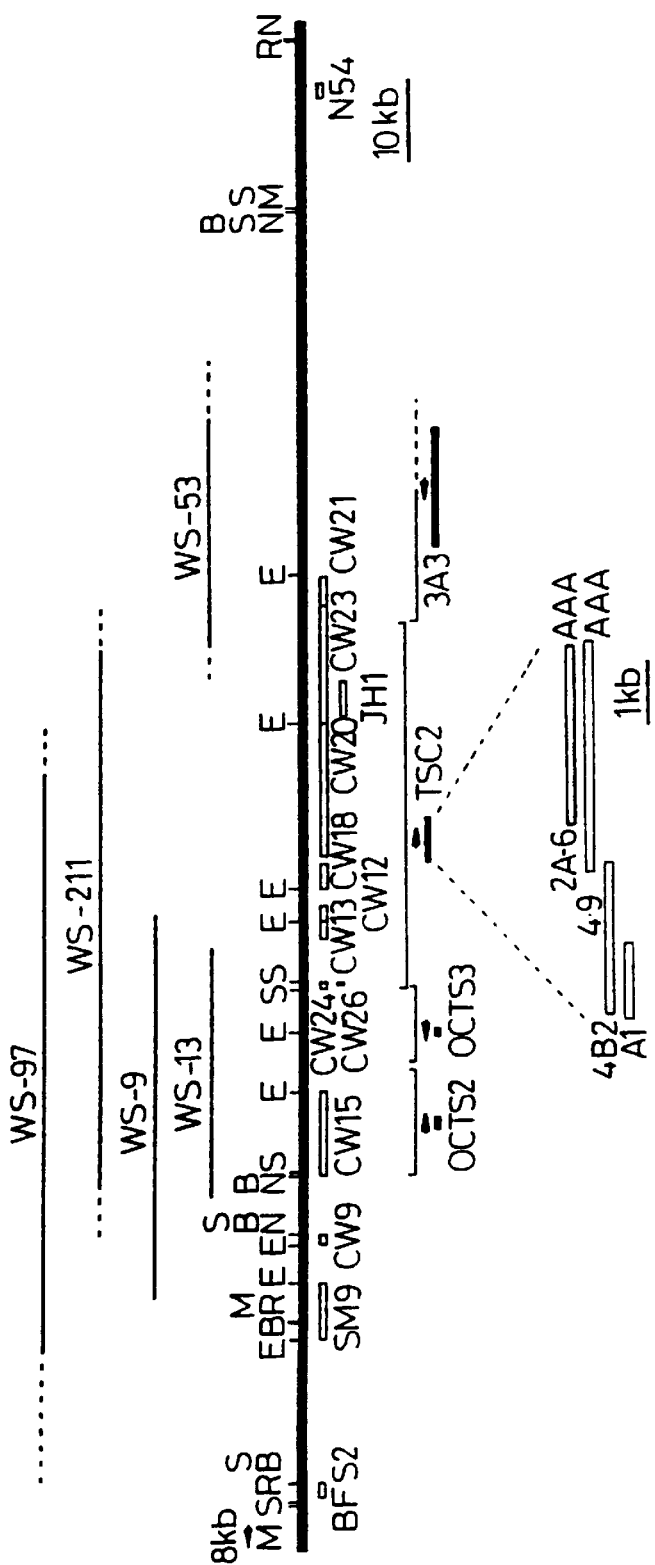
FIG. 2 is a detailed map of the TSC area of chromosome 16.

(c) EcoRI-digested DNA of normal control (N) and WS-13 (13) separated on a conventional gel and hybridised with probes (CW9 and CW13) which flank the deletion (see FIG. 2). The same 7 kb breakpoint fragment (shown by arrows) is seen with both markers, consistent with a deletion of 32 kb, ending within the EcoRI fragments seen by these probes.

FIG. 7 shows:

(a) Southern blot analysis in cases 5773 and 1737. HindIII- and BamHI-digested DNAs from the patients (P) and an unrelated control (N) were hybridised with cDNA probe E 0.7. This probe detects adjacent HindIII fragments of ⁻14 kb and 2.5 kb and a single BamHI fragment of ⁻14 kb. In case 5773, a deletion of ⁻1 kb within the BamHI fragment removes a HindIII site to produce a junction fragment of ⁻16 kb. The ⁻4 kb deletion in case 1737 produces novel HindIII and BamHI fragments of ⁻10 kb. Adjacent fragments were normal.

(b) Southern blot analysis of the de novo deletion in case WS-11. EcoRI-digested DNA from the patient (11), father (F) and mother (M) was hybridised with probes E 0.7, CW12, E1.6 and CW18. E0.7 detects the normal 18 kb fragment in WS-11 and both parents and an additional 17 kb fragment in WS-11 alone. CW12 detects the normal 4 kb fragment in WS-11 and both parents and the additional 17 kb fragment in WS-11 alone, demonstrating that the 17 kb fragment E1.6 spans the EcoRI site that is deleted in formation of the junction fragment and so detects both normal fragments of 4 kb and 18 kb and the 17 kb junction fragment. CW18 is deleted on the mutant chromosome and so fails to detect the junction fragment. A HindIII junction fragment and novel small BamHI fragment were also seen by Southern analysis, and probes recognising a variable number of tandem repeat polymorphisms were used to confirm biological parentage (data not shown).

(c) The TSC2 cDNA clone 2A6 hybridised to a Northern blot containing 1 g of lymphocyte mRNA from a normal control (N) and TSC patient WS-11 (11), who has an intragenic genomic deletion (see [b]). An additional transcript (shown by an arrowhead) ⁻1 kb smaller than normal is seen in WS-11.

Figure 8:
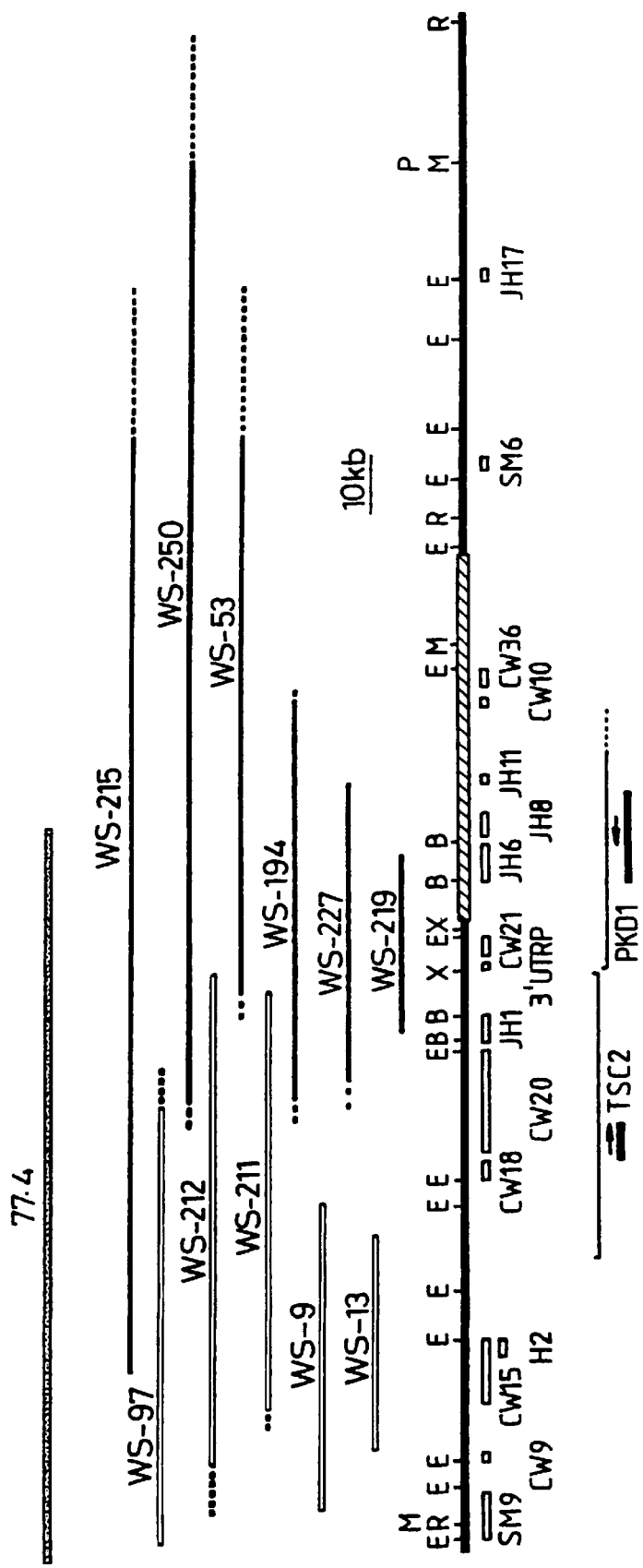
FIG. 8 is a map of the TSC2 and PKD1 region of chromosome 16.

FIG. 8 shows genomic sites for the enzymes MluI (M), ClaI (C), PvuI (P) and NruI (R) are shown. Positions of single copy probes and cosmids used to screen for deletions are shown below the line which represents ⁻400 kb of genomic DNA. The genomic distribution of the approximately 45 kb TSC2 gene and known extent of the PKD1 gene are indicated above. The hatched area represents an ⁻50 kb region which is duplicated more proximally on chromosome 16p.

DETAILED DESCRIPTION OF THE DRAWINGS

Deletions in The TSC Candidate Region

Figure 1:
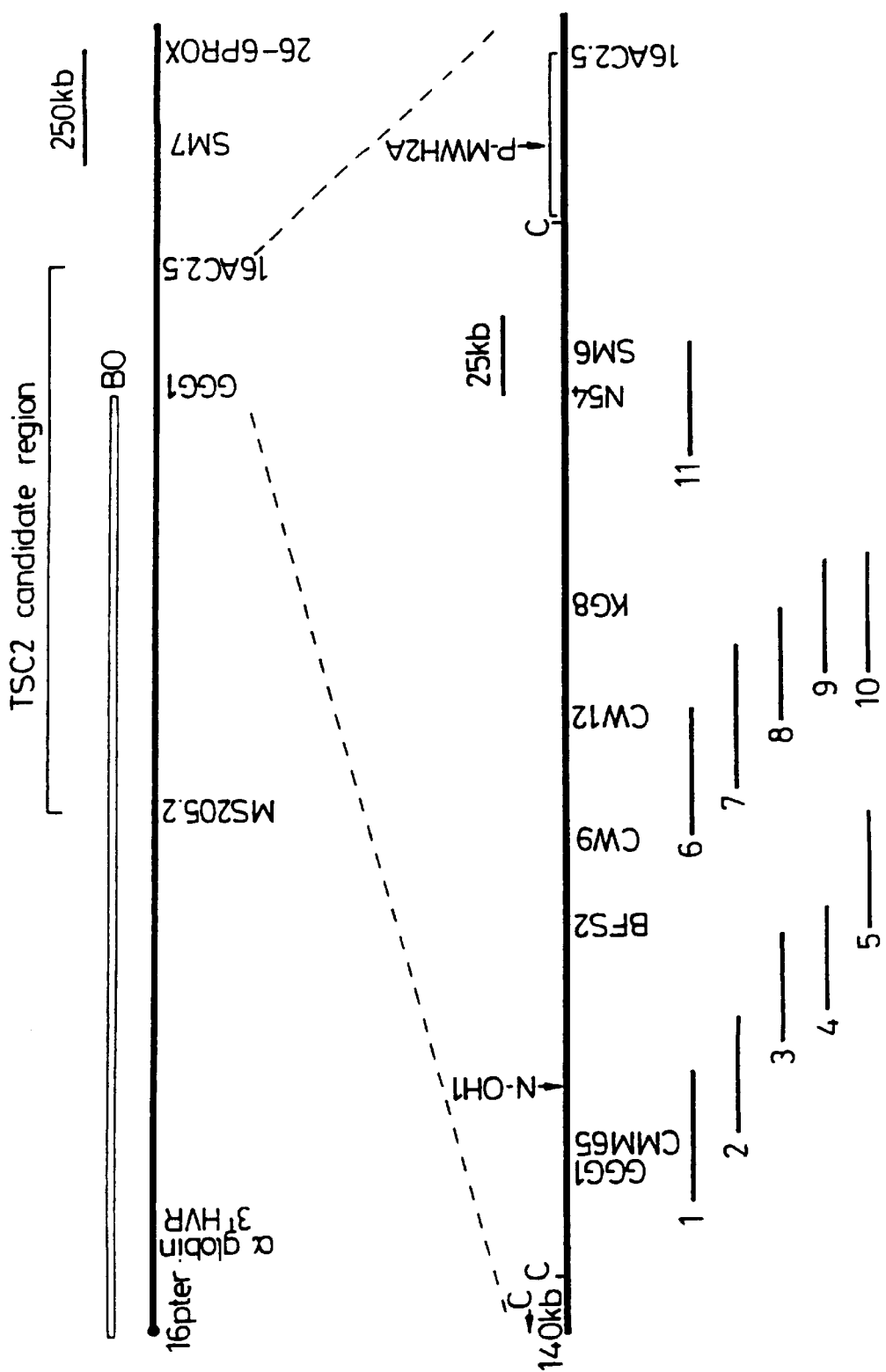
FIG. 1 is a physical map of chromosome 16 pter.

An ATR-16 patient (BO), with a constitutional deletion at 16p (Wilkie et al., 1990) which extends into the TSC candidate region (FIG. 1), was specifically reassessed for signs of TSC (by clinical evaluation, renal ultrasound and cranial CT imaging) but with negative results. The inventors decided to focus their search for TSC associated deletions on the more proximal part of the candidate region, most of which is spanned by a ClaI restriction fragment of approximately 340 kb (Germino et al., 1992, Harris et al., 1990). Using pulsed field gel electrophoresis (PFGE) this fragment was assayed in 255 unrelated TSC patients with SM6, a single copy probe isolated from cosmid SMII (FIG. 1). The patients all fulfilled definitive diagnostic criteria as defined by Gomez (1988). Aberrant smaller fragments consistent with constitutional interstitial deletions were observed in 5 cases. As these changes were likely to involve the TSC gene, the inventors decided to characterise further the region containing the deletions.

Mapping of PFGE Deletions and Genomic Cloning

Cosmid walking was initiated from the previously defined loci JCII and N54 (Germino et al., 1990; Himmelbauer et al., 1991). The proximally directed walk established a series of overlapping clones spanning 200 kb across the area of the TSC associated deletions, while the distally directed walk was hampered by a duplicated region homologous to sequences more proximal on 16p (Germino et al., 1992). A long range restriction map was constructed in genomic and cloned DNA which was consistent in size with that produced by Germino et al. (1992) although additional sites for NruI and MluI were identified. Mapping of SacII and BssHII sites enabled the unmethylated CpG islands to be located (FIG. 2). The area was precisely mapped with EcoRI and other restriction enzymes and many fragments were subcloned (FIG. 2 and Experimental Procedures for details).

The sizes and positions of the five TSC deletions were more accurately determined by analysing MluI and NruI digested DNA. Successive hybridisations enabled fragments flanking or containing the deletion breakpoints to be identified. When suitable material was available a breakpoint fragment was identified in EcoRI, BamHI and/or HindIII digests with probes immediately flanking the deletion, confirming the nature of the rearrangement. The precise position of each of the TSC deletions is summarised in FIG. 2. Two deletions estimated at 32 kb and 46 kb, and two of at least 70 kb were positioned distally and overlapped one another extensively. A fifth deletion of approximately 35 kb was more proximally situated and was shown to be non-overlapping with at least 3 of the distal deletions (FIG. 2). As each of these deletions was likely to involve part of the chromosome 16 TSC gene, a candidate gene that mapped into all of them was sought.

Genes in the Region Harbouring Pulsed Field Deletions

Subcloned probes and fragments from cosmids spanning the region of the TSC associated deletions were used to screen human foetal brain and human kidney cDNA libraries. The mapping of positive clones to the target area was confirmed by hybridisation to panels of somatic cell hybrids, containing derivative 16 chromosomes with breakpoints flanking this region; N-OH1, distal, and P-MWH2A, proximal (FIG. 1), and a radiation hybrid Hy145.19 which contains this area, as a positive control. Northern blot analysis using RNAs from various human cell lines indicated that the clones derived from four apparently unrelated genes. Hybridisation of the cDNA clones to digests of cosmid, genomic and hybrid DNA indicated the genomic distributions of the genes. Sequence analysis identified the polyA tail of each gene and established their transcriptional orientations.

A gene, termed OCTS2, with a transcript of 1.7 kb (cDNA clones OCTS2C and RCTS2) and a second gene termed OCTS3 with a 1 kb transcript (cDNA clone OCTS3C) mapped entirely within the four distal deletions, but did not extend as far as the proximal deletion in patient WS-53 (FIG. 2). A 15 kb transcript was recognised by two cDNA clones, 3A3 and AH4, and was termed 3A3. It mapped partly within the WS-53 deletion. Since the distal clone AH4 contained the polyA tail, the gene is transcribed from centromere to telomere and does not extend towards the distal deletions (FIG. 2).

The cDNA clones 2A6 and 4.9 detect an ⁻5.5 kb transcript and were identified using an 18 kb EcoRI fragment from cosmid ZDS5 (corresponding to the region subcloned in CW23 and CW21). A transcript of the same size was detected by CW26, a genomic probe which maps at a CpG island located within the four distal deletions (FIG. 2). By means of a cDNA walk the 2A6 and 4.9 clones were connected to clones 4B2 and A1 which mapped to the CW26 region confirming that this single gene is disrupted by all five PFGE deletions. This gene was therefore designated TSC2 and characterised in detail.

TSC2 Expression

Northern blot analysis indicates that TSC2 is widely expressed with the 5.5 kb transcript seen in all cell lines tested, including those derived from brain, kidney, skin, liver, adrenal gland, colon and white blood cells. Expression has also been seen in all tissues tested, including liver, kidney and heart, and in lymphocytes, fibroblasts and biliary epithelium. The high level of TSC2 expression in fibroblasts made it possible to compare the level of transcription in fibroblasts derived from normal controls and TSC patients. In one family in which TSC has been shown to co-segregate with chromosome 16p13.3 markers, but in which the mutation has not been identified, the affected members showed clearly reduced levels of TSC2 transcript. Transcripts from adjacent genes showed unaltered levels of expression.

The combination of non-overlapping PFGE deletions affecting TSC2 and the reduced expression of the TSC2 transcript in TSC patients strongly suggests that the deletions inactivate the structural TSC determining gene rather than a regulatory element for a remote gene. To confirm that TSC2 is indeed a TSC determining gene we sought independent intragenic mutations.

Intragenic Mutations Affecting TSC2

Figure 5:
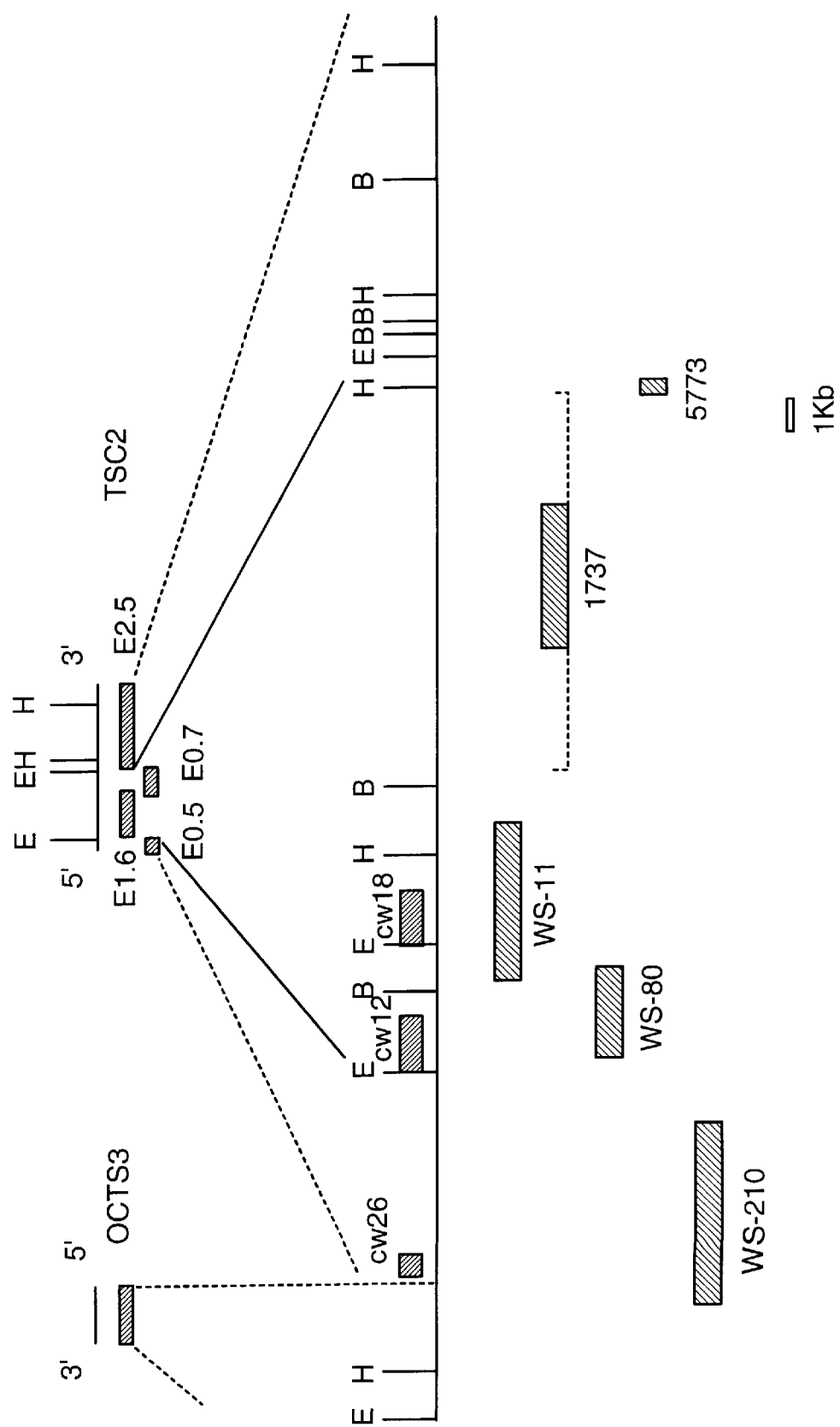
FIG. 5 is a restriction map to show the genomic distribution of TSC2.
Figure 6A:
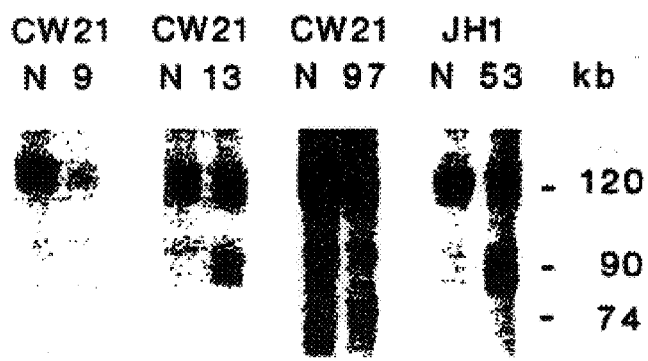
FIG. 6 is the result of PFGE analysis of deletions in TSC individuals.
Figure 6B:
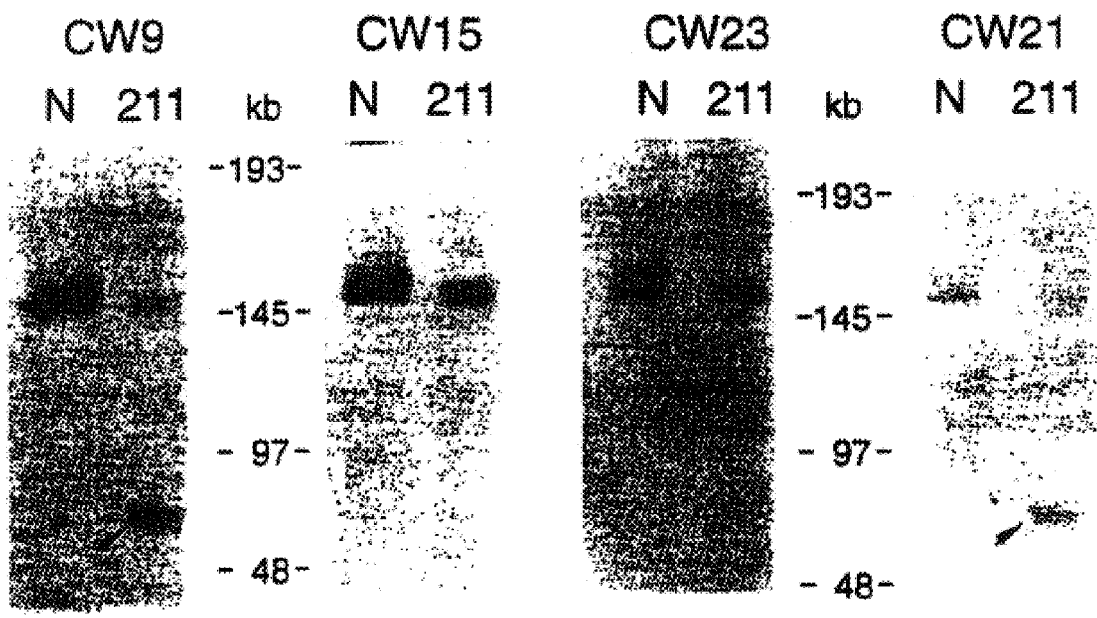
Figure 6C:
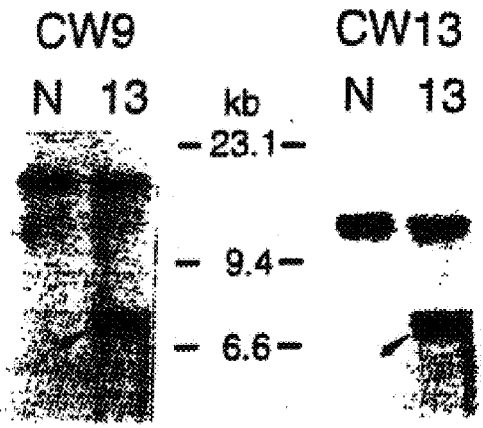

DNA samples from 260 unrelated TSC patients were screened for confirmatory rearrangements within TSC2 using cDNA sub-clones as hybridisation probes. All patients tested fulfilled the definitive diagnostic criteria of Gomez (1988) and included many of those previously studied by PFGE. In addition to those cases in which PFGE abnormalities had been found, aberrant bands were noted with multiple restriction enzymes in a further 5 patients. Southern analysis using a combination of genomic clones and small cDNA fragments as hybridisation probes demonstrated that these changes represented small deletions. The position of each deleted segment was confirmed relative to the genomic map of EcoRI, HindIII and BamHI sites (FIG. 5). The most 5' deletion found in patient WS-210, was not entirely intragenic as it also involved the OCTS3 gene. The deletion spans 5–6 kb and removes the genomic Rrobe CW26 which contains TSC2 coding sequence. All four other deletions were shown to be entirely within TSC2. A deletion of approximately 1kb in patient 5773 was shown to remove an intronic HindIII site. In this case the mutation was also detected in the affected parent. In two further cases (WS-80 and 1737) deletions of approximately 3 kb and 5 kb respectively were identified. The parents of these cases were thought to be unaffected but were not available for analysis, making it impossible to confirm that the changes represented de novo mutations. In contrast, both clinically unaffected parents of patient WS-11 were available for analysis and the ⁻5 kb deletion (which was not seen on PFGE) was shown to represent a de novo mutation. The deletion removes an intronic HindIII site and the upstream intronic EcoRI site. The genomic probe CW18, which lies between these sites and detects the TSC2 transcript, was shown to be deleted. Leucocyte polyA RNA prepared from this patient showed an abnormal TSC2 transcript of ⁻4.5 kb on Northern analysis. Together these findings confirm that TSC2 is the chromosome 16 tuberous sclerosis determining gene.

Further Deletions Involving TSC2

Deletions involving both TSC2 and PKD1 were identified and characterized in six patients in whom TSC was associated with infantile polycystic kidney disease. As well as the deletion in WS-53, those in WS-215 and WS-250 also extended proximally well beyond the known distribution of PKD1 and probably delete the entire gene. The deletion in WS-194 extended over the known extent of PKD1, but not much further proximally, while the proximal breakpoints in WS-219 and WS-227 lay within PKD1 itself. Northern analysis of case WS-219 with probe JH8, which lies outside the deletion, showed a reduced level of the PKD1 transcript but no evidence of an abnormally sized transcript (data not shown). Analysis of samples from the clinically unaffected parents of patients WS-53, WS-215, WS-219, WS-227 and WS-250 showed the deletions in these patients to be de novo. The father of WS-194 was unavailable for study.

In a further case (WS-212), renal ultrasound showed no cysts at four years of age but a deletion was identified which removed the entire TSC2 gene and deleted an XbaI site which is located 42 bp 5' to the polyadenylation signal of PKD1.

Characterisation of TSC2

Figure 3:
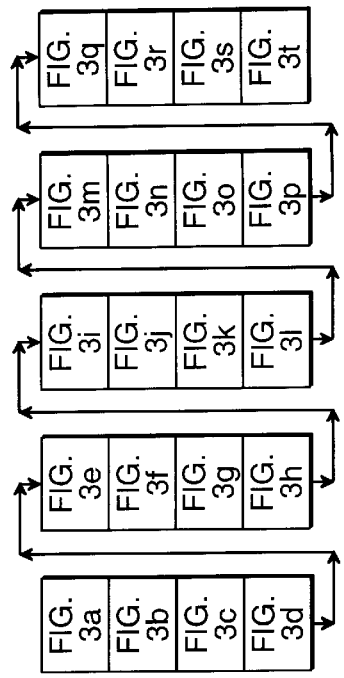
FIG. 3 is the nucleotide sequence (cDNA) of TSC2 gene [SEQ ID NO:1] and its predicted protein [SEQ ID NO:2]

To further characterise the TSC2 gene, evolutionary conservation was studied and sequence analysis was performed. A 'zoo-blot' containing genomic DNA from various animal species revealed that the TSC2 gene was conserved throughout the higher vertebrates. Strong signals were obtained from primates and signals indicating lower homology were obtained from several other vertebrates, including rodents, marsupial and reptile. No signal was obtained from fish or non-vertebrate species. The TSC2 transcript was sequenced completely in both strands. All sequence was confirmed in at least two independent cDNA clones. The coding sequence obtained extends 5474 bp [SEQ ID NO:1] (FIG. 3). Despite repeated cDNA library rescreening, no clones extending further 5' could be identified. The available sequence approximates to the transcript size determined by Northern blot analysis. The cDNA contains an open reading frame (ORF) extending from nucleotide 1 through 5370. The second-best ORF is no more than 402 bp. At nucleotide position 19 we found an in-frame start codon, matching the Kozak consensus (Kozak, 1987). At the 3' end we noted two partially overlapping polyadenylation signals (AATAAATAAA) at nucleotide 5425. The occurrence of this doublet may cause differential polyadenylation, since we found polyadenylation sites which differ by up to 15 bp in four different cDNA clones. The total length of the predicted protein [SEQ ID NO:2] is 1784 amino acids with a calculated molecular mass of 198 Kd. There is no apparent signal peptide or signal peptidase cleavage site. Using the method described by Eisenberg et al. (1984), we identified hydrophobic domains, four of which may represent membrane spanning regions. Within a predicted alpha-helical structure, a stretch of 22 amino acids, surrounded by a repeated motif of 9 amino acids, complied with the leucine zipper consensus (Landschulz et al., 1988). A search for sequence homologies at protein level revealed a region of similarity between the predicted product of TSC2 and the GTPase activating protein GAP3 (or rap1GAP) (Rubinfeld et al., 1991). The region extends over 58 amino acids and the level of residue identity fulfils the criteria of Sander and Schneider (1991) for structural homology. Of the first 39 amino acids, 14 are identical with murine GAP and with human GAP3. A core stretch of 17 residues contains identical or similar amino acids with only one mismatch (FIG. 4).

Discussion

The inventors have used a positional cloning strategy to identify a gene on chromosome 16 which is mutated in tuberous sclerosis. A number of questions concerning the biology of TSC and its relationship to other disorders can now be addressed. The TSC2 gene maps within the candidate region for the unidentified PKD1 gene, causing autosomal dominant polycystic kidney disease type 1 (ADPKD1), as defined by Germino et al. (1992). As polycystic kidneys are a feature common to TSC and ADPKD1 (Bernstein and Robbins, 1991) the possibility of an aetiological link, as proposed by Kandt et al. (1992), must be considered. Renal cysts, however, have been reported in a chromosome 9-linked TSC family (Nellist et al., 1993) and their presence is therefore not limited to chromosome 16-linked TSC. Furthermore, while TSC and ADPKD1 cysts are macroscopically similar, the epithelium lining TSC associated cysts is usually considered to be histologically distinct (Bernstein et al., 1974). Despite these observations it may be tempting to hypothesise that chromosome 16-linked forms of TSC and ADPKD1 are allelic variants. However, the inventors have not found any evidence that this is the case. The search for possible functional motifs in the sequence of the predicted protein, which the inventors have called tuberin, indicates several regions of interest. Four hydrophobic domains were identified which may be involved in membrane anchorage and four potential glycosylation sites were observed downstream of the last putative transmembrane domain. No sequence at the amino-terminus of the predicted protein matched the signal peptide structure as defined by von Heijne (1985). However, the occurrence of several transmembrane domains without an apparent signal peptide was noted in the cystic fibrosis-related protein CFTR (Riordan et al., 1989). We also noted a periodic array of leucine residues (leucine zipper), a structure associated with protein-protein interaction. Experiments are in progress to determine the cellular localisation of tuberin, which will provide insight into the functional significance of the sequence motifs that have been identified. Because of the highly variable TSC phenotype, the genetic status of a patient's relatives may remain uncertain, even after extensive diagnostic investigation (Al-Gazali et al., 1989; Fryer et al., 1990). In this situation the identification of the causative mutation would be very helpful. Although a relatively small number of mutations are reported in this study, alternative approaches such as SSCP analysis (Orita et al., 1989) can be applied now that the TSC2 gene sequence is available. Identification of the TSC1 gene on chromosome 9 will also have to be achieved before the full mutational spectrum in TSC and the practicalities of DNA based diagnostics can be completely evaluated. The inventors have identified multiple deletional mutations affecting different parts of the TSC2 gene in unrelated TSC patients. This pattern, and the reduced expression of TSC2 seen in affected individuals, suggest that constitutional mutations in TSC are likely to be inactivating. The patchy focal nature of TSC associated lesions and the loss of heterozygosity which they exhibit (Green and Yates, 1993) suggest that reduction to the homozygous null state is required before cellular growth and differentiation become disordered. A similar combination of inactivating constitutional and somatic mutations have been clearly demonstrated in the Rb gene in retinoblastoma (Horowitz et al., 1989) and more recently the NF1 gene in neurofibrosarcoma (Legius et al., 1993); it has also been proposed in NF2 (Rouleau et al., 1993) and VHL (Latif et al., 1993). It would seem likely, therefore, that TSC2 also behaves as a tumour suppressor gene as defined by Knudson's theory of carcinogenesis (Knudson, 1971). In view of these observations it is interesting that tuberin contains a region of homology to GAP3, which enhances the GTPase activity of p21rap1, a GTP binding protein thought to antagonise p21ras. The area of homology lies within a region known to be necessary for the catalytic activity of GAP3 (Rubinfeld et al., 1992). It seems possible that tuberin may have GAP activity for p21rap1 or another GAP protein involved in the control of cellular proliferation and differentiation. An analogous situation has already been demonstrated in NF1, where the normal regulation of p21ras is disrupted by mutations affecting, the rasGAP homologue neurofibromin (Xu et al., 1990 and Martin et al., 1990). As the proteins involved in the various phakomatoses are identified, their functions and possible inter-relationships will be established.

Experimental Procedures

Pulsed Field Electrophoresis

High molecular weight DNA was isolated from peripheral blood in agarose plugs by standard methods (Hermann et al., 1987) and digested according to the manufacturers recommendations. Blocks were loaded into the wells of 1% agarose gels and electrophoresis carried out using a BioRad CHEF DR II or a similar apparatus and programs appropriate to the varying resolutions required.

Southern Blot Analysis

Genomic DNA was extracted from peripheral blood by standard methods. 5–8$\mu$g DNA was digested with restriction enzymes, electrophoresed through agarose gels and blotted to nylon filters as described (Sambrook et al., 1989). Probes were labelled by the random-primer method (Feinberg and Vogelstein, 1984). For probes containing repetitive elements, long of labelled DNA was pre-associated with 0.1–1 mg denatured sonicated total human DNA in a total volume of 200 $\mu$l at 650C. for 1–5 hr. prior to hybridisation. If required filters were additionally prehybridized with 100 $\mu$g/ml denatured sonicated total human DNA and salmon sperm DNA. Filters were hybridised, washed as described (Sambrook et al., 1989) and exposed to autoradiographic film with an intensifying screen at −70° C.

DNA Probes and Somatic Cell Hybrids

Some of the probes used in this study have been described previously: MS205.2 (D16S309; Royle et al., 1992); GGG1 (D16S259; Germino et al., 1990); 16AC2.5 (D16S291;

Thompson et al., 1992) and N54 (D16S139; Himmelbauer et al., 1991). A number of new probes were also isolated during the course of this study: SM6, a 2.3 kb Sau3A fragment from SMII; BFS2, a 1.8 kb BssHII fragment of CC1-2; SM9, a 7 kb EcoRI fragment of CBFS1; CW9 a 1kb EcoRI/NotI segment of CBFS1; CW15 a 10 kb EcoRI/NotI fragment of CW9D; CW24 and CW26 are 0.9 kb and 0.4 kb, SacII and SacII/SacI fragments, respectively, of CW9D; CW13 and CW12 are EcoRI/NotI fragments of 2.2 kb and 2.0 kb, respectively, from CW9D; CW18, CW20 are EcoRI/NotI fragments of 3 kb and 16 kb respectively from CW12I, JH1, a 4.4 kb BamHI fragment of CW12I; and CW23 and Cw21 are 14 kb and 3.5 kb NotI/EcoRI fragments, respectively, of JHIK. All new probes except SM6, BFS2, CW26 and CW21 contain repetitive sequences and were hybridised in the presence of denatured, sonicated human DNA (75 ug/ml) and washed in 0.05×SSC, 0.2% SDS at 650C.

The somatic cell hybrid N-OH1 and the radiation hybrid, Hy145.19 have been described previously (Germino et al, 1990; Himmelbauer et al, 1991). The P-MWH2A hybrid contains the derivative chromosome 16qter—16p13.3::7q32—7qter and was isolated from a subject, MW, who has a balanced translocation. P-MWH2A was produced by fusing lymphoblastoid cells from MW with APRT deficient mouse erythroleukemia cells by the method of Deisseroth and Hendrick (1979). The breakpoint in this hybrid has been localised to the region between 16AC2.5 and the adjacent ClaI site (see FIG. 1).

RNA Isolation and Northern Blot Analysis

RNA was extracted from cell-lines and tissues by the acid phenol method of Chomczynski and Sacchi (1987). mRNA was isolated from total RNA using a biotinylated oligo (dT) primer and streptavidin coupled paramagnetic particles (PolyATtract mRNA Isolation System, Promega). RNA was separated in denaturing formaldehyde gels and Northern blotted by standard procedures. Hybridisation and washing of Northern blots was as described for Southerns.

Cosmid Walking

Cosmids were obtained from several different libraries: Los Alamos Chromosome 16 specific library (Stallings, et al. 1990) and total genomic cosmid libraries 412 and IG328 (Integrated Genetics) and 961200 (stratagene). Successive cosmid walks were made by mapping each cosmid, isolating end clones and rehybridising the libraries using conditions to repress repetitive sequences if necessary. A cosmid/genomic EcoRI map was produced and the location of cosmids was checked by mapping on hybrid panels, PFGE and fluorescence in situ hybridisation.

cDNA Isolation and Characterisation

Screening for cDNAs was performed using standard phage plating, filter lift and clone purification techniques in commercial libraries derived from human fetal brain (Clonetech, Stratagene) and human adult kidney (Clonetech). Filters were lifted as described by Sambrook (Sambrook, 1989). Repetitive sequences were suppressed as described above. After overnight hybridisation at 650C, filters were washed as described (Sambrook, 1989). All positive clones were subcloned into one of the pBluescript or pUC vectors and sequenced with a Pharmacia A.L.F. or ABI model 373A automated sequencer according to the manufacturers protocol, or manually.

References

Al-Gazali, L. I., Arthur, R. J., Lamb, J. T., Hammer, H. M., Coker, T. P., Hirschmann, P. N., Gibbs, J., and Mueller, R. F. (1989). Diagnostic and counselling difficulties using a fully comprehensive screening protocol for families at risk for tuberous sclerosis. J. Med. Genet. 26, 694–703.

Bernstein, J., Brough, A. J., and McAdams, A. J. (1974). The renal lesion syndromes of multiple congenital malformations: cerebrohepatorenal syndrome; Jeune asphyxiating thoracic dystrophy; tuberous sclerosis; Meckel syndrome. Birth Defects: Original Article Series, 10, 35–43.

Bernstein, J. and Robbins, T. O. (1991). Renal involvement in tuberous sclerosis. Ann. N. Y. Acad. Sci. 615, 36–49.

Brook-Carter, P. T., Peral, B., Ward, C. J., Thompson, P., Hughes, J., Maheshwar, M. M., Nellist, M., Gamble, V., Harris, P. C. & Sampson, J. R. (1994). Deletion of the TSC2 and PKD1 genes associated with severe infantile polycystic kidney disease—a contiguous gene syndrome. Nature Genetics, 8, 218–332.

Chomczynski, P. and Sacchi, N. (1987). Single-step method of RNA isolation by acid guanidinium thiocyanate-phenol-chloroform extraction. Anal. Biochem. 162, 156–159.

Dayhoff, M. O., Schwartz, R. M. and Orcutt, B. C. (1978). In Atlas of Protein Sequence and Structure. Vol. 5, Suppl. 3. Dayhoff, M. O., ed. (Washington: NBRF), pp.345.

Deisseroth, A. and Hendrick, D. (1979). Activation of phenotypic expression of human globin genes from non-erythriod cells by a chromosome-dependent transfer to tetraploid mouse erythroleukaemia cells. Proc. Natl. Acad. Sci. USA 76, 2185–2189.

Eisenberg, D., Schwarz, E., Komaromy, M., and Wall, R. (1984). Analysis of membrane and surface protein sequences with the hydrophobic moment plot. J.Mol.Biol. 179, 125–142.

Feinberg, A. P., and Vogelstein, B. (1984). Addendum: a technique for radiolabelling DNA restriction endonuclease fragments to high specific activity. Anal. Biochem. 137, 266–267.

European Polycystic Kidney Disease Consortium (1994). The polycystic kidney disease 1 gene encodes at 14 kb transcript and lies within a duplicated region on chromosome 16. Cell. 77, 881–894.

Fryer, A. E., Chalmers, A., Connor, J. M., Fraser, I., Povey, S., Yates, A. D., Yates, J. R. W., and Osborne, J. P. (1987). Evidence that the gene for tuberous sclerosis is on chromosome 9. Lancet i, 659–661. Fryer, A. E., Chalmers, A. H., and Osborne, J. P. (1990). The value of investigation for genetic counselling in tuberous sclerosis. J. Med. Genet. 27, 217–223.

Germino, G. G., Barton, N. J., Lamb, J., Higgs, D. R., Harris, P., Xiao, G. H., Scherer, G., Nakamura, N. and Reeders, S. T. (1990). Identification of a locus which shows no genetic recombination with the autosomal dominant polycystic kidney disease gene on chromosome 16. Am. J. Hum. Genet. 46, 925–933.

Germino, G. G., Weinstat-Saslow, D., Himmelbauer, H., Gillespie, G. A. J., Somlo, S., Wirth, B., Barton, N., Harris, K. L., Frischauf, A-M., and Reeders, S. T. (1992). The gene for autosomal dominant polycystic kidney disease lies in a 750-kb CpG-rich region. Genomics 13, 144–151.

Germino, G. G., Somlo, S., Weinstat-Saslow, D. and Reeders, S. T. (1993) Positional cloning approach to the dominant polycystic kidney disease gene, PKD1. Kidney International, 43, Suppl. 39, 20–25.

Glass, D. B, El-Maghrabi, M. R., and Pilkis, S. J. (1986). Synthetic peptides corresponding to the site phosphorylated in 6-phosphofructo-2-kinase / fructose-2,6-biphosphatase as substrates of cyclic nucleotide-dependent protein kinases. J. Biol. Chem. 261, 2987–2993.

Gomez, M. R. (1988). Tuberous Sclerosis, 2nd edition (Raven Press, New York). Green, A. J. and Yates, J. R. W.

(1993). Loss of heterozygosity on chromosome 16p in hamartomata from patients with tuberous sclerosis. Am. J. Hum. Genet. 53 Suppl., 244.

Green, A. J., Smith, M & Yates, J. R. W. Loss of heterozygosity on chromosome 16p in hamartomes from tuberous sclerosis patients. Nature Genet. 6, 193–196 (1994).

Green. A. J. & Yates, J. R. W. The tuberous sclerosis gene on chromosome 9q34 acts as a growth suppressor. Hum. molec. Genet. (in the press) from Nature Genetics 1994.

Haines, J. L., Amos, J., Attwood, J., Bech-Hansen, N. T., Burley, M., Conneally, P. M., Connor, J. M., Fahsold, R., Flodman, P., Fryer, A., Halley, D. J. J., Jewell, A., Janssen, L. A. J., Kandt, R., Northrup, H., Osborne, J., Pericak-Vance, M., Povey, S., Sampson, J., Short, M. P., Smith, M., Speer, M., Trofatter, J. A., and Yates, J. R. W. (1991a). Genetic heterogeneity in tuberous sclerosis: study of a large collaborative dataset. Ann. N. Y. Acad. Sci. 615, 256–264.

Haines, J. L., Short, M. P., Kwiatkowski, D. J., Jewell, A., Andermann, E., Bejjani, B., Yang, C-H., Gusella, J. F., and Amos, J. A. (1991b). Localization of one gene for tuberous sclerosis within 9q32–9q34, and further evidence for heterogeneity. Am. J. Hum. Genet. 49, 764–772.

Harris, P. C., Barton, N. J., Higgs, D. R., Reeders, S. T., and Wilkie, A. O. M. (1990). A long-range restriction map between the a- globin complex and a marker closely linked to the polycystic kidney disease 1 (PKD1). Genomics 7, 195–206.

Hermann, B. G., Barlow, D. P., and Lehrach, H. (1987). A large inverted duplication allows homologous recombination between chromosomes heterozygous for the proximal t complex inversion. Cell 48, 813–825.

Himmelbauer, H., Germino, G. G., Ceccherini, I., Romeo, G., Reeders, S. T. and Frischauf, A. M. (1991). Saturating the region of the polycystic kidney disease gene with NotI linking clones. Am. J. Hum. Genet. 48, 325–334.

Horowitz, J. M., Yandell, D. W., Park, S. H., Canning, S., Whyte, P., Buchkovich, K., Harlow, E., Weinberg, R. A., and Dryja, T. P. (1989). Point mutational inactivation of the retinoblastoma antioncogene. Science 243, 937–940.

Janssen, L. A. J., Povey, S., Attwood, J., Sandkuyl, L. A., Lindhout, D., Flodman, P., Smith, M., Sampson, J. R., Haines, J. L., Merkens, E. C., Fleury, P., Short, P., Amos, J., and Halley, D. J. J. (1991). A comparative study on genetic heterogeneity in tuberous sclerosis: evidence for one gene on 9q34 and a second gene on 11q22-23. Ann. N. Y. Acad. Sci. 615, 306–315.

Kandt, R. S., Haines, J. L., Smith, M., Northrup, H., Gardner, R. J. M., Short, M. P., Dumars, K., Roach, E. S., Steingold, S., Wall, S., Blanton, S. H., Flodman, P., Kwiatkowski, D. J., Jewell, A., Weber, J. L., Roses, A. D. and Pericak-Vance, M. A. (1992). Linkage of an important gene locus for tuberous sclerosis to a chromosome 16 marker for polycystic kidney disease. Nature Genet. 2, 37–41.

Knudson, A. G. (1971). Mutation and cancer: statistical study of retinoblastoma. Proc. Natl. Acad. Sci. USA 68, 820–823. Kozak, M. (1987). An analysis of 5'-noncoding sequences from 699 vertebrate messenger RNAs. Nucl. Acids Res. 15, 8125–8148.

Kwiatkowski, D. J., Armour, J., Bale, A. E., Fountain, J. W., Goudie, D., Haines, J. L., Knowles, M. A., Pilz, A., Slaugenhaupt, S., and Povey, S. (1993). Report on the second international workshop on human chromosome 9. Cytogenet. Cell Genet. 64, 94–106.

Landschulz, W. H., Johnson, P. F., and McKnight, S. L. (1988). The leucine zipper: A hypothetical structure common to a new class of DNA binding proteins. Science 240, 1759–1764.

Latif, F., Tory, K., Gnarra, J., Yao, M., Duh, F-M., Orcutt, M. L., Stackhouse, T., Kuzmin, I., Modi, W., Geil, L., Schmidt, L., Zhou, F., Li, H., Wei, M. H., Chen, F., Glenn, G., Choyke, P., Walther, M. M., Weng, Y., Duan, D-S. R., Dean, M., Glavac, D., Richards, F. M., Crossey, P. A., Ferguson-Smith, M. A., Le Paslier, D., Chumakov, I., Cohen, D., Chinault, A. C., Maher, E. R., Linehan, W. M., Zbar, B., and Lerman, M. I. (1993). Identification of the von Hippel-Lindau disease tumor suppressor gene. Science 260, 1317–1320.

Legius, E., Marchuk, D. A., Collins, F. S., and Glover, T. W. (1993). Somatic deletion of the neurofibromatosis type 1 gene in a neurofibrosarcoma supports a tumour suppressor gene hypothesis. Nature Genet. 3, 122–126.

Martin, G. A., Viskochil, D., Bollag, G., McCabe, P. C., Crosier, W. J., Haubruck, H., Conroy, L., Clark, R., O'Connell, P., Cawthon, R. M., Innis, M. A., and McCormick, F. (1990). The GAP- related domain of the neurofibromatosis type 1 gene product interacts with ras p21. Cell 63, 843–849.

Nellist, M., Brook-Carter, P. T., Connor, J. M., Kwiatkowski, D. J., Johnson, P., and Sampson, J. R. (1993). Identification of markers flanking the tuberous sclerosis locus on chromosome 9 (TSC1). J. Med. Genet. 30, 224–227.

Northrup, H., Kwiatkowski, D. J., Roach, E. S., Dobyns, W. B., Lewis, R. A., Herman, G. E., Rodriguez, E., Daiger, S. P., and Blanton, S. H. (1992). Evidence for genetic heterogeneity in tuberous sclerosis: one locus on chromosome 9 and at least one locus elsewhere. Am. J. Hum. Genet. 51, 709–720.

Orita, M., Iwahana, H., Kanazawa, H., Hayashi, K., and Sekiya, T. (1989). Detection of polymorphisms of human DNA by gel electrophoresis as single-strand conformation polymorphisms. Proc. Natl. Acad. Sci. USA 86, 2766–2770.

Osborne, J. P., Fryer, A., and Webb, D. (1991). Epidemiology of tuberous sclerosis. Ann. N.Y. Acad. Sci. 615, 125–127.

Patschinsky, T., Hunter, T., Esch, F. S., Cooper, J. A., and Sefton, B. M. (1982). Analysis of the sequence of amino acids surrounding sites of tyrosine phosphorylation. Proc. Natl. Acad. Sci. USA 79, 973–977.

Pinna, L.A. (1990). Casein kinase 2: an eminence grise in cellular regulation? Biochim. Biophys. Acta 1054, 267–284.

Povey, S., Attwood, J., Janssen, L. A. J., Burley, M., Smith, M., Flodman, P., Morton, N. E., Edwards, J. H., Sampson, J. R., Yates, J. R. W., Haines, J. L., Amos, J., Short, M. P., Sandkuyl, L. A., Halley, D. J. J., Fryer, A. E., Bech-Hansen, T., Mueller, R., Al- Ghazali, L., Super, M., and Osborne, J. (1991). An attempt to map two genes for tuberous sclerosis using novel two-point methods. Ann. N. Y. Acad. Sci. 615, 298–305.

Rack, K. A., Harris, P. C., MacCarthy, A. B., Boone, R., Raynham, H., McKinley, M., Fitchett, M., Towe, C. M., Rudd, P., Armour, J. A. L., Lindenbaum, R. H. and Buckle V. J. (1993). Characterization of three de novo derivative chromosomes 16 by "reverse chromosome painting" and molecular analysis. Am. J. Hum. Genet. 52, 987–997.

Riordan, J. R., Rommens, J. M., Kerem, B-S., Alon, S., Rozmahel, R., Grzelczak, Z., Zielenski, J., Lok, S., Plavsic, N., Chou, J- L., Drumm, M. L., Iannuzzi, M. C., Collins, F. S. and Tsui, L. C. (1989). Identification of the cystic fibrosis gene: cloning and characterisation of complimentary DNA. Science 245, 1066–1072.

Rouleau, G. A., Merel, P., Lutchman, M., Sanson, M., Zucman, J., Marineau, C., Hoang-Xuan, K., Demczuk, S., Desmaze, C., Plougastel, B., Pulst, S. M., Lenoir, G., Bijlsma, E., Fahsold, R., Dumanski, J., de Jong, P., Parry, D., Eldrige, R., Aurias, A., Delattre, O., and Thomas, G. (1993). Alteration in a new gene encoding a putative membrane-organizing protein causes neurofibromatosis type 2. Nature 363, 515–521.

Royle, N. J., Armour, J. A., Webb, M., Thomas, A., and Jeffreys, A. J. (1992) A hypervariable locus D16S309 located at the distal end of 16p. Nucl. Acids Res. 20, 1164.

Rubinfeld, B., Crosier, W. J., Albert, I., Conroy, L., Clark, R., McCormick, F., and Polakis, P. (1992). Localisation of the rap1GAP catalytic domain and sites of phosphorylation by mutational analysis. Mol. Cell. Biol. 12, 4634–4642.

Sambrook, J., Fritsch, E. F., and Maniatis, T. (1989). Molecular Cloning: A Laboratory Manual, Second Edition (Cold Spring Harbor, N.Y.: Cold Spring Harbour Laboratory Press).

Sampson, J. R., Yates, J. R. W., Pirrit, L. A., Fleury, P., Winship, I., Beighton, P., and Connor, J. M. (1989a). Evidence for genetic heterogeneity in tuberous sclerosis. J. Med. Genet. 26, 511–516.

Sampson, J. R., Scahill, S. J., Stephenson, J. B. P., Mann, L. and Connor, J. M. (1989b). Genetic aspects of tuberous sclerosis in the west of Scotland. J. Med. Genet. 26, 28–31.

Sampson, J. R., Janssen, L. A. J., Sandkuijl, L. A. and the Tuberous Sclerosis Collaborative Group (1992). Linkage investigation of three putative tuberous sclerosis determining loci on chromosomes 9q, 11q and 12q. J. Med. Genet. 29, 861–866.

Smith, M., Handa, K., He, W. and Spear, G. (1993). Loss of heterozygosity for chromosome 16p13.3 markers in renal hamartomas from tuberous sclerosis patients. Am. J. Hum. Genet. 53, Suppl, 366.

Stallings, R. L., Torney, D. C., Hildebrand, C. E., Longmire, J. L., Deaven, L. L., Jett, J. H., Doggett, N. A. and Moyzis, R. K. (1990). Physical mapping of human chromosomes by repetitive sequence fingerprinting. Proc. Natl. Acad. Sci. USA 87, 6218–6222.

Thompson, A. D., Shen, Y., Holman, K., Sutherland, G. R., Callen, D. F. and Richards, R. I. (1992). Isolation and characterisation of (AC)n microsatellite genetic markers from human chromosome 16. Genomics 13, 402–408.

Trofatter, J. A., MacCollin, M. M., Rutter, J. L., Murrell, J. R., Duyao, M. P., Parry, D. M., Eldridge, R., Kley, N., Menon, A. G., Pulaski, K., Haase, V. H., Ambrose, C. M., Munroe, D., Bove, C., Haines, J. L., Martuza, R. L., MacDonald, M. E., Seizinger, B. R., Short, P. M., Buckler, A. J., and Gusella, J. F. (1993). A novel moesin-, ezrin-, radixin-like gene is a candidate for the neurofibromatosis 2 tumor suppressor. Cell 72, 791–800.

van der Hoeve, J. (1933). Les phakomatoses de Bourneville, de Recklinghausen et de von Hippel-Lindau. J. Belge Neurol. Psychiat. 33, 752–762.

Viskochil, D., Buchberg, A. M., Xu, G., Cawthon, R. M., Stevens, J., Wolff, R. K., Culver, M., Carey, J. C., Copeland, N. G., Jenkins, N. A., White, R., and O'Connell, P. (1990). Deletions and a translocation interrupt a cloned gene at the neurofibromatosis type 1 locus. Cell 62, 187–192.

von Heijne, G. (1985). Signal sequences. The limits of variation. J.Mol.Biol. 184, 99–105.

Wilkie, A. O. M., Buckle, V. J., Harris, P. C., Lamb, J., Barton, N. J., Reeders, S. T., Lindenbaum, R. H., Nicholls, R. D., Barrow, M., Bethlenfalvay, N. C., Hutz, M. H., Tolmie, J. L., Weatherall, D. J., and Higgs, D. R. (1990). Clinical features and molecular analysis of the a thalassemia/mental retardation syndromes. I. Cases due to deletions involving chromosome band 16p13.3. Am. J. Hum. Genet. 46, 1112–1126.

Woodgett, J. R., Gould, K. L., and Hunter, T. (1986). Substrate specificity of protein kinase C. Use of synthetic peptides corresponding to physiological sites as probes for substrate recognition requirements. Eur. J. Biochem. 161, 177–184.

Xu, G., O'Connell, P., Viskochil, D., Cawthon, R., Robertson, M., Culver, M., Dunn, D., Stevens, J., Gesteland, R., White, R., and Weiss, R. (1990). The neurofibromatosis type 1 gene encodes a protein related to GAP. Cell 62, 599–608.

What is claimed is:

1. A method for screening a subject to determine whether said subject is a TSC2-associated disorder carrier or a patient having a TSC2-associated disorder, which method comprises detecting the presence of and/or evaluating the characteristics of TSC2 DNA, TSC2 RNA and/or TSC2 polypeptide in a biological sample from said patient, wherein a difference in the presence and/or characteristics of said TSC2 DNA, TSC2 RNA and/or TSC2 polypeptide between said biological sample and the presence and/or characteristics of TSC2 DNA, TSC2 RNA and/or TSC2 polypeptide in a biological sample from a subject not carrying or afflicted with a TSC2-associated disorder is indicative of the presence, predisposition or tendency of the patient to develop a disorder.

2. A method according to claim 1 which comprises detecting and/or evaluating whether the TSC2 nucleic acid is mutated, deleted, or is not expressing normal TSC2 protein.

3. A method for screening a subject to determine whether said subject is a TSC2-associated disorder carrier or a patient having a TSC2-associated disorder, which method comprises detecting the presence of and/or evaluating the characteristics of TSC2 nucleic acid in a biological sample from said patient with a probe comprising the sequence presented in SEQ ID No.:1.

4. The method of claim 3 wherein the detection and/or evaluation includes the step of comparing the results thereof with results obtained using nucleic acid derived from a patient having a mutant TSC2 gene wherein the mutation is selected from the group consisting of:

(a) [WS-13] 32 kb are deleted flanked by CW13 and CW9;

(b) [WS-9] about 46 kb are deleted with breakpoints in SM9 and CW12;

(c) [WS-211] about 75 kb are deleted with breakpoints between CW9 and CW15 distally, and between CW23 and CW21 proximally;

(d) [WS-97] about 75 kb are deleted between BFS2 and SM9 distally, and within CW20 proximally;

(e) [WS-53] a large deletion between, distally, CW23 and JH1 such that about 0.6 kb of TSC2 is deleted;

(f) [WS-212] about 75 kb are deleted between SM9-CW9 distally and the TSC2 3'UTR proximally as shown in FIG. 8;

(g) [WS-215] about 160 kb are deleted between CW20 and CW10-CW36 as shown in FIG. 8;

(h) [WS-227] about 50 kb are deleted between CW20 and JH11 as shown in FIG. 8;

(i) [WS-219] about 27 kb are deleted between JH1 and JH6 as shown in FIG. 8;

(j) [WS-250] about 160 kb are deleted between CW20 and BLu24 as shown in FIG. 8; and (k) [WS-194] about 65 kb are deleted between CW20 and CW10, wherein a difference between the results obtained using nucleic acid in a biological sample from said patient and the results obtained using nucleic acid derived from a patient having a mutant TSC2 gene is indicative of the presence of a wild type TSC2 gene expressing normal TSC2 protein in the patient.

5. A method according to claim 1 or 2, wherein said screening includes applying a nucleic acid amplification process to said sample to amplify a fragment of the TSC2 DNA or cDN-corresponding to the TSC2 RNA.

6. A method according to claim 3 or 4, wherein said screening includes applying a nucleic acid amplification process to said sample to amplify a fragment of the TSC2 DNA or cDNA corresponding to the TSC2 RNA.

* * * * *